US010263191B2

(12) United States Patent
Mizuki et al.

(10) Patent No.: US 10,263,191 B2
(45) Date of Patent: Apr. 16, 2019

(54) AROMATIC AMINE DERIVATIVE, AND ORGANIC ELECTROLUMINESCENT ELEMENT COMPRISING THE SAME

(71) Applicant: IDEMITSU KOSAN CO., LTD., Tokyo (JP)

(72) Inventors: Yumiko Mizuki, Sodegaura (JP); Masakazu Funahashi, Sodegaura (JP); Masahiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 15/648,188

(22) Filed: Jul. 12, 2017

(65) Prior Publication Data

US 2017/0317284 A1 Nov. 2, 2017

Related U.S. Application Data

(63) Continuation of application No. 15/259,831, filed on Sep. 8, 2016, now Pat. No. 9,741,938, which is a continuation of application No. 14/850,357, filed on Sep. 10, 2015, now Pat. No. 9,466,800, which is a continuation of application No. 13/773,203, filed on Feb. 21, 2013, now Pat. No. 9,166,179, which is a (Continued)

(30) Foreign Application Priority Data

Apr. 24, 2009 (JP) ................................ 2009-105963
Aug. 26, 2009 (JP) ................................ 2009-195976

(51) Int. Cl.

| | |
|---|---|
| ***H01L 51/00*** | (2006.01) |
| ***C07F 7/08*** | (2006.01) |
| ***C07D 307/91*** | (2006.01) |
| ***C07D 333/76*** | (2006.01) |
| ***C09K 11/06*** | (2006.01) |
| ***H05B 33/18*** | (2006.01) |
| ***H05B 33/20*** | (2006.01) |
| *H01L 51/50* | (2006.01) |

(52) U.S. Cl.

CPC .......... *H01L 51/006* (2013.01); *C07D 307/91* (2013.01); *C07D 333/76* (2013.01); *C07F 7/081* (2013.01); *C07F 7/0812* (2013.01); *C09K 11/06* (2013.01); *H01L 51/0054* (2013.01); *H01L 51/0061* (2013.01); *H01L 51/0065* (2013.01); *H01L 51/0068* (2013.01); *H01L 51/0094* (2013.01); *H05B 33/18* (2013.01); *H05B 33/20* (2013.01); *C09K 2211/1007* (2013.01); *C09K 2211/1011* (2013.01); *C09K 2211/1014* (2013.01); *C09K 2211/1022* (2013.01); *C09K 2211/1088* (2013.01); *C09K 2211/1092* (2013.01); *H01L 51/0052* (2013.01); *H01L 51/0058* (2013.01); *H01L 51/0067* (2013.01); *H01L 51/0073* (2013.01); *H01L 51/0074* (2013.01); *H01L 51/5012* (2013.01); *H01L 51/5056* (2013.01); *H01L 51/5072* (2013.01); *H01L 51/5088* (2013.01); *H01L 51/5092* (2013.01)

(58) Field of Classification Search

None

See application file for complete search history.

(56) References Cited

U.S. PATENT DOCUMENTS 6,517,957 B1 2/2003 Senoo et al.
6,858,325 B2 2/2005 Senoo et al.
(Continued)

FOREIGN PATENT DOCUMENTS

CN 1362464 A 8/2002
DE 102004029695 A1 1/2006
(Continued)

OTHER PUBLICATIONS

Huang et al., "Organic electroluminescent derivatives containing dibenzothiophene and diarylamine segments," Journal of Materials Chemistry, 2005, 15:3233-3240.
(Continued)

*Primary Examiner* — Vu A Nguyen

(74) *Attorney, Agent, or Firm* — Foley & Lardner LLP

(57) ABSTRACT

An aromatic amine derivative represented by the following formula (1) wherein at least one of $Ar_1$ to $Ar_4$ is a heterocyclic group represented by the following formula (2) wherein $X_1$ is an oxygen atom or a sulfur atom.

(1)

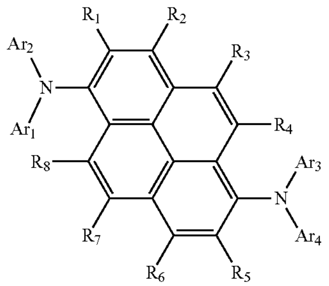

(2)

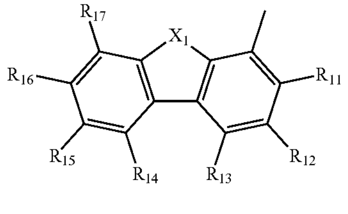

30 Claims, No Drawings

Related U.S. Application Data continuation of application No. 13/138,750, filed as application No. PCT/JP2010/002959 on Apr. 23, 2010, now Pat. No. 8,431,250.

(56) References Cited

U.S. PATENT DOCUMENTS

| | | | |
|---|---|---|---|
| 7,700,201 | B2 | 4/2010 | Seo et al. |
| 2002/0028346 | A1 | 3/2002 | Shi et al. |
| 2002/0177009 | A1 | 11/2002 | Suzuki et al. |
| 2003/0077480 | A1 | 4/2003 | Hosokawa et al. |
| 2003/0118866 | A1 | 6/2003 | Oh et al. |
| 2003/0157364 | A1 | 8/2003 | Senoo et al. |
| 2004/0053069 | A1 | 3/2004 | Sotoyama et al. |
| 2004/0137270 | A1 | 7/2004 | Seo et al. |
| 2005/0064233 | A1 | 3/2005 | Matsuura et al. |
| 2005/0089717 | A1 | 4/2005 | Cosimbescu et al. |
| 2005/0156164 | A1 | 7/2005 | Sotoyama |
| 2005/0280008 | A1 | 12/2005 | Ricks et al. |
| 2006/0008672 | A1 | 1/2006 | Jarikov |
| 2006/0043858 | A1 | 3/2006 | Ikeda et al. |
| 2006/0134456 | A1 | 6/2006 | Ikeda et al. |
| 2006/0251925 | A1 | 11/2006 | Hosokawa et al. |
| 2006/0269782 | A1 | 11/2006 | Liao et al. |
| 2007/0063638 | A1 | 3/2007 | Tokairin et al. |
| 2007/0090755 | A1 | 4/2007 | Eida et al. |
| 2007/0060777 | A1 | 5/2007 | Moriwaki et al. |
| 2007/0114917 | A1 | 5/2007 | Funahashi et al. |
| 2007/0152565 | A1 | 7/2007 | Kubota et al. |
| 2007/0202354 | A1 | 8/2007 | Funahashi |
| 2007/0243411 | A1 | 10/2007 | Takashima et al. |
| 2007/0252511 | A1 | 11/2007 | Funahashi |
| 2007/0278938 | A1 | 12/2007 | Yabunouchi et al. |
| 2008/0001123 | A1 | 1/2008 | Inoue et al. |
| 2008/0015399 | A1 | 1/2008 | Funahashi |
| 2008/0061685 | A1 | 3/2008 | Chesterfield |
| 2008/0113101 | A1 | 5/2008 | Inoue et al. |
| 2008/0124572 | A1 | 5/2008 | Mizuki et al. |
| 2008/0160342 | A1 | 7/2008 | Meng et al. |
| 2008/0203905 | A1 | 8/2008 | Je et al. |
| 2008/0206447 | A1 | 8/2008 | Inoue et al. |
| 2008/0303425 | A1 | 12/2008 | Rostovtsev et al. |
| 2008/0303428 | A1 | 12/2008 | Rostovtsev et al. |
| 2008/0306303 | A1 | 12/2008 | Rostovtsev et al. |
| 2009/0015144 | A1 | 1/2009 | Takashima et al. |
| 2009/0134384 | A1 | 5/2009 | Stoessel et al. |
| 2009/0134781 | A1 | 5/2009 | Jang et al. |
| 2009/0200926 | A1 | 8/2009 | Lee et al. |
| 2009/0206748 | A1 | 8/2009 | Moriwaki et al. |
| 2009/0273277 | A1 | 11/2009 | Lee et al. |
| 2010/0052526 | A1 | 3/2010 | Je et al. |
| 2010/0072888 | A1 | 3/2010 | Kim et al. |
| 2010/0108997 | A1 | 5/2010 | Kim et al. |
| 2010/0117028 | A1 | 5/2010 | Takeshima et al. |
| 2010/0155714 | A1 | 6/2010 | Seo et al. |
| 2010/0171109 | A1 | 7/2010 | Hishimura et al. |
| 2010/0187512 | A1 | 7/2010 | Ito |
| 2010/0207110 | A1 | 8/2010 | Nishimura et al. |
| 2010/0289014 | A1 | 11/2010 | Ito et al. |
| 2010/0295030 | A1 | 11/2010 | Kawamura |
| 2010/0301313 | A1 | 12/2010 | Ito et al. |
| 2010/0314615 | A1 | 12/2010 | Mizuki et al. |
| 2010/0320452 | A1 | 12/2010 | Kawamura |
| 2011/0024736 | A1 | 2/2011 | Kambe et al. |
| 2011/0068683 | A1 | 3/2011 | Kawamura et al. |
| 2011/0156016 | A1 | 6/2011 | Kawamura et al. |
| 2011/0193064 | A1 | 8/2011 | Funahashi |
| 2011/0220886 | A1 | 9/2011 | Takeshima et al. |
| 2011/0240125 | A1 | 10/2011 | Ikeda et al. |
| 2011/0248246 | A1 | 10/2011 | Ogita et al. |
| 2011/0042660 | A1 | 12/2011 | Kawamura et al. |
| 2013/0187137 | A1 | 7/2013 | Mizuki et al. |

FOREIGN PATENT DOCUMENTS

| | | | |
|---|---|---|---|
| EP | 2 182 040 | A2 | 5/2010 |
| EP | 2 189 508 | A2 | 5/2010 |
| EP | 2182039 | A2 | 5/2010 |
| EP | 2189508 | A2 | 5/2010 |
| EP | 2 202 283 | A1 | 6/2010 |
| EP | 2 270 897 | A2 | 1/2011 |
| JP | H08-199162 | A | 8/1996 |
| JP | H08199162 | A | 8/1996 |
| JP | H11-035532 | A | 2/1999 |
| JP | 2000273056 | A | 10/2000 |
| JP | 2002124385 | A | 4/2002 |
| JP | 2004006379 | A | 1/2004 |
| JP | 2004075580 | A | 3/2004 |
| JP | 2004-204238 | A | 7/2004 |
| JP | 2005-041843 | A | 2/2005 |
| JP | 2005-222751 | A | 8/2005 |
| JP | 2006128715 | A | 5/2006 |
| JP | 2007-077094 | A | 3/2007 |
| JP | 2007-238500 | A | 9/2007 |
| JP | 2008162921 | A | 7/2008 |
| JP | 2008244424 | A | 10/2008 |
| JP | 2009-010364 | A | 1/2009 |
| JP | 2009016693 | A | 1/2009 |
| JP | 2009-246354 | A | 10/2009 |
| JP | 2009-290051 | A | 12/2009 |
| JP | 2010006818 | A | 1/2010 |
| JP | 2010030973 | A | 2/2010 |
| JP | 2010-056190 | A | 3/2010 |
| JP | 2010150425 | A | 7/2010 |
| JP | 2010-186637 | A | 8/2010 |
| JP | 2011-231108 | | 11/2011 |
| KR | 2007-0105081 | A | 10/2007 |
| KR | 100793795 | B1 | 1/2008 |
| KR | 2010-0021367 | A | 2/2010 |
| TW | 200838850 | A | 10/2008 |
| TW | 201012898 | A | 4/2010 |
| WO | WO-02/38524 | A1 | 5/2002 |
| WO | WO-2004/018587 | A1 | 3/2004 |
| WO | WO-2004/018588 | A1 | 3/2004 |
| WO | WO-2004/096945 | A1 | 11/2004 |
| WO | WO-2005/054162 | A1 | 6/2005 |
| WO | WO-2005/061656 | A1 | 7/2005 |
| WO | WO-2005/108335 | A1 | 11/2005 |
| WO | WO-2005/108348 | A1 | 11/2005 |
| WO | WO 2006011879 | A1 | 2/2006 |
| WO | WO 2006011880 | A1 | 2/2006 |
| WO | WO-2006/128800 | A1 | 12/2006 |
| WO | WO-2006/137210 | A1 | 12/2006 |
| WO | WO-2007/029798 | A1 | 3/2007 |
| WO | WO-2007/058035 | A1 | 5/2007 |
| WO | WO-2007/108666 | A1 | 9/2007 |
| WO | WO-2008/108256 | A1 | 9/2008 |
| WO | WO-2008/136522 | A1 | 11/2008 |
| WO | WO-2008/143229 | A1 | 11/2008 |
| WO | WO 2009008347 | A1 | 1/2009 |
| WO | WO-2009/020095 | A1 | 2/2009 |
| WO | WO-2009/084512 | A1 | 7/2009 |
| WO | WO-2009/102026 | A1 | 8/2009 |
| WO | WO 2009102026 | A1 | 8/2009 |
| WO | WO-2009/107596 | A1 | 9/2009 |
| WO | WO 2009107596 | A1 | 9/2009 |
| WO | WO 2009133917 | A1 | 11/2009 |
| WO | WO 2009142230 | A1 | 11/2009 |
| WO | WO 2010/010924 | A1 | 1/2010 |
| WO | WO-2010/010924 | A1 | 1/2010 |
| WO | WO-2010/013675 | A1 | 2/2010 |
| WO | WO 2010016405 | A1 | 2/2010 |
| WO | WO-2010/114256 | A2 | 10/2010 |

OTHER PUBLICATIONS

Ku et al., "Organic Electroluminescent Bis(diarylamino)Dibenzofuran Derivatives," Journal of the Chinese Chemical Society, 2006, 53:1317-1324.

Non-Final Office Action issued in U.S. Appl. No. 13/138,750 dated Dec. 10, 2012.

(56) References Cited

OTHER PUBLICATIONS

Japanese Office Action dated Dec. 4, 2012 issued in Application No. JP 2011-510233.
Notice of Allowance issued in U.S. Appl. No. 13/138,750 dated Mar. 20, 2013.
Taiwanese Office Action issued in TW Application No. 099112839 dated Aug. 29, 2014.
Notice of Allowance issued in U.S. Appl. No. 15/259,831 dated Apr. 13, 2017.
Supplemental Notice of Allowability issued in U.S. Appl. No. 15/259,831 dated Apr. 27, 2017.

AROMATIC AMINE DERIVATIVE, AND ORGANIC ELECTROLUMINESCENT ELEMENT COMPRISING THE SAME

CROSS-REFERENCE TO RELATED APPLICATIONS

The present application is a continuation of U.S. patent application Ser. No. 15/259,831, filed Sep. 8, 2016, which is a continuation of U.S. patent application Ser. No. 14/850,357, filed Sep. 10, 2015 (now U.S. Pat. No. 9,466,800 B2), which is a continuation of U.S. patent application Ser. No. 13/773,203, filed Feb. 21, 2013 (now U.S. Pat. No. 9,166,179 B2), which is a continuation of U.S. patent application Ser. No. 13/138,750, filed Sep. 23, 2011 (now U.S. Pat. No. 8,431,250 B2), which is a U.S. National Stage Entry of International Patent Application No. PCT/JP2010/002959, filed Apr. 23, 2010, which claims the benefit of priority from Japanese Patent Application No. 2009-105963, filed Apr. 24, 2009 and Japanese Patent Application No. 2009-195976, filed Aug. 26, 2009, the entireties of which are all hereby incorporated herein by reference.

TECHNICAL FIELD

The invention relates to an aromatic amine derivative and an organic electroluminescence device using the same. In particular, the invention relates to an organic electroluminescence device having a long life, a high luminous efficiency and a high chromatic purity and an aromatic amine derivative realizing the same.

BACKGROUND ART

An organic electroluminescence (EL) device using an organic material is a promising solid-state emitting type inexpensive and large full-color display device, and has been extensively developed. In general, an organic EL device includes an emitting layer and a pair of opposing electrodes holding the emitting layer therebetween. Emission is a phenomenon in which when an electric field is applied between the electrodes, electrons are injected from the cathode and holes are injected from the anode, the electrons recombine with the holes in the emitting layer to produce an excited state, and energy is emitted as light when the excited state returns to the ground state.

Conventional organic EL devices have a higher driving voltage than an inorganic light-emitting diode. The luminance or luminous efficiency thereof is also low, and their properties tend to deteriorate significantly. For these reasons, conventional organic EL devices have not been put in a practical use. Although recent organic EL devices have been improved gradually, further improvement in luminous efficiency, prolongation in life time, color reproducibility or the like has been demanded.

The performance of an organic EL device has been improved gradually by improving an emitting material for an organic EL. In particular, improvement in chromatic purity of a blue-emitting organic EL device (shortening of the emission wavelength) is an important technology which leads to improvement in color reproducibility of a display.

As the example of a material used in an emitting layer, Patent Document 1 discloses an emitting material having dibenzofuran. This emitting material is capable of emitting blue light having a short wavelength. However, an organic EL device using this emitting material has a poor luminous efficiency, and hence, further improvement has been desired.

Patent Documents 4 and 5 each disclose a diaminopyrene derivative. Patent Document 2 discloses a combination of an anthracene host and an arylamine. Patent Documents 3 to 5 disclose a combination of an anthracene host with a specific structure and a diaminopyrene dopant. Further, Patent Documents 6 to 8 disclose an anthracene-based host material.

In each material and in each combination, although it can be admitted that emission properties are improved, emission properties are not yet sufficient. Under such circumstances, an emitting material capable of realizing a high luminous efficiency and capable of emitting light at a further shorter wavelength has been demanded.

Patent Document 9 discloses the use of an aromatic amine derivative which has an arylene group at the central thereof and in which a dibenzofuran ring is bonded to a nitrogen atom as the hole-transporting material. Patent Document 10 discloses the use of an aromatic amine derivate in which a dibenzofuran ring, dibenzothiophen ring, a benzofuran ring, a benzothiophen ring or the like is bonded to a nitrogen atom through an arylene group as a hole-transporting material. However, no example is given in which this aromatic amine derivative is used as an emitting material.

RELATED ART DOCUMENTS

Patent Documents

[Patent Document 1] WO2006/128800
[Patent Document 2] WO2004/018588
[Patent Document 3] WO2004/018587
[Patent Document 4] JP-A-2004-204238
[Patent Document 5] WO2005/108348
[Patent Document 6] WO2005/054162
[Patent Document 7] WO2005/061656
[Patent Document 8] WO2002/038524
[Patent Document 9] JP-A-H11-35532
[Patent Document 10] WO2007/125714

SUMMARY OF THE INVENTION

The invention is aimed at providing an organic EL device capable of emitting blue light with a high chromatic purity at a high luminous efficiency and a material which can be used in organic thin film layers of the organic EL device.

According to the invention, the following aromatic amine derivative and the organic electroluminescence device can be provided.

1. An aromatic amine derivative represented by the following formula (1):

(1)

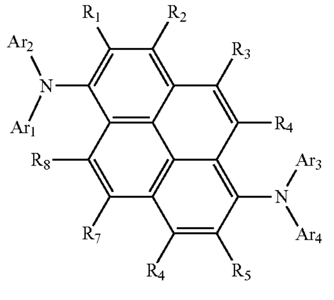

wherein $R_1$ to $R_8$ are independently a hydrogen atom, a halogen atom, a substituted or unsubstituted alkyl group having 1 to 20 carbon atoms, a substituted or unsubstituted cycloalkyl group having 3 to 10 ring carbon atoms, a substituted or unsubstituted silyl group, a cyano group or a substituted or unsubstituted aryl group having 6 to 30 carbon atoms that form a ring (hereinafter referred to as "ring carbon atoms"), and $Ar_1$ to $Ar_4$ are independently a substituted or unsubstituted aryl group having 6 to 30 ring carbon atoms or a substituted or unsubstituted heterocyclic group having 5 to 30 atoms that form a ring (hereinafter referred to as the "ring atoms"), provided that at least one of $Ar_1$ to $Ar_4$ is a heterocyclic group represented by the following formula (2):

(2)

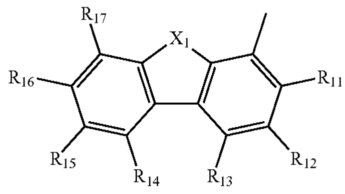

wherein $R_{11}$ to $R_{17}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms or a substituted or unsubstituted heterocyclic group having 5 to 20 ring atoms, adjacent substituents of $R_{11}$ to $R_{17}$ may be bonded to form a saturated or unsaturated ring, and $X_1$ is an oxygen atom or a sulfur atom.

2. The aromatic amine derivative according to 1 which is represented by the following formula (3):

3. The aromatic amine derivative according to 2 wherein $Ar_2$ and $Ar_4$ are a heterocyclic group represented by the following formula (4):

(4)

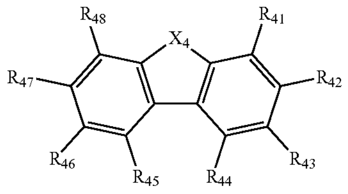

wherein one of $R_{41}$ to $R_{48}$ is used for connection to the nitrogen atom, and the other substituents are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms or a substituted or unsubstituted heterocyclic group having 5 to 20 ring atoms, adjacent substituents of $R_{41}$ to $R_{48}$ may be bonded to form a saturated or unsaturated ring, and $X_4$ is an oxygen atom or a sulfur atom.

4. The aromatic amine derivative according to any one of 1 to 3 wherein $R_1$ to $R_8$ are a hydrogen atom.

5. The aromatic amine derivative according to any one of 1 to 3 wherein $R_2$ is a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 30 ring carbon atoms, and $R_1$ and $R_3$ to $R_8$ are a hydrogen atom.

(3)

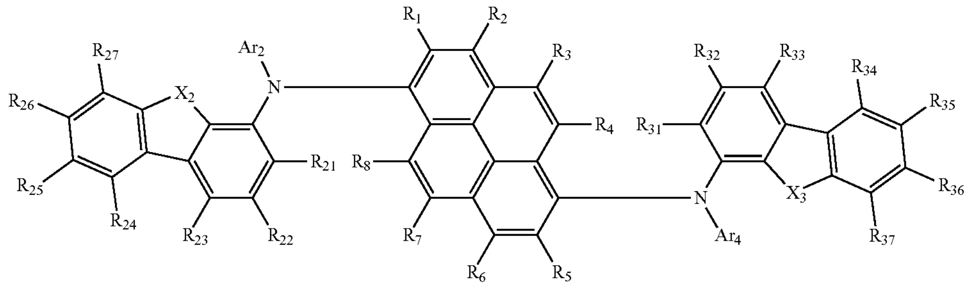

wherein $R_1$ to $R_8$, $Ar_2$ and $Ar_4$ are the same as those in formula (1), $R_{21}$ to $R_{27}$ and $R_{31}$ to $R_{37}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms or a substituted or unsubstituted heterocyclic group having 5 to 20 ring atoms, adjacent substituents of $R_{21}$ to $R_{27}$ and $R_{31}$ to $R_{37}$ may be bonded to form a saturated or unsaturated ring, and $X_2$ and $X_3$ are independently an oxygen atom or a sulfur atom.

6. The aromatic amine derivative according to any one of 1 to 3 wherein $R_2$ and $R_6$ are a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 30 ring carbon atoms, and $R_1$, $R_3$, $R_4$, $R_5$, $R_7$ and $R_8$ are a hydrogen atom.

7. The aromatic amine derivative according to any one of 1 to 6 wherein $X_1$, $X_2$, $X_3$ and $X_4$ are an oxygen atom.

8. The aromatic amine derivative according to any one of 1 to 7 which is an emitting material for an organic electroluminescence device.

9. The aromatic amine derivative according to any one of 1 to 8 which is a doping material for an organic electroluminescence device.

10. An organic electroluminescence device comprising one or more organic thin film layers comprising an emitting layer between an anode and a cathode, wherein at least one layer of the organic thin film layers comprises the aromatic amine derivative according to any one of 1 to 9 singly or as a component of a mixture.

11. The organic electroluminescence device according to 10, wherein the at least one layer is an emitting layer.

12. The organic electroluminescence device according to 10, wherein the at least one layer comprises the aromatic amine derivative according to any one of 1 to 9 and an anthracene derivative represented by the following formula (5):

(5)

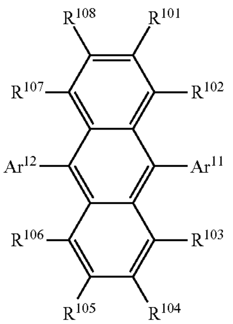

wherein $Ar^{11}$ and $Ar^{12}$ are independently a substituted or unsubstituted monocyclic group having 5 to 50 ring atoms, a substituted or unsubstituted fused ring group having 8 to 50 ring atoms, or a group formed by combination of the monocyclic group and the fused ring group and $R^{101}$ to $R^{108}$ are independently a group selected from a hydrogen atom, a substituted or unsubstituted monocyclic group having 5 to 50 ring atoms, a substituted or unsubstituted fused ring group having 8 to 50 ring atoms, a group formed by combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom and a cyano group.

13. The organic electroluminescence device according to 12 wherein in formula (5), $Ar^{11}$ and $Ar^{12}$ are independently a substituted or unsubstituted fused ring group having 10 to 50 ring carbon atoms.

14. The organic electroluminescence device according to 12 wherein in formula (5), one of $Ar^{11}$ and $Ar^{12}$ is a substituted or unsubstituted monocyclic group having 5 to 50 ring atoms, and the other is a substituted or unsubstituted fused ring group having 8 to 50 ring atoms.

15. The organic electroluminescence device according to 14 wherein in formula (5), $Ar^{12}$ is a naphthyl group, a phenanthryl group, a benzanthryl group or a dibenzofuranyl group, and $Ar^{11}$ is a phenyl group which is unsubstituted or substituted by a monocyclic group or fused ring group.

16. The organic electroluminescence device according to 14 wherein in formula (5), $Ar^{12}$ is a substituted or unsubstituted fused ring group having 8 to 50 ring atoms, and $Ar^{11}$ is an unsubstituted phenyl group.

17. The organic electroluminescence device according to 12 wherein in formula (5), $Ar^{11}$ and $Ar^{12}$ are independently a substituted or unsubstituted monocyclic group having 5 to 50 ring atoms.

18. The organic electroluminescence device according to 17 wherein in formula (5), $Ar^{11}$ and $Ar^{12}$ are independently a substituted or unsubstituted phenyl group.

19. The organic electroluminescence device according to 18 wherein in formula (5), $Ar^{11}$ is an unsubstituted phenyl group and $Ar^{12}$ is a phenyl group having a monocyclic group or a fused ring group as a substituent.

20. The organic electroluminescence device according to 18 wherein in formula (5), $Ar^{11}$ and $Ar^{12}$ are independently a phenyl group having a monocyclic group or a fused ring group as a substituent.

According to the invention, an organic EL device capable of emitting blue light with a high chromatic purity at a high luminous efficiency, and a material which can be used for organic thin film layers of the organic EL device can be provided.

MODE FOR CARRYING OUT THE INVENTION

The aromatic amine derivative of the invention is represented by the following formula (1):

(1)

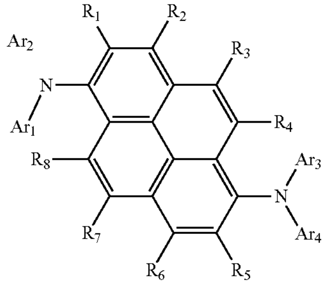

In the formula (1), $R_1$ to $R_8$ are independently a hydrogen atom, a halogen atom, a substituted or unsubstituted alkyl group having 1 to 20 carbon atoms, a substituted or unsubstituted cycloalkyl group having 3 to 10 ring carbon atoms, a substituted or unsubstituted silyl group, a cyano group or a substituted or unsubstituted aryl group having 6 to 30 carbon atoms, and $Ar_1$ to $Ar_4$ are independently a substituted or unsubstituted aryl group having 6 to 30 ring carbon atoms or a substituted or unsubstituted heterocyclic group having 5 to 30 ring atoms, provided that at least one of $Ar_1$ to $Ar_4$ is a heterocyclic group represented by the following formula (2):

(2)

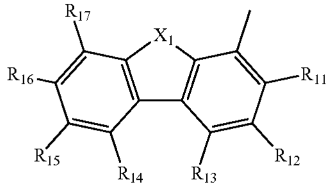

In the formula (2), $R_{11}$ to $R_{17}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms or a substituted or unsubstituted heterocyclic group having 5 to 20 ring atoms, adjacent substituents of $R_{11}$ to $R_{17}$ may be bonded to form a saturated or unsaturated ring, and $X_1$ is an oxygen atom or a sulfur atom.

The aromatic amine derivative is preferably represented by the following formula (3):

In the formula (2), $R_{11}$ to $R_{17}$ are preferably a hydrogen atom.

In the formula (3), $R_{21}$ to $R_{27}$ and $R_{31}$ to $R_{37}$ are preferably a hydrogen atom.

In the formula (4), $R_{41}$ to $R_{48}$ are preferably a hydrogen atom.

In the formula (1), it is preferred that $Ar_1$ to $Ar_4$ other than the heterocyclic group represented by the formula (2) be an unsubstituted aryl group having 6 to 30 ring carbon atoms.

In the formula (3), it is preferred that $Ar_2$ and $Ar_4$ be an aryl group having 6 to 30 ring carbon atoms.

(3)

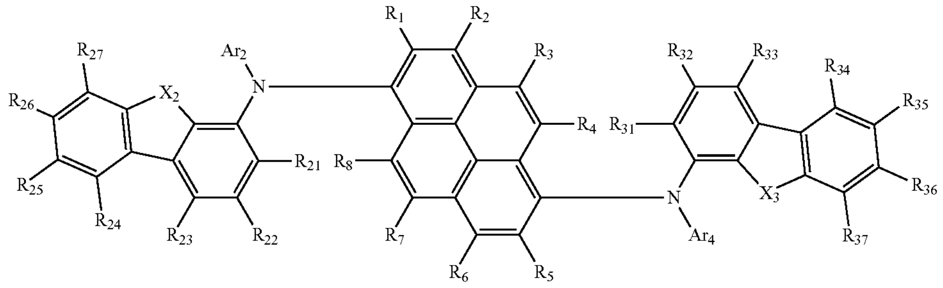

In the formula (3), $R_1$ to $R_8$ and $Ar_2$ and $Ar_4$ are the same as those in the formula (1), $R_{21}$ to $R_{27}$ and $R_{31}$ to $R_{37}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms, or a substituted or unsubstituted heterocyclic group having 5 to 20 ring atoms, adjacent substituents of $R_{21}$ to $R_{27}$ and $R_{31}$ to $R_{37}$ may form a saturated or unsaturated ring, and $X_2$ and $X_3$ are independently an oxygen atom or a sulfur atom.

It is preferred that, in the formulas (1) and (3), $R_2$ be a substituted or unsubstituted alkyl group having 1 to 20 carbon atoms, a substituted or unsubstituted cycloalkyl group having 3 to 10 ring carbon atoms, a substituted or unsubstituted silyl group or a substituted or unsubstituted aryl group having 6 to 30 ring carbon atoms, and $R_1$ and $R_3$ to $R_8$ be a hydrogen atom.

In another preferred embodiment, in the formulas (1) and (3), $R_2$ and $R_6$ are a substituted or unsubstituted alkyl group having 1 to 20 carbon atoms, a substituted or unsubstituted cycloalkyl group having 3 to 10 ring carbon atoms, a substituted or unsubstituted silyl group or a substituted or unsubstituted aryl group having 6 to 30 ring carbon atoms, and $R_1$, $R_3$, $R_4$, $R_5$, $R_7$ and $R_8$ are a hydrogen atom.

The substituted or unsubstituted alkyl group having 1 to 20 carbon atoms of $R_2$ and $R_6$ is preferably an alkyl group having 1 to 6 carbon atoms. The substituted or unsubstituted silyl group of $R_2$ and $R_6$ is preferably a substituted or unsubstituted alkylsilyl group having 3 to 30 carbon atoms, with a substituted or unsubstituted alkylsilyl group having 3 to 12 carbon atoms being more preferable.

In another preferred embodiment, in the formulas (1) and (3), $R_1$ to $R_8$ are preferably a hydrogen atom.

In the formulas (2) to (4), $X_1$, $X_2$, $X_3$ and $X_4$ are preferably an oxygen atom.

When $Ar_1$ to $Ar_4$ other than the heterocyclic group represented by the formula (2) are an unsubstituted aryl group having 6 to 30 ring carbon atoms, this aryl group is preferably a phenyl group, a naphthyl group, a phenanthryl group, a fluorenyl group, an anthracenyl group, a chrycenyl group or a fluoranthenyl group. It is particularly preferred that it be a phenyl group, a naphthyl group, a phenanthryl group or a fluorenyl group.

In another preferred embodiment, in the formula (1), it is preferred that $Ar_1$ to $Ar_4$ other than the heterocyclic group represented by the formula (2) be an aryl group having 6 to 30 ring carbon atoms and having a substituent.

In another preferred embodiment, in the formula (3), it is preferred that $Ar_2$ and $Ar_4$ be an aryl group having 6 to 30 ring carbon atoms and having a substituent.

Preferred examples of the substituent include a halogen atom, an alkyl group, a cycloalkyl group, a silyl group, an aryl group or a cyano group.

If $Ar_1$ to $Ar_4$ other than the heterocyclic group represented by the formula (2) is an aryl group having a substituent, this aryl group is preferably a phenyl group.

In another preferred embodiment, in the formula (3), it is preferred that $Ar_2$ and $Ar_4$ be a heterocyclic group represented by the following formula (4):

(4)

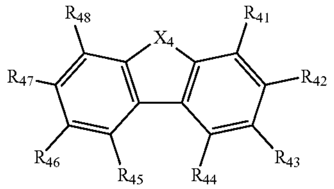

In the formula (4), one of $R_{41}$ to $R_{48}$ is used for connection to the nitrogen atom, and the other substituents are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted silyl group, a cyano group, a substituted or unsubstituted aryl group having 6 to 20 ring carbon atoms or a substituted or unsubstituted heterocyclic group having 5 to 20 ring atoms, adjacent substituents of $R_{41}$ to $R_{48}$ may be bonded to form a saturated or unsaturated ring, and $X_4$ is an oxygen atom or a sulfur atom.

In the specification, the "ring carbon atoms" mean carbon atoms that form a saturated ring, unsaturated ring or aromatic ring. The "ring atoms" mean carbon atoms and hetero atoms that form a hetero ring (including a saturated ring, unsaturated ring or aromatic ring).

In addition, as the substituent in the "substituted or unsubstituted . . . ", an alkyl group, a substituted or unsubstituted silyl group, an alkoxy group, an aryl group, an aryloxy group, an aralkyl group, a cycloalkyl group, a heterocyclic group, a halogen atom, an alkyl halide group, a hydroxyl group, a nitro group, a cyano group, a carboxy group or the like, which will be given later, can be given.

The "unsubstituted" means that a group is substituted with a hydrogen atom and the hydrogen atom of the invention includes light hydrogen, deuterium and tritium.

Each of the groups represented by $R_1$ to $R_8$, $R_{11}$ to $R_{17}$, $R_{21}$ to $R_{27}$, $R_{31}$ to $R_{37}$, $R_{41}$ to $R_{48}$ and $Ar_1$ to $Ar_4$ in the formulas (1) to (4), and the substituent in "substituted or unsubstituted . . . " will be mentioned below in detail.

Examples of the alkyl group include methyl, ethyl, propyl, isopropyl, n-butyl, s-butyl, isobutyl, t-butyl, n-pentyl, n-hexyl, n-heptyl and n-octyl. The alkyl group may be a substituent obtained by combination of an alkylene group and an aryl group or the like (a phenylmethyl group, 2-phenylisopropyl group or the like, for example).

The group preferably has 1 to 10 carbon atoms and more preferably 1 to 6 carbon atoms. Of these, methyl, ethyl, propyl, isopropyl, n-butyl, s-butyl, isobutyl, t-butyl, n-pentyl and n-hexyl are preferable.

As the substituted silyl group, an alkylsilyl group having 3 to 30 carbon atoms, an arylsilyl group having 8 to 30 ring carbon atoms or the like can be given. Examples thereof include a trimethylsilyl group, a triethylsilyl group, a t-butyldimethylsilyl group, a vinyldimethylsilyl group, a propyldimethylsilyl group, a triisopropylsilyl group, a triphenylsilyl group, or the like can be given.

The alkoxy group is represented by —OY. Examples for Y include those exemplified above for the alkyl group. The alkoxy group is methoxy or ethoxy, for example.

The alkenyl group and the alkynyl group mentioned as $R_{11}$ to $R_{17}$, $R_{21}$ to $R_{27}$, $R_{31}$ to $R_{37}$ and $R_{41}$ to $R_{48}$ are preferably a vinyl group and an ethynyl group, respectively.

Examples of the aryl group include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, naphthacenyl, pyrenyl, chrysenyl, benzo[c]phenanthryl, benzo[g]chrysenyl, triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, terphenyl and fluoranthenyl.

The aryl group mentioned as $R_1$ to $R_8$ preferably has 6 to 20 ring carbon atoms and more preferably 6 to 12 ring carbon atoms. Phenyl, biphenyl, tolyl, xylyl and 1-naphthyl are particularly preferable among the above-mentioned aryl groups.

The aryloxy group is represented by —OZ. Examples for Z include those described above for the aryl group or the examples of a monocyclic group and a fused ring group mentioned later. The aryloxy group is phenoxy, for example.

The aralkyl group is represented by —Y—Z. Examples for Y include alkylene corresponding to those described above for the alkyl group. Examples for Z include those described above for the aryl group. The aralkyl group is preferably an aralkyl group having 7 to 50 carbon atoms, wherein the aryl part has 6 to 49 (preferably 6 to 30, more preferably 6 to 20, and particular preferably 6 to 12) carbon atoms, and the alkyl part has 1 to 44 (preferably 1 to 30, more preferably 1 to 20, still more preferably 1 to 10, and particularly preferably 1 to 6) carbon atoms. For example, a benzyl group, phenylethyl group, or 2-phenylpropane-2-yl group can be given.

Examples of the cycloalkyl group include cyclopropyl, cyclobutyl, cyclopentyl, cyclohexyl, 4-methylcyclohexyl, adamantyl and norbornyl. The cycloalkyl group has preferably 3 to 10, further preferably 3 to 8, and particularly preferably 3 to 6 ring carbon atoms.

Examples of the heterocyclic group include pyrrolyl, pyrazinyl, pyridinyl, indolyl, isoindolyl, imidazolyl, furyl, benzofuranyl, isobenzofuranyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, quinolyl, isoquinolyl, quinoxalinyl, 1-carbazolyl, 2-carbazolyl, 3-carbazolyl, 4-carbazolyl, 9-carbazolyl, phenantridinyl, acridinyl, phenanthrolinyl, phenazinyl, phenothiazinyl, phenoxazinyl, oxazolyl, oxadiazolyl, furazanyl, thienyl and benzothiophenyl.

The above-mentioned heterocyclic group preferably has 5 to 20 ring atoms and more preferably 5 to 14 ring atoms.

1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-carbazolyl, 2-carbazolyl, 3-carbazolyl, 4-carbazolyl and 9-carbazolyl are preferable.

As the halogen atom, fluorine, chlorine, bromine and iodine can be given. Fluorine is preferable.

As the alkyl halide group, a fluoromethyl group, a difluoromethyl group, a trifluoromethyl group, a fluoroethyl group, a trifluoromethyl group, or the like can be given.

Specific examples of the aromatic amine derivative are given below.

D-1

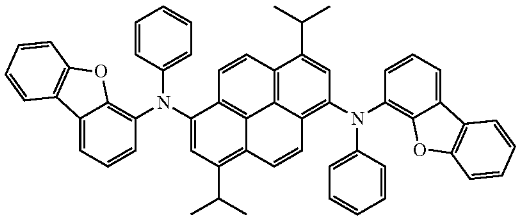

D-3

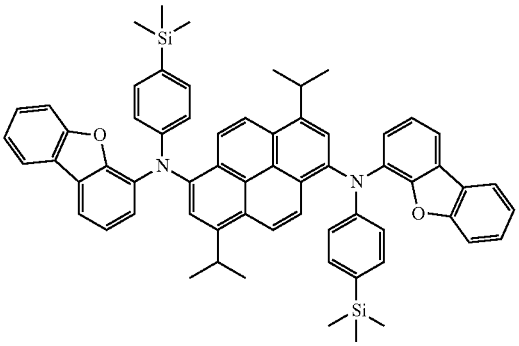

-continued
D-4
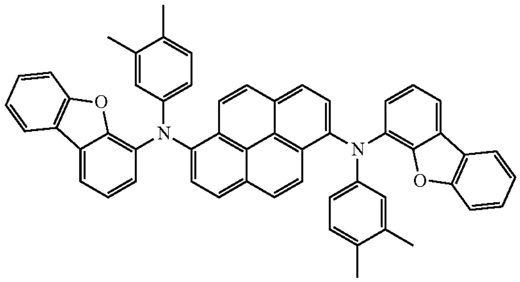
D-5
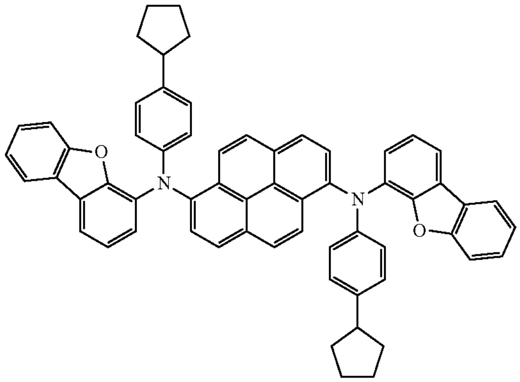
D-6
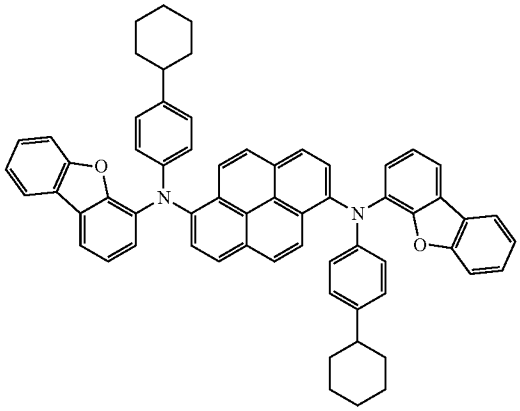
D-7
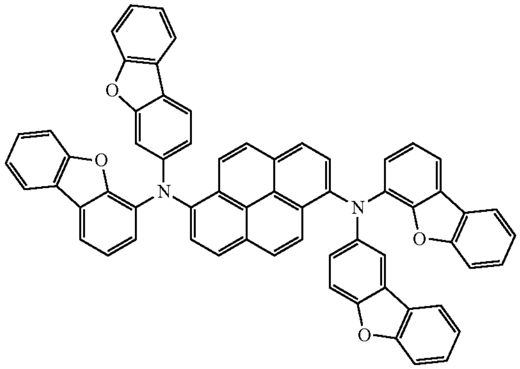
D-8
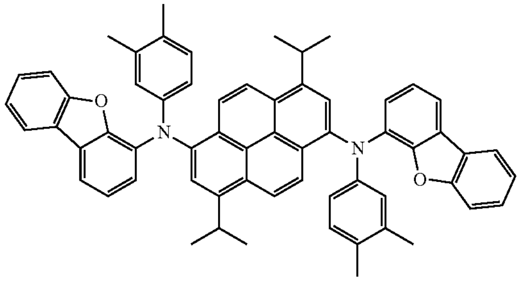
D-9
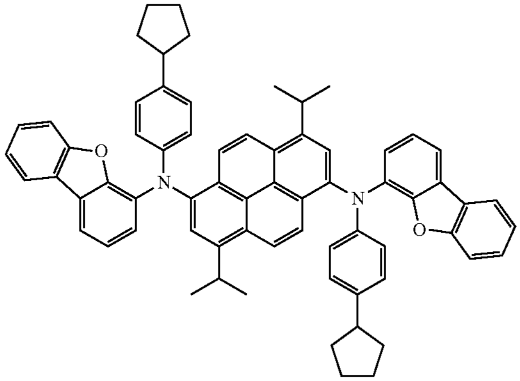
D-10
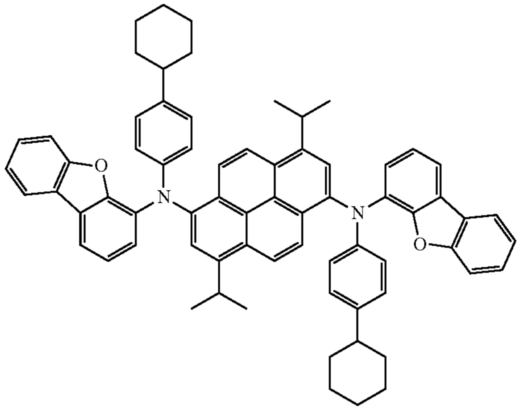
D-11
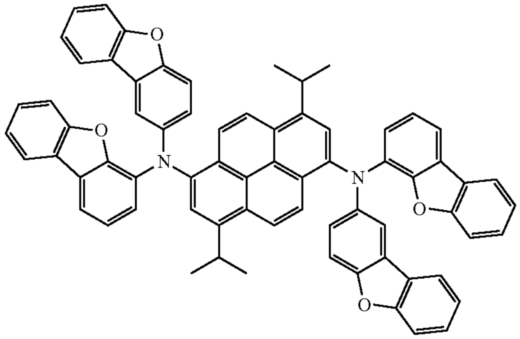

-continued
D-12
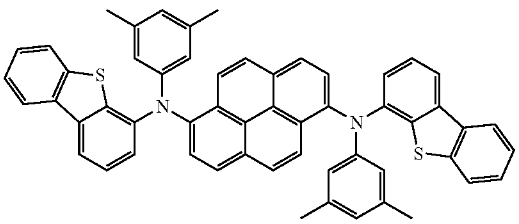
D-13
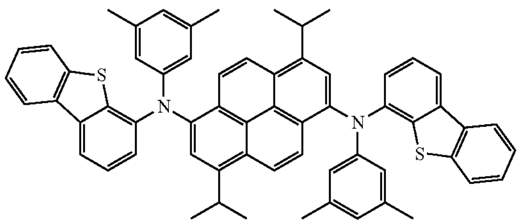
D-14
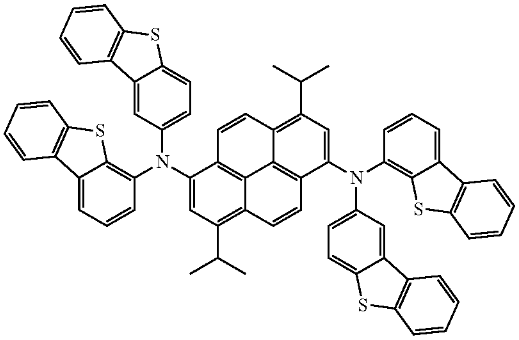
D-15
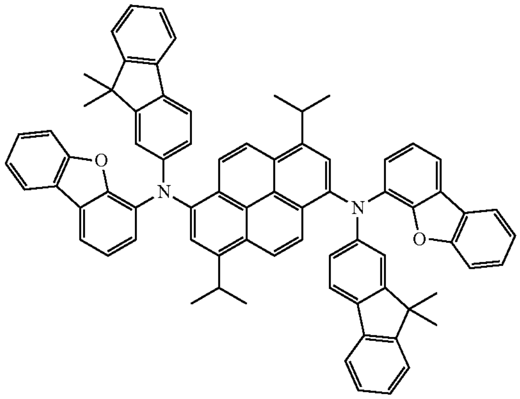
D-16
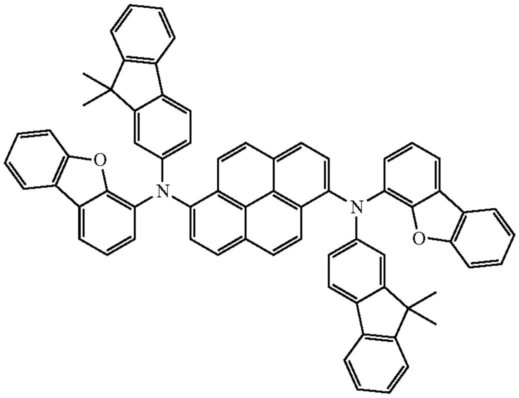
D-17
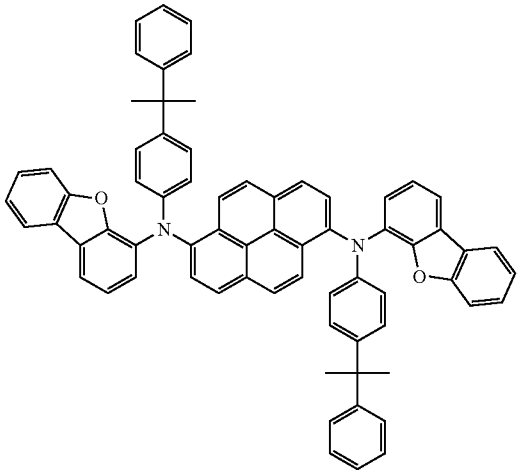
D-18
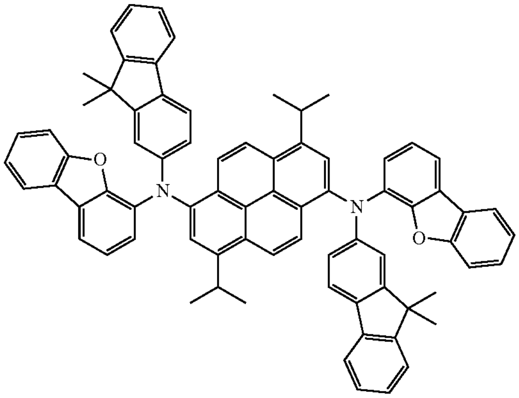
D-19
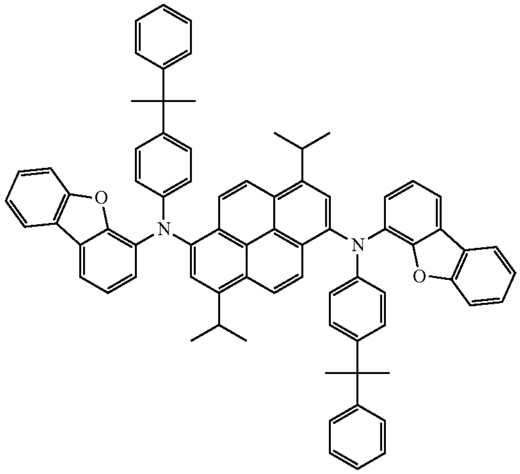

-continued
D-20
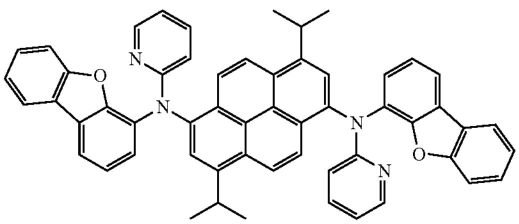
D-21
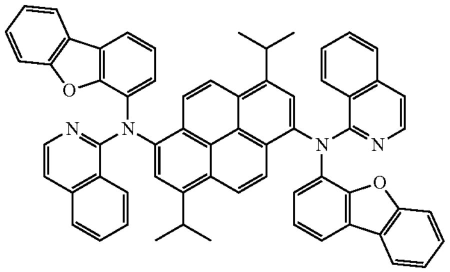
D-22
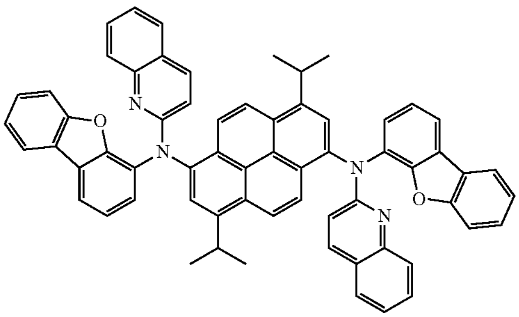
D-23
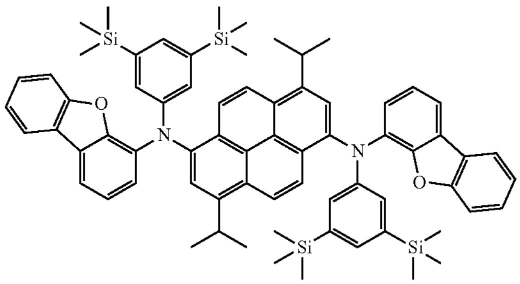
D-24
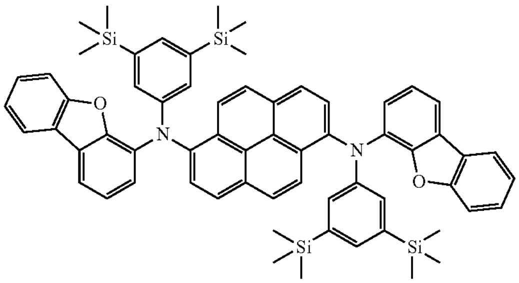
D-25
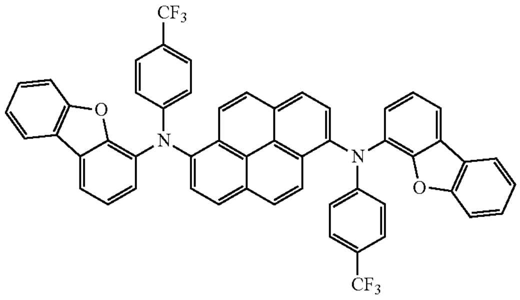
D-26
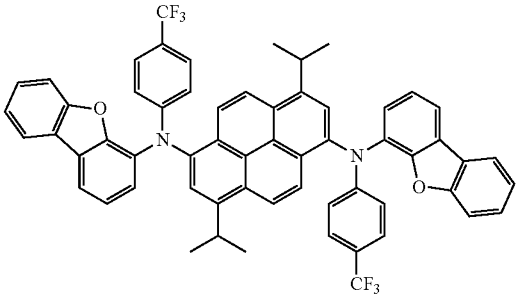
D-27
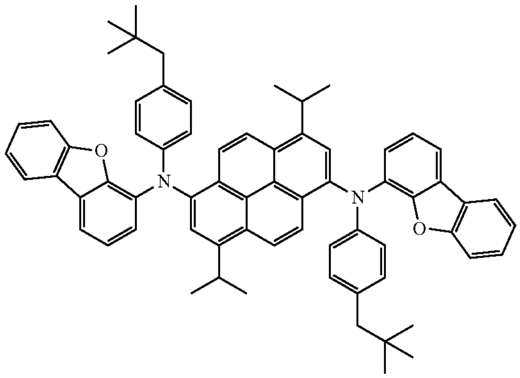

-continued
D-28
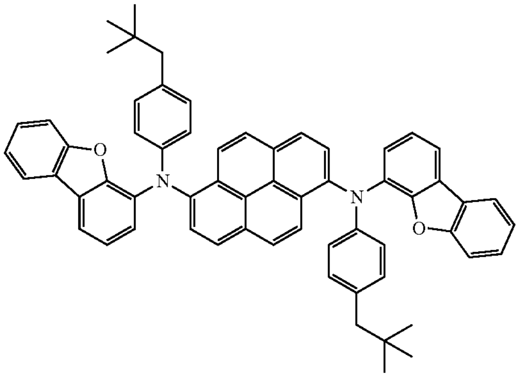
D-29
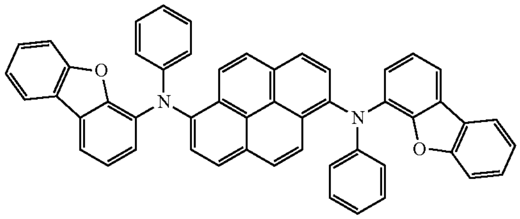
D-30
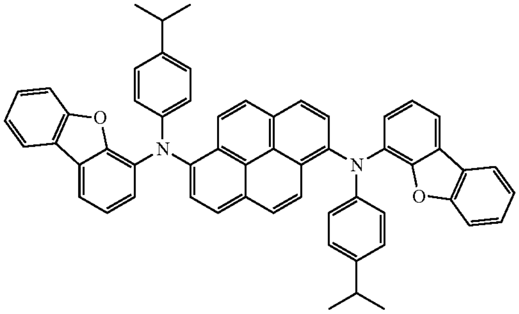
D-31
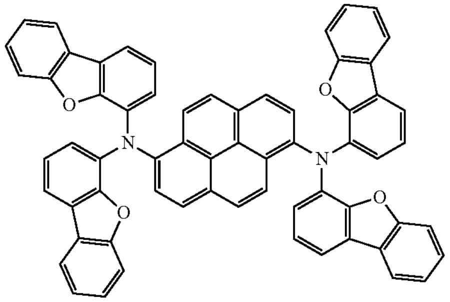
D-32
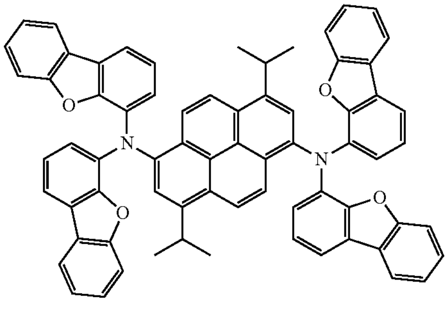
D-33
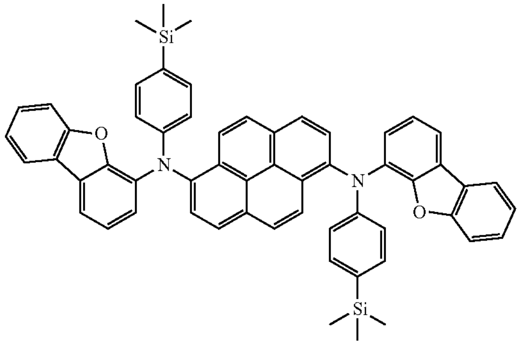
D-34
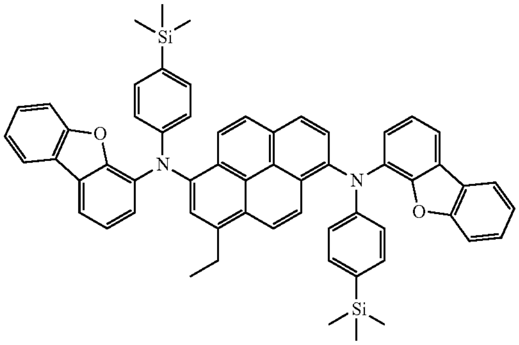
D-35
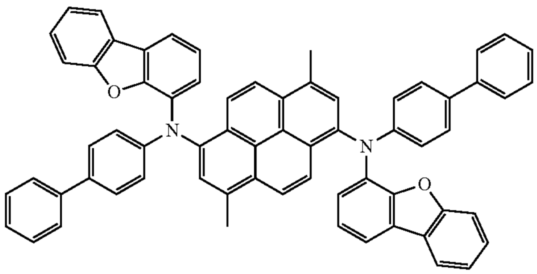

-continued
D-36
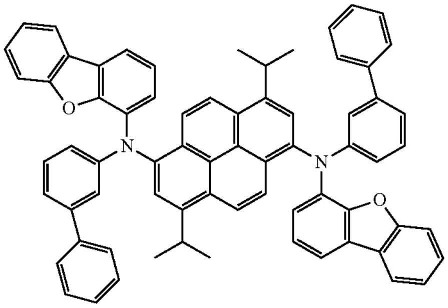
D-37
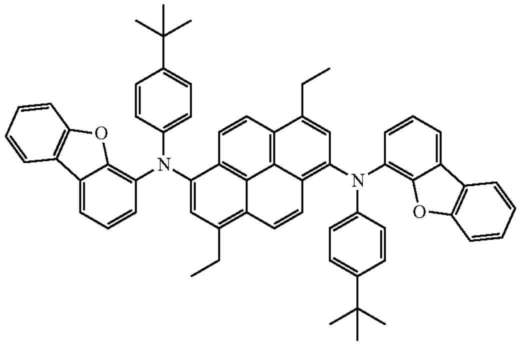
D-38
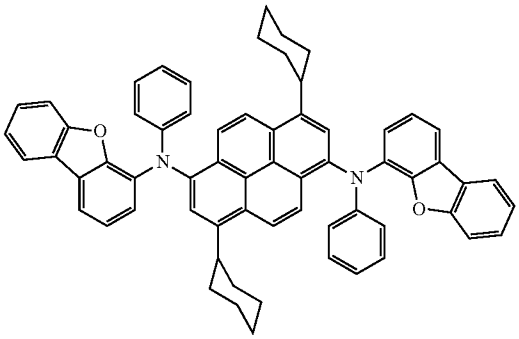
D-39
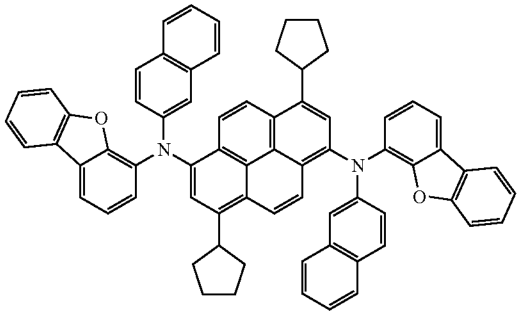
D-40
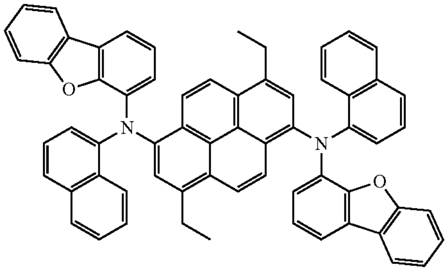
D-41
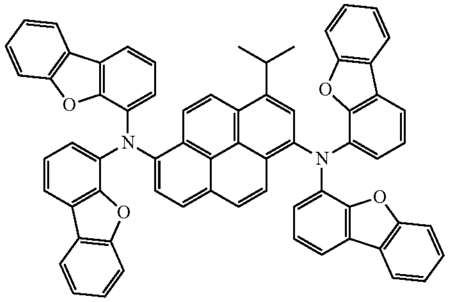
D-42
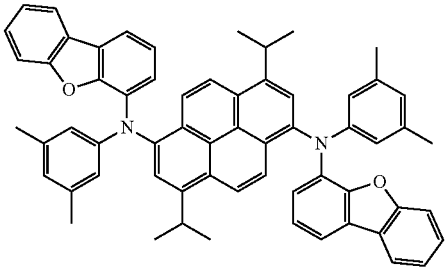
D-43
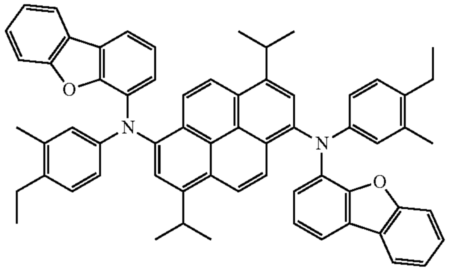
D-44
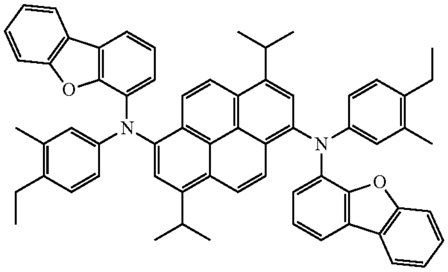
D-45
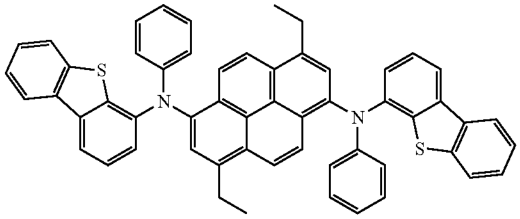

-continued
D-46
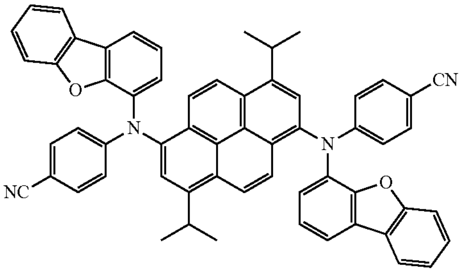
D-47
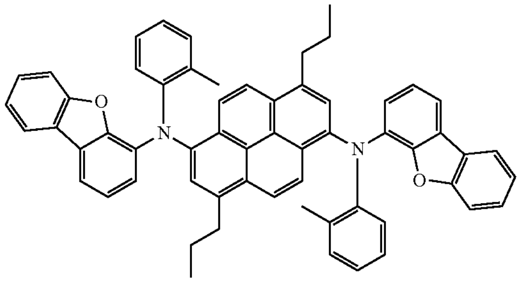
D-48
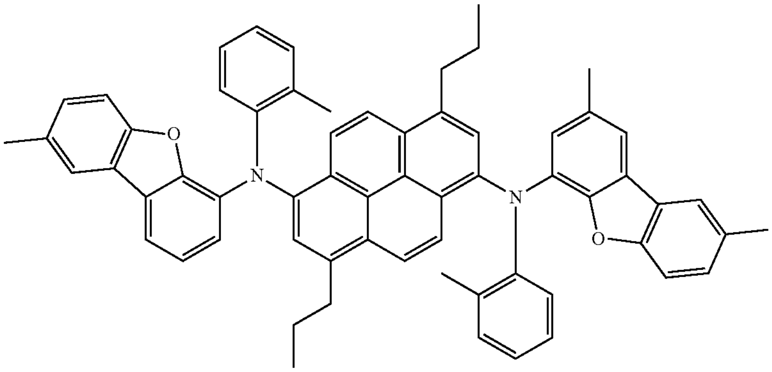
D-49
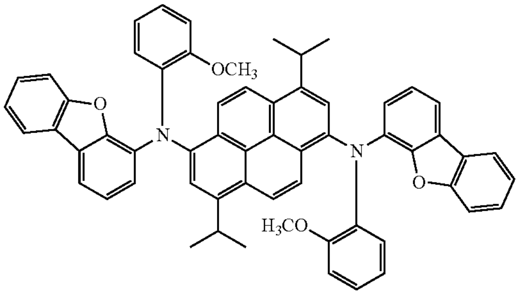
D-50
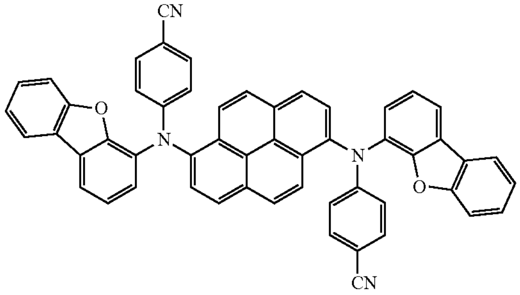
D-51
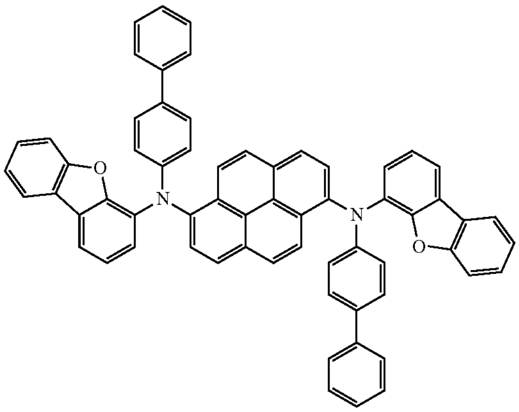
D-52
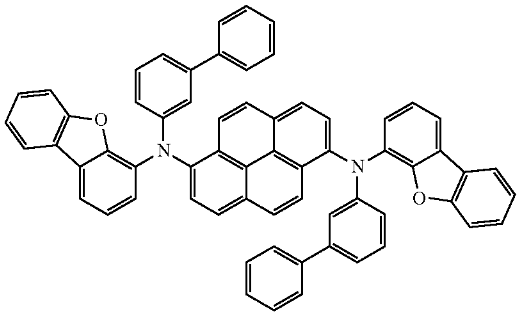

-continued
D-53
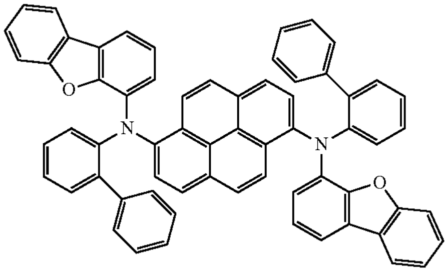
D-54
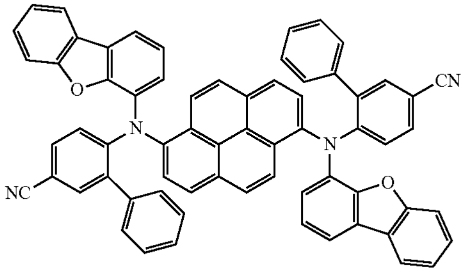
D-55
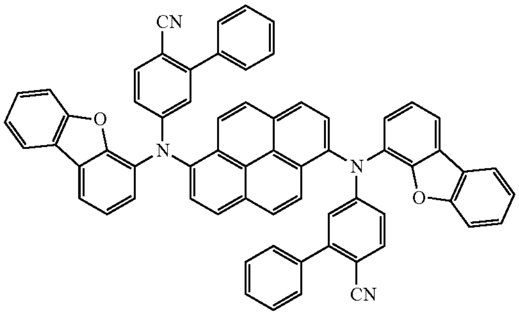
D-56
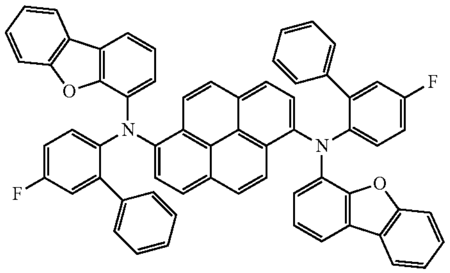
D-57
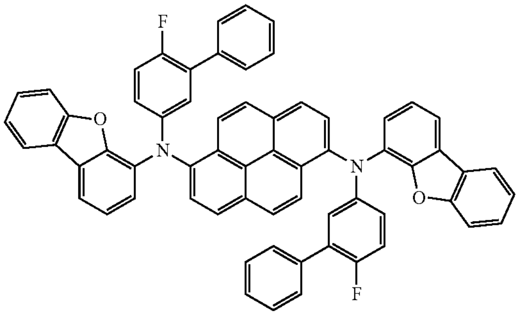
D-58
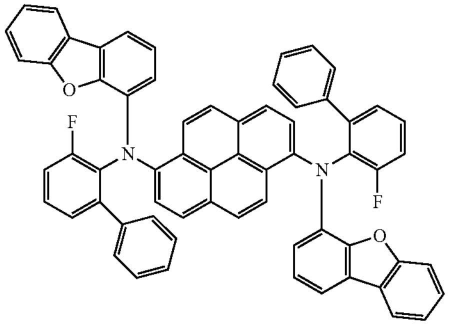
D-59
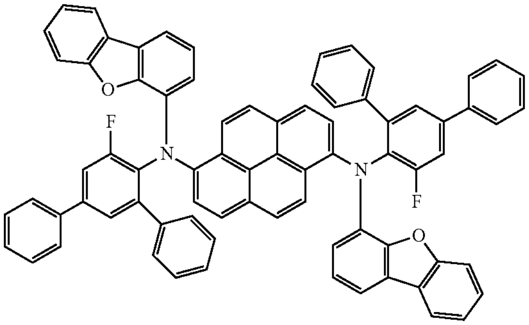
D-60
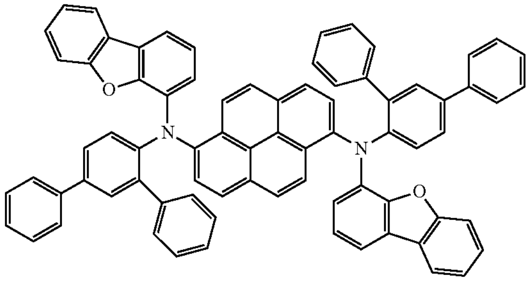
D-61
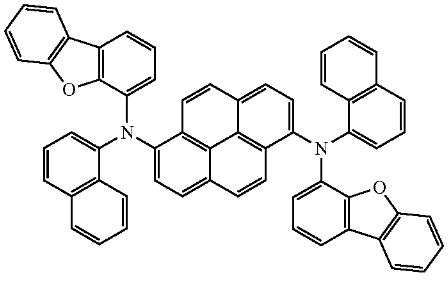
D-62
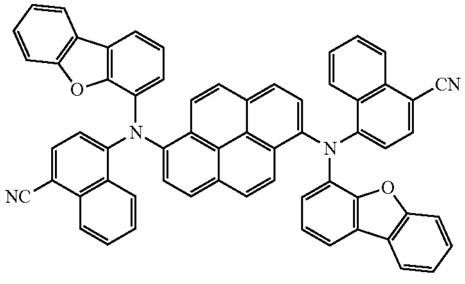

-continued
D-63
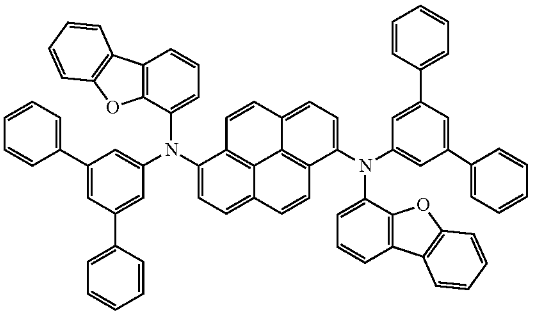
D-64
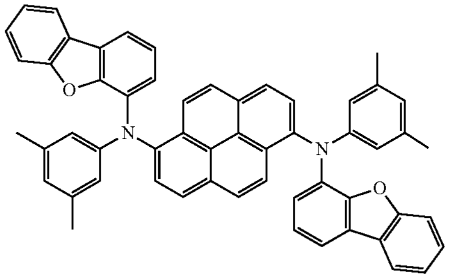
D-65
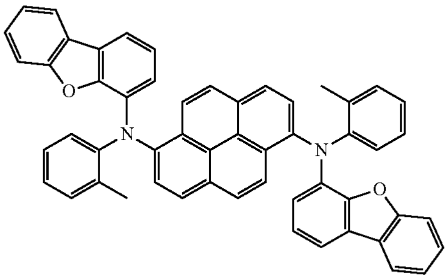
D-66
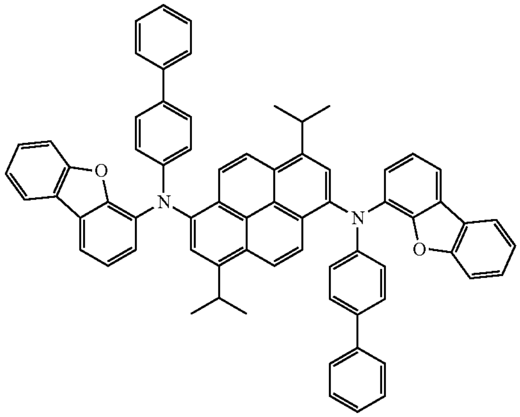
D-67
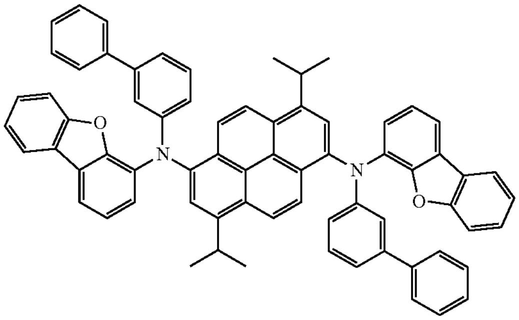
D-68
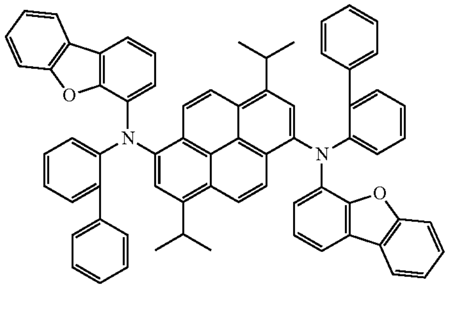
D-69
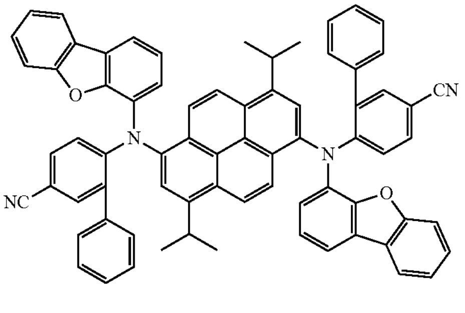
D-70
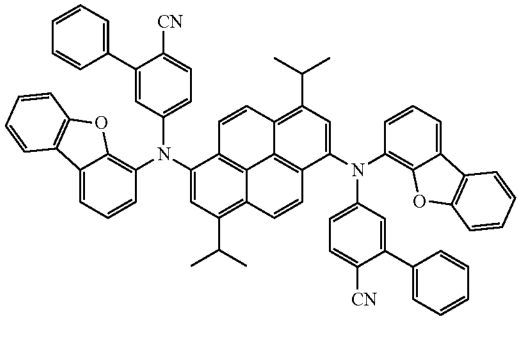

-continued
D-71
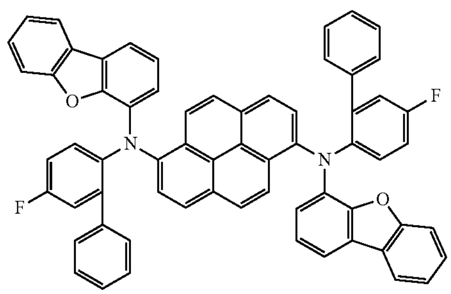
D-72
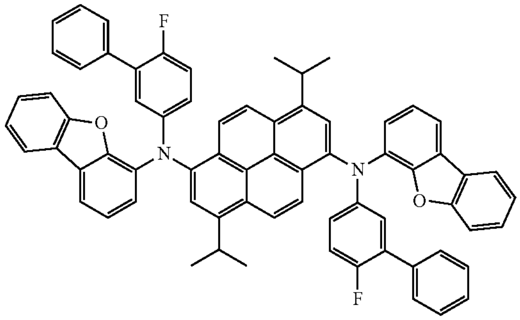
D-73
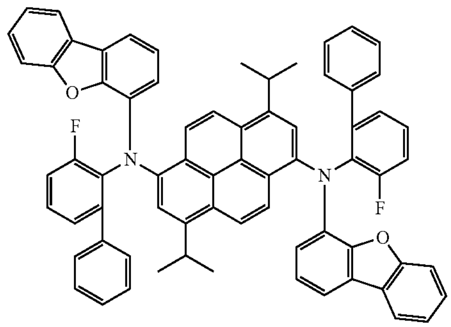
D-74
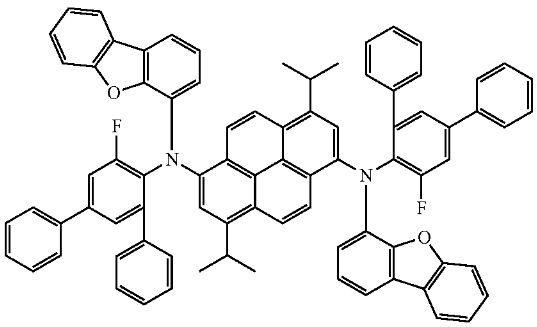
D-75
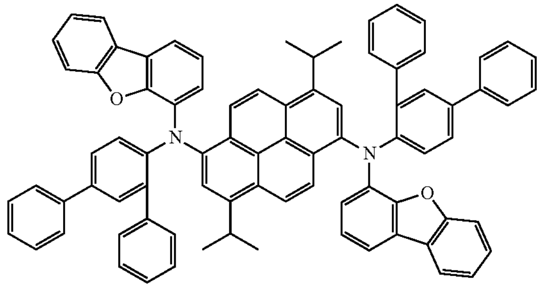
D-76
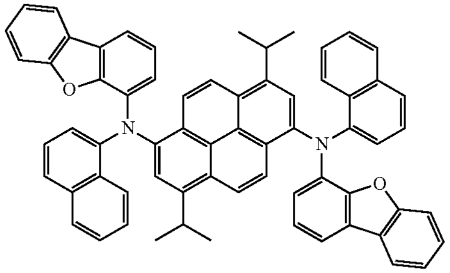
D-77
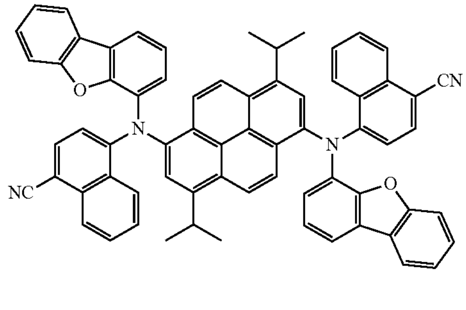
D-78
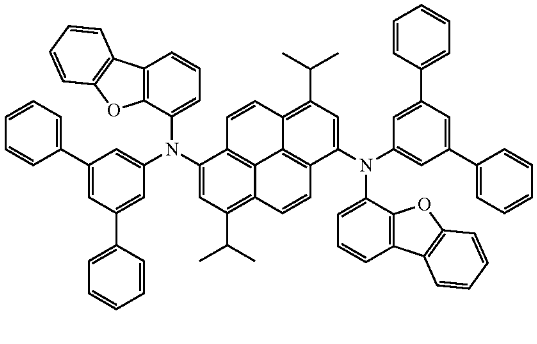

-continued
D-79
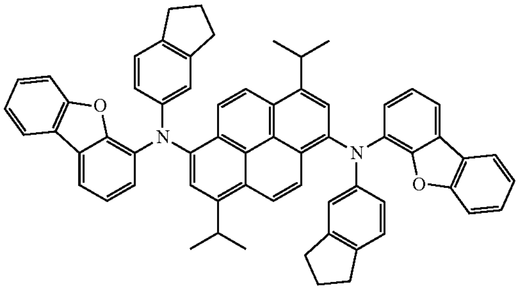
D-80
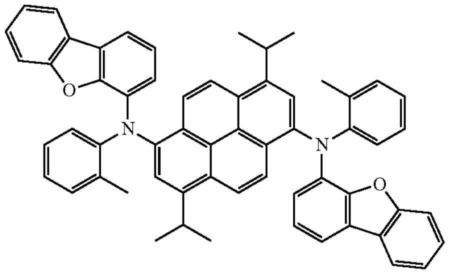
D-81
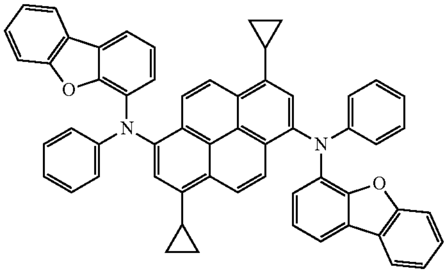
D-82
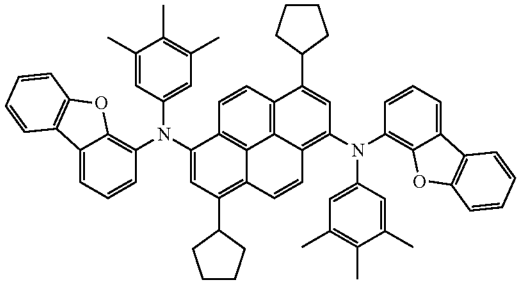
D-83
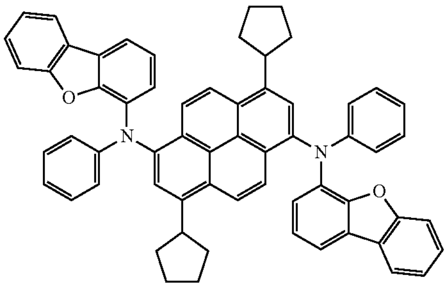
D-84
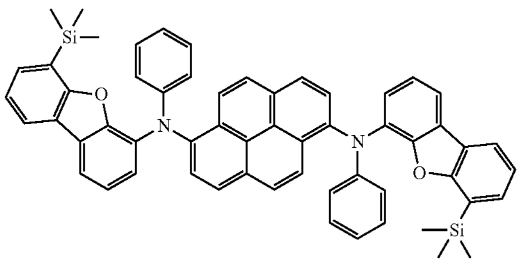
D-85
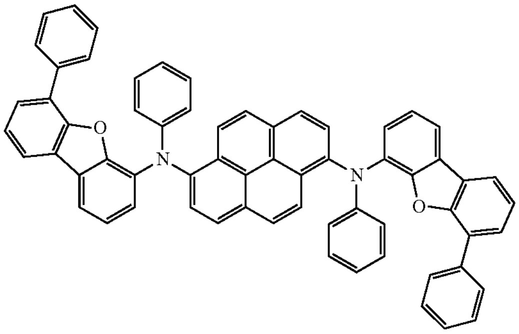
D-86
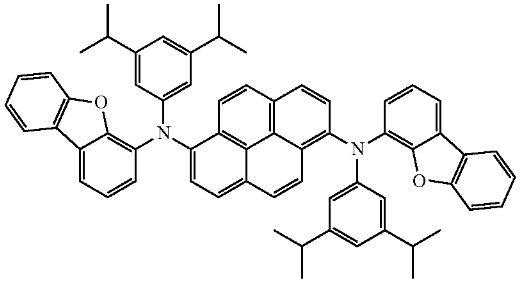

-continued
D-87
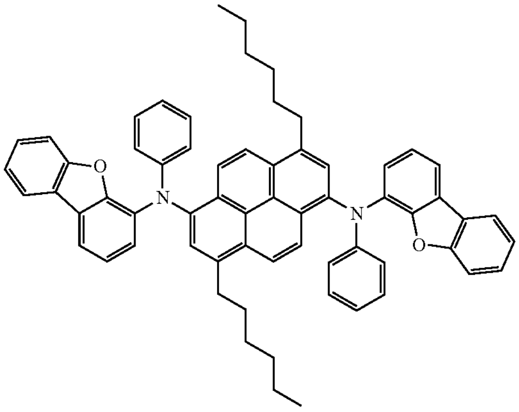
D-88
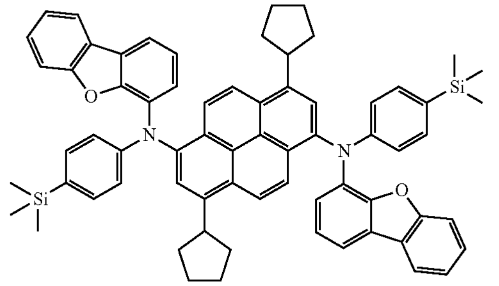
D-89
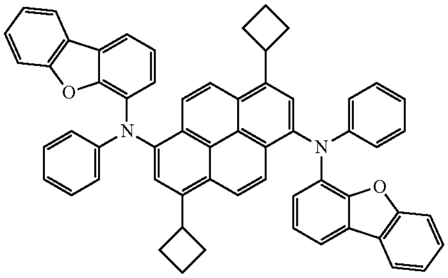
D-90
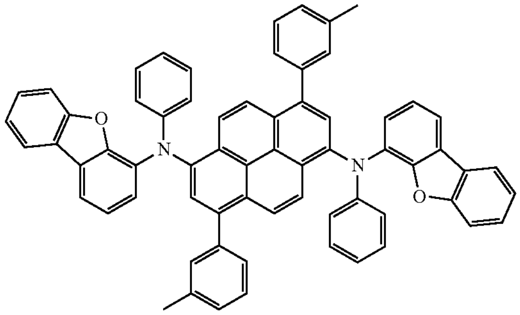
D-91
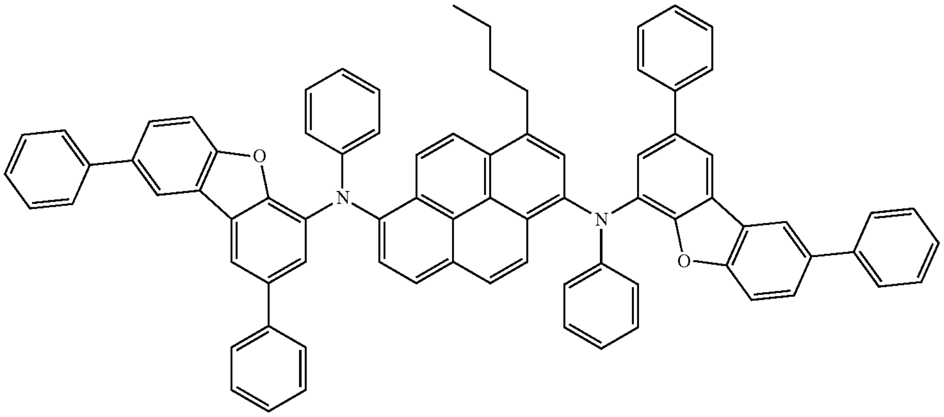
D-92
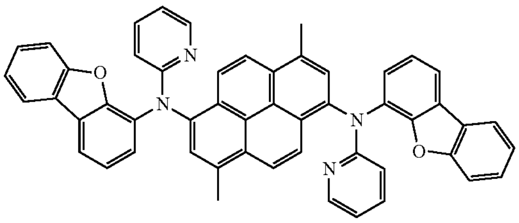
D-93
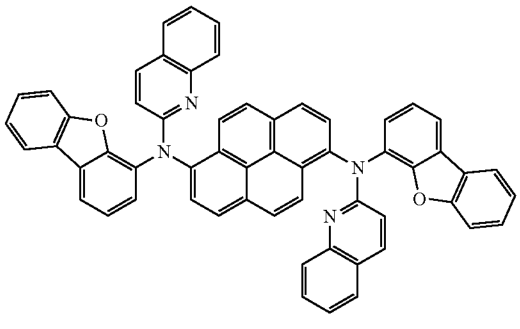

-continued
D-94
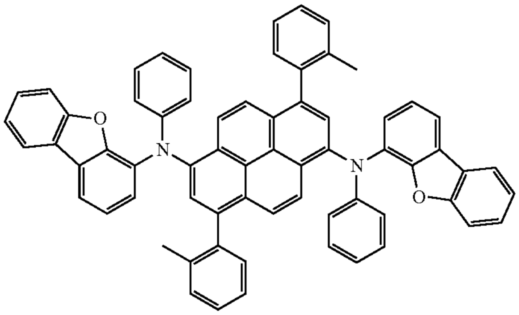
D-95
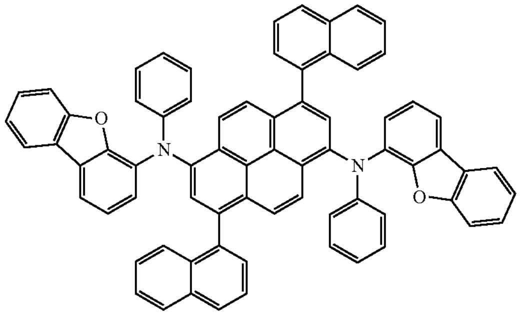
D-96
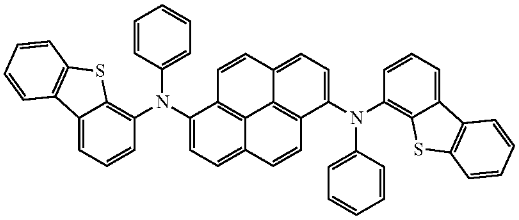
D-97
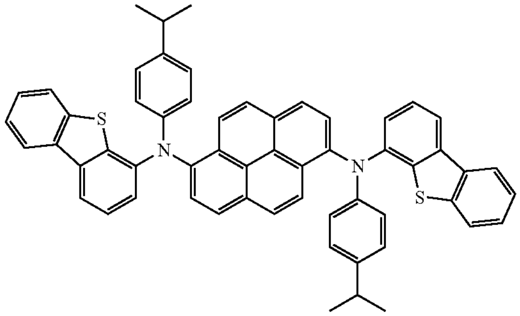
D-98
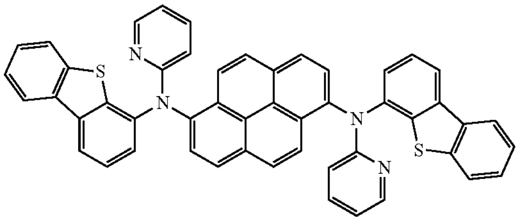
D-99
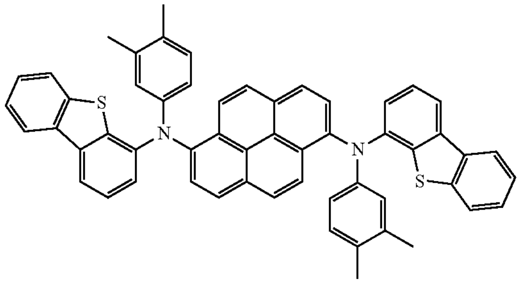
D-100
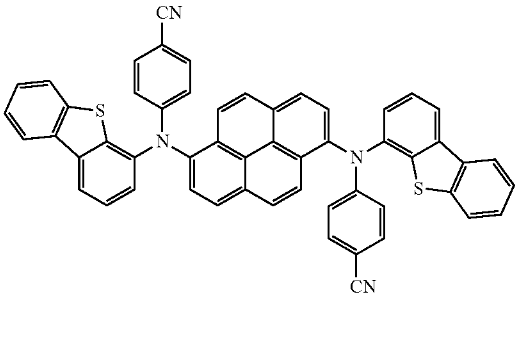
D-101
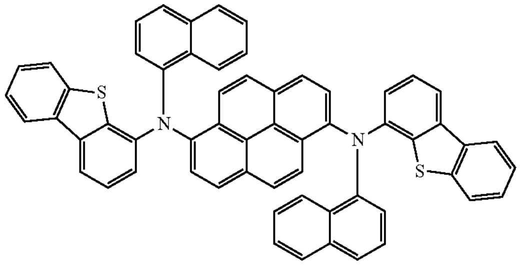

-continued
D-102
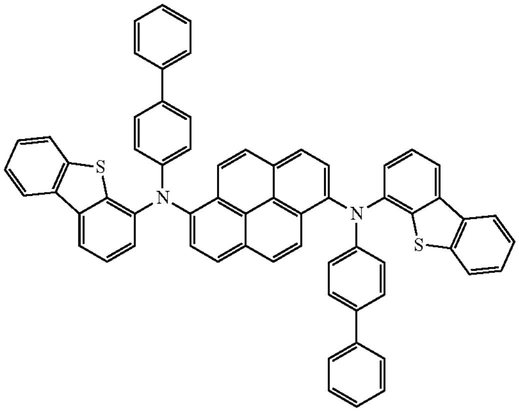
D-103
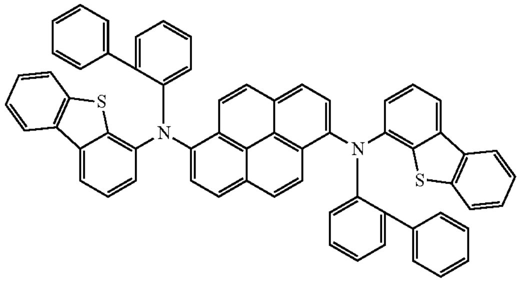
D-104
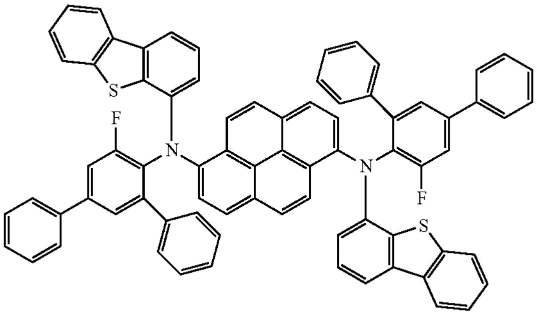
D-105
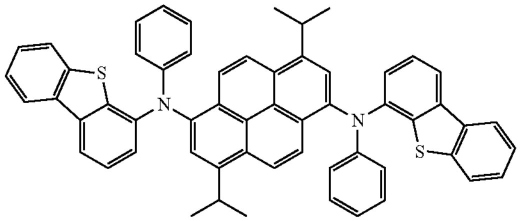
D-106
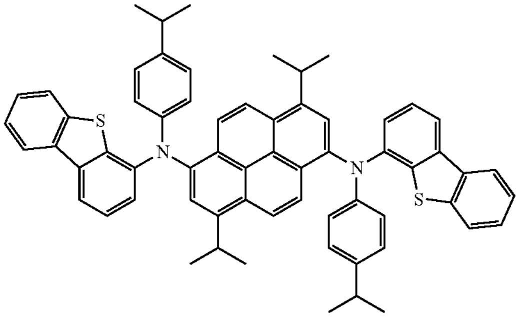
D-107
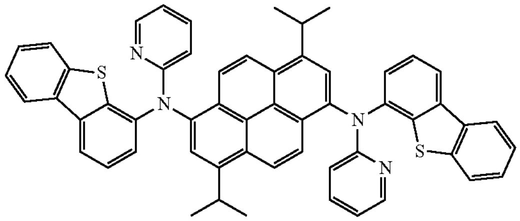
D-108
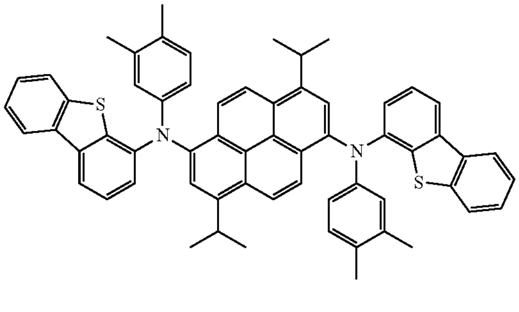
D-109
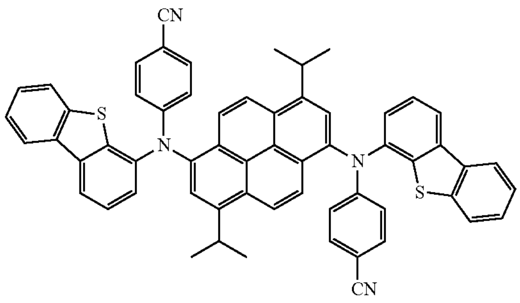

-continued

D-110

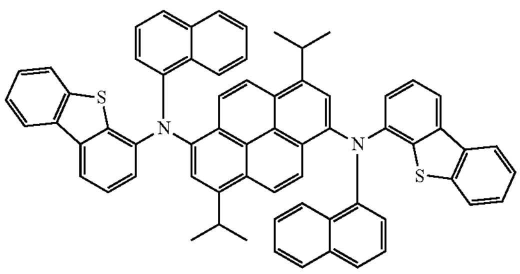

D-111

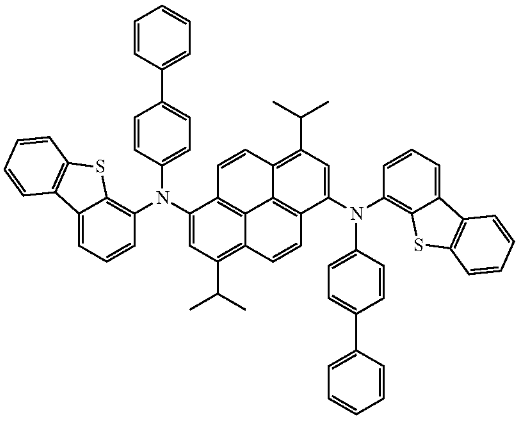

D-112

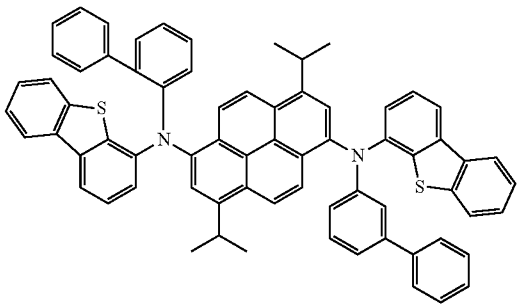

D-113

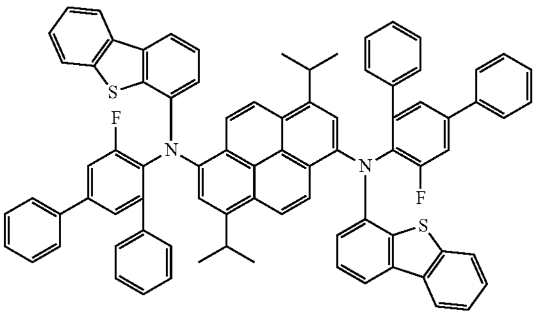

The above-mentioned aromatic amine derivatives can be used as an emitting material for an organic electroluminescence device. It can be used as a dopant, for example.

The organic electroluminescence device of the invention comprises one or more organic thin film layers comprising an emitting layer between an anode and a cathode, wherein at least one layer of the organic thin film layers comprises the above-mentioned aromatic amine derivative singly or as a component of a mixture.

It is preferred that the emitting layer comprise the aromatic amine derivative. The emitting layer may be formed only of the aromatic amine derivative or may contain the aromatic amine derivative as a host or a dopant.

In the organic electroluminescence device of the invention, it is preferred that at least one layer of the organic thin film layers contain the above-mentioned aromatic amine derivative and at least one of an anthracene derivative represented by the following formula (5) and a pyrene derivative represented by the following formula (6). It is preferred that the emitting layer contain the aromatic amine derivative as a dopant and the anthracene derivative as a host.

(Anthracene Derivative)

The anthracene derivative represented by the formula (5) is the following compound.

(5)

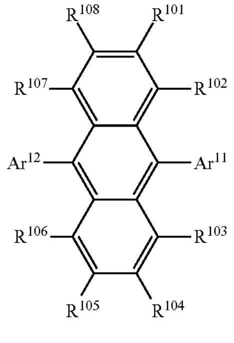

In the formula (5), $Ar^{11}$ and $Ar^{12}$ are independently a substituted or unsubstituted monocyclic group having 5 to 50 ring atoms, a substituted or unsubstituted fused ring group having 8 to 50 ring atoms, or a group formed by combination of a monocyclic group and a fused ring group and $R^{101}$ to $R^{108}$ are independently a group selected from a hydrogen atom, a substituted or unsubstituted monocyclic group having 5 to 50 ring atoms, a substituted or unsubstituted fused ring group having 8 to 50 ring atoms, a group formed by combination of a monocyclic group and a fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom and a cyano group.

The monocyclic group in the formula (5) means a group which is composed only of ring structures having no fused structure.

As specific examples of the monocyclic group having 5 to 50 (preferably 5 to 30, more preferably 5 to 20) ring atoms, aromatic groups such as a phenyl group, biphenyl group, terphenyl group and quaterphenyl group, and heterocyclic groups such as a pyridyl group, pyradyl group, pyrimidyl group, triadinyl group, furyl group and thienyl group, can be given preferably.

Among these, a phenyl group, biphenyl group or terphenyl group is preferable.

The fused ring group in the formula (5) means a group formed by fusion of 2 or more ring structures.

As specific examples of the fused ring group having 8 to 50 (preferably 8 to 30, more preferably 8 to 20) ring atoms, fused aromatic ring groups such as a naphthyl group, phenanthryl group, anthryl group, chrysenyl group, benzanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group and benzofluoranthenyl group, and fused heterocyclic groups such as a benzofuranyl group, benzothiophenyl group, indolyl group, dibenzofuranyl group, dibenzothiophenyl group, carbazolyl group, quinolyl group and phenanthrolinyl group, can be given preferably.

Among these, a naphthyl group, phenanthryl group, anthryl group, 9,9-dimethylfluorenyl group, fluoranthenyl group, benzanthryl group, dibenzothiophenyl group, dibenzofuranyl group or carbazolyl group is preferable.

Specific examples of the alkyl group, silyl group, alkoxy group, aryloxy group, aralkyl group, cycloalkyl group and halogen atom in the formula (5) are the same as the specific examples of the group represented by $R_1$ to $R_8$, $R_{11}$ to $R_{17}$, $R_{21}$ to $R_{27}$, $R_{31}$ to $R_{37}$, $R_{41}$ to $R_{48}$ and $Ar_1$ to $Ar_4$ in the formulas (1) to (4) and the specific examples of the substituent of the "substituted or unsubstituted . . . ". Only preferable specific examples in the formula (5) are given below.

As preferable substituents of "substituted or unsubstituted . . . " in $Ar^{11}$, $Ar^{12}$, and $R^{101}$ to $R^{108}$, a monocyclic group, fused ring group, alkyl group, cycloalkyl group, silyl group, alkoxy group, cyano group and halogen atom (in particular, fluorine) can be given. A monocyclic group and fused ring group are particularly preferable. The preferable specific substituents are the same as those described in the formula (5) and those described in the formulas (1) to (4).

It is preferred that the anthracene derivative represented by the formula (5) be any of the following anthracene derivatives (A), (B) and (C), which is selected depending on the constitution or demanded properties of an organic EL device to which it is applied.

(Anthracene Derivative (A))

This anthracene derivative is derivatives of the formula (5) wherein $Ar^{11}$ and $Ar^{12}$ are independently a substituted or unsubstituted fused ring group having 8 to 50 ring atoms. This anthracene derivative can be classified into the case that $Ar^{11}$ and $Ar^{12}$ are the same substituted or unsubstituted fused ring group and the case that $Ar^{11}$ and $Ar^{12}$ are different substituted or unsubstituted fused ring groups.

Particularly preferred is the anthracene derivative of the formula (5) wherein $Ar^{11}$ and $Ar^{12}$ are different (including difference in substituted positions) substituted or unsubstituted fused ring groups. Preferable specific examples of the fused ring are the same as those described above. Among those, a naphthyl group, phenanthryl group, benzanthryl group, 9,9-dimethylfluorenyl group and dibenzofuranyl group are preferable.

(Anthracene Derivative (B))

This anthracene derivative is derivatives of the formula (5) wherein one of $Ar^{11}$ and $Ar^{12}$ is a substituted or unsubstituted monocyclic group having 5 to 50 ring atoms, and the other is a substituted or unsubstituted fused ring group having 8 to 50 ring atoms.

As a preferred embodiment, $Ar^{12}$ is a naphthyl group, phenanthryl group, benzanthryl group, 9,9-dimethylfluorenyl group or dibenzofuranyl group, and $Ar^{11}$ is a phenyl group substituted by a monocyclic group or fused ring group.

Preferable specific examples of the monocyclic group and fused ring group are the same as those described above.

As another preferred embodiment, $Ar^{12}$ is a fused ring group, and $A^{11}$ is an unsubstituted phenyl group. In this case, as the fused ring group, a phenanthryl group, 9,9-dimethylfluorenyl group, dibenzofuranyl group and benzoanthryl group are particularly preferable.

(Anthracene Derivative (C))

This anthracene derivative is derivatives of formula (5) wherein $Ar^{11}$ and $Ar^{12}$ are independently a substituted or unsubstituted monocyclic group having 5 to 50 ring atoms.

As a preferred embodiment, both $Ar^{11}$ and $Ar^{12}$ are a substituted or unsubstituted phenyl group.

As a further preferred embodiment, $Ar^{11}$ is an unsubstituted phenyl group, and $Ar^{12}$ is a phenyl group having a monocyclic group or a fused ring group as a substituent, and $Ar^{11}$ and $Ar^{12}$ are independently a phenyl group having a monocyclic group or a fused ring group as a substituent.

The preferable specific examples of the monocyclic group and fused ring group as a substituent are the same as those described above. As the monocyclic group as a substituent, a phenyl group and biphenyl group are further preferable. As the fused ring group as a substituent, a naphthyl group, phenanthryl group, 9,9-dimethylfluorenyl group, dibenzofuranyl group and benzanthryl group are further preferable.

Specific examples of the anthracene derivatives represented by the formula (5) are given below.

EM1
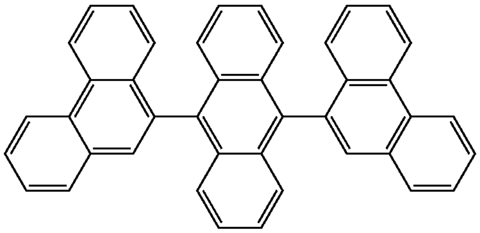
EM2
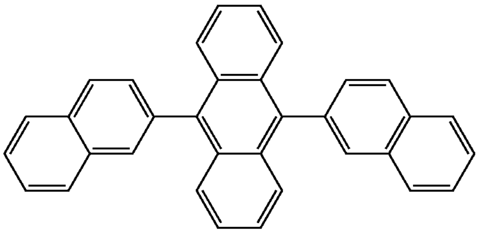
EM3
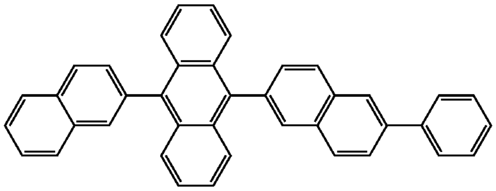
EM4
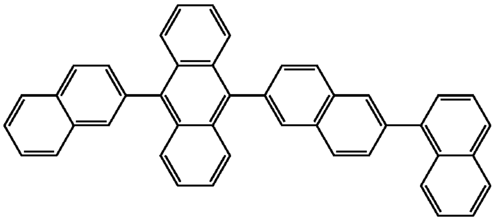
EM5
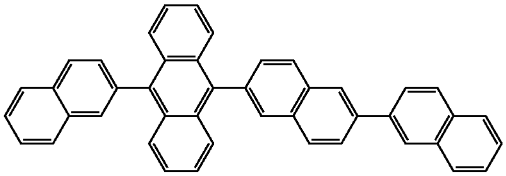
EM6
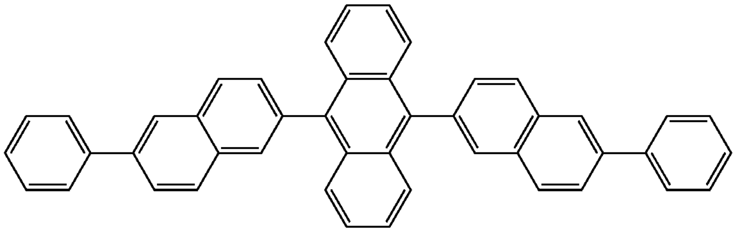
EM7
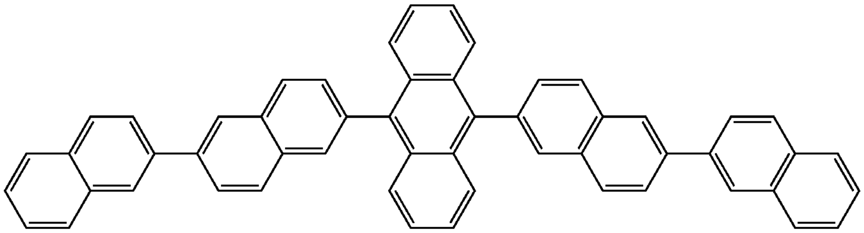
EM8
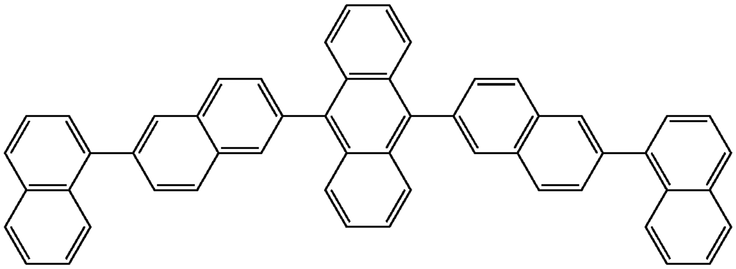

-continued
EM9
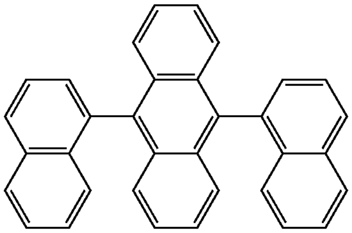
EM10
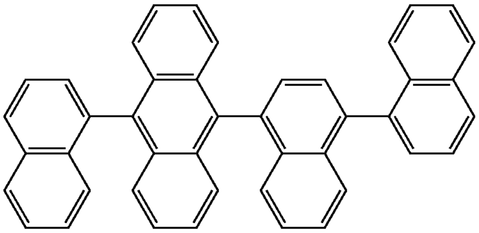
EM11
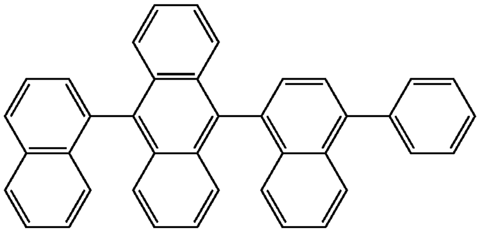
EM12
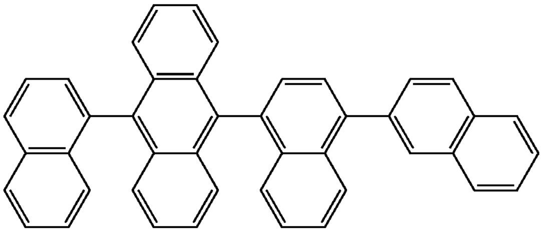
EM13
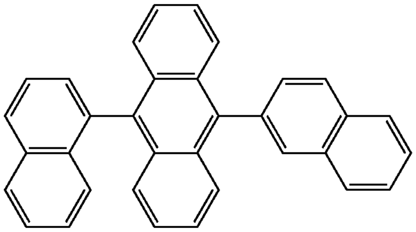
EM14
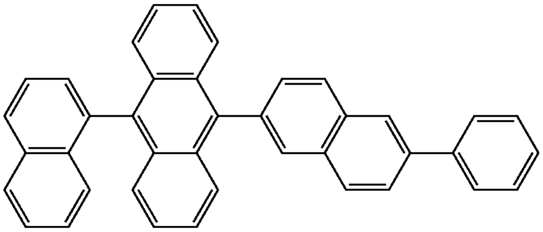
EM15
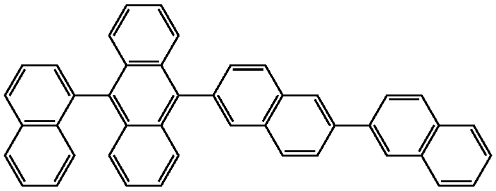
EM16
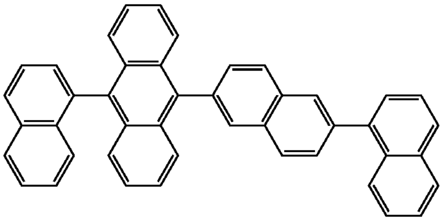
EM17
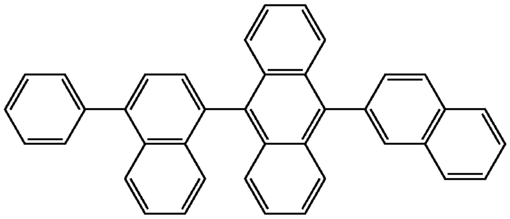
EM18
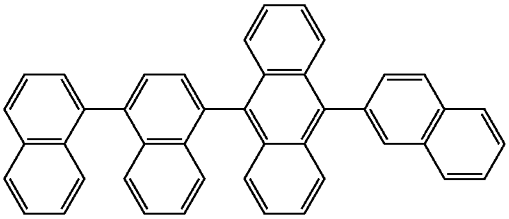
EM19
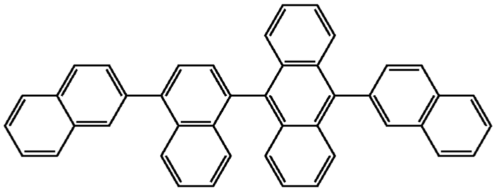
EM20
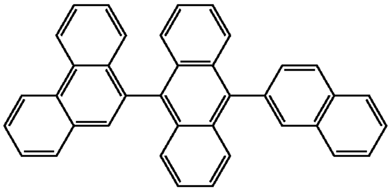

-continued
EM21
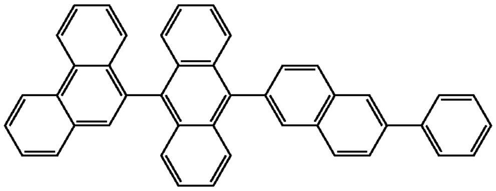
EM22
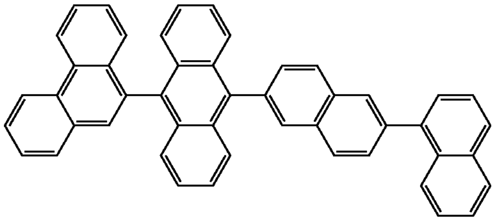
EM23
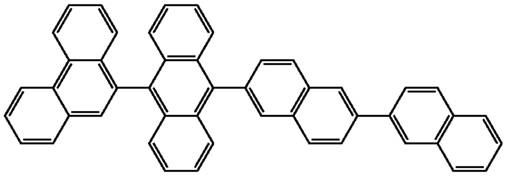
EM24
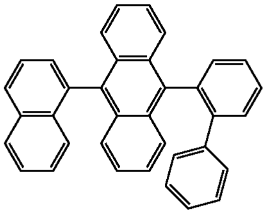
EM25
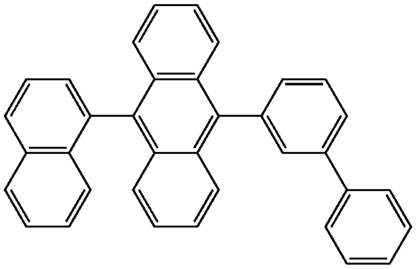
EM26
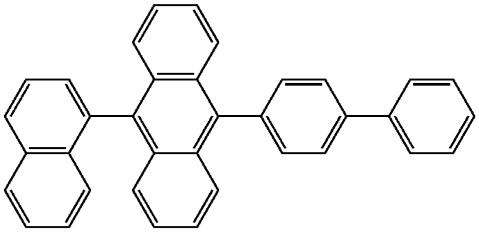
EM27
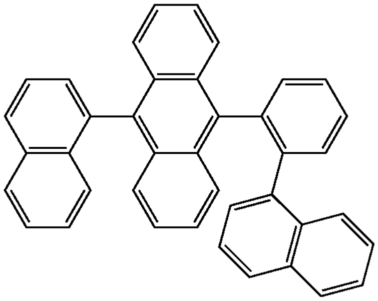
EM28
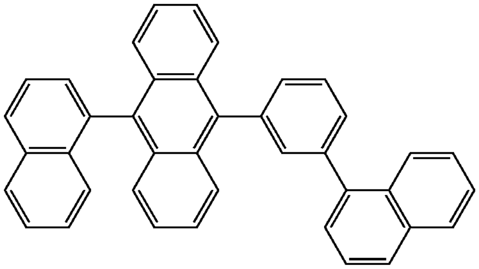
EM29
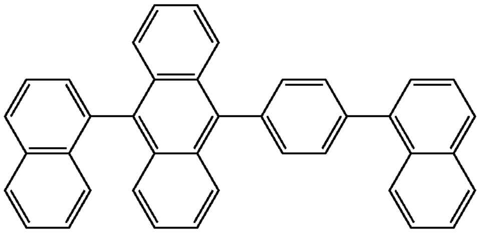
EM30
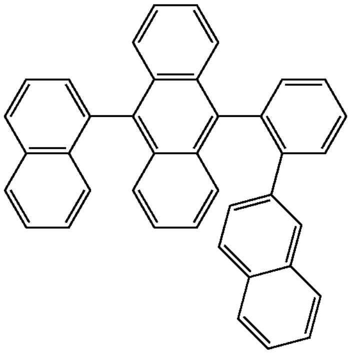

-continued
EM31
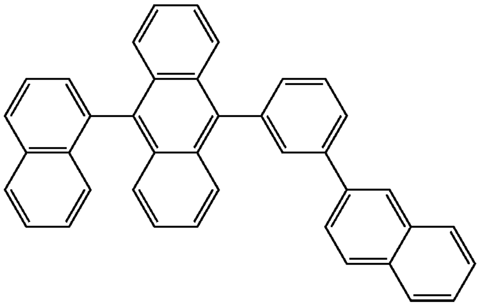
EM32
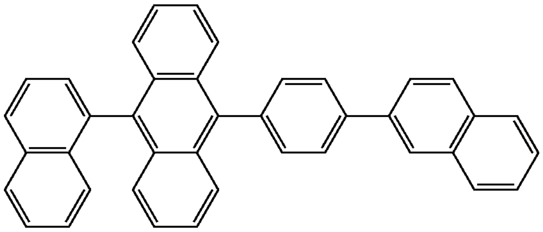
EM33
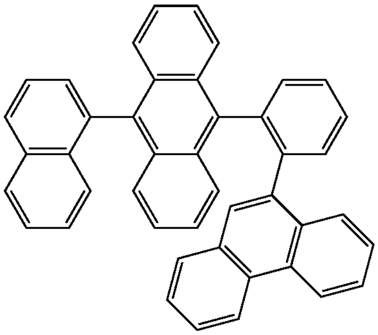
EM34
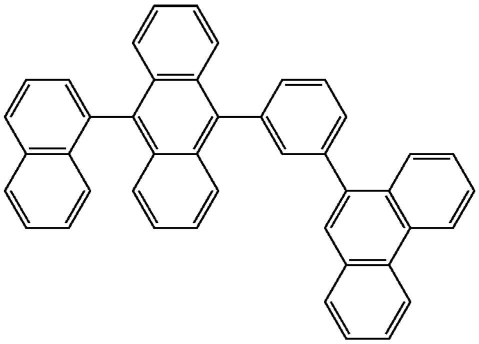
EM35
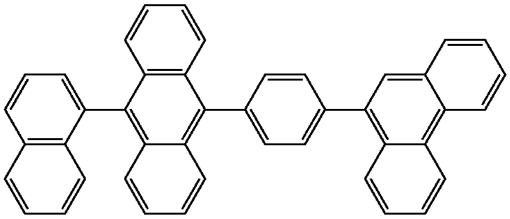
EM36
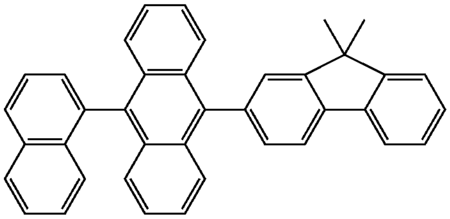
EM37
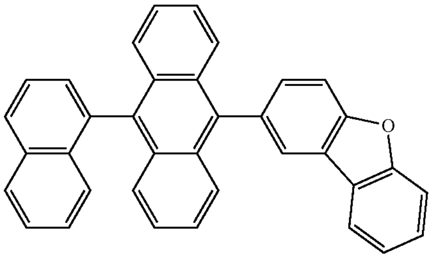
EM38
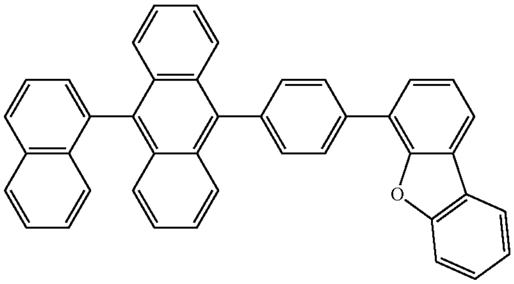
EM39
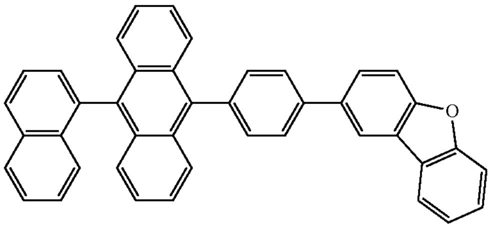
EM40
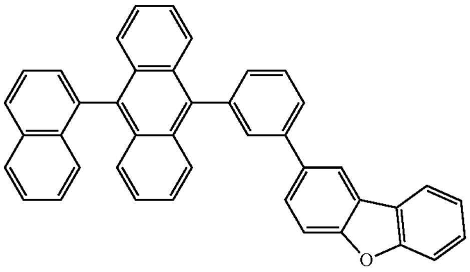

-continued
EM41
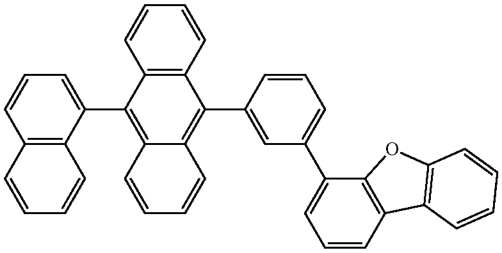
EM42
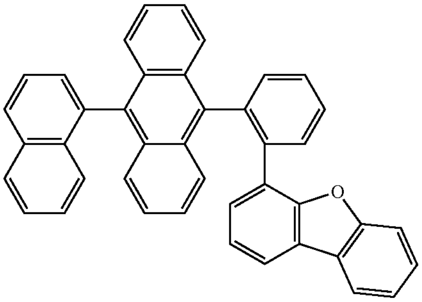
EM43
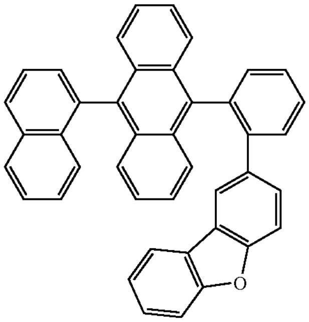
EM44
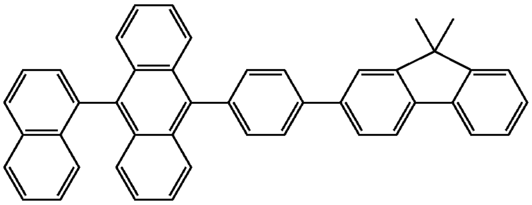
EM45
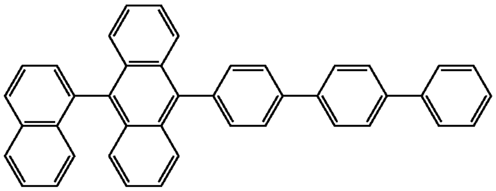
EM46
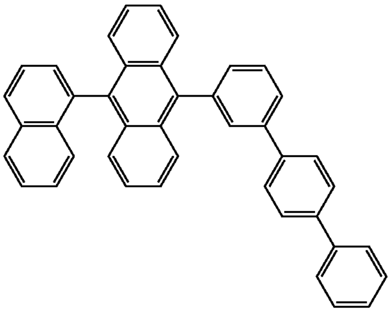
EM47
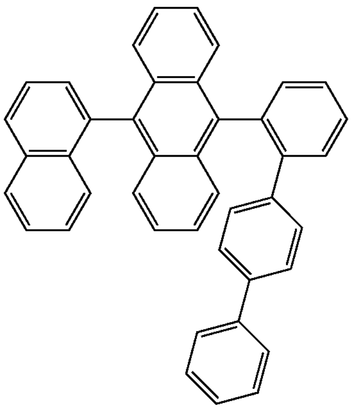
EM48
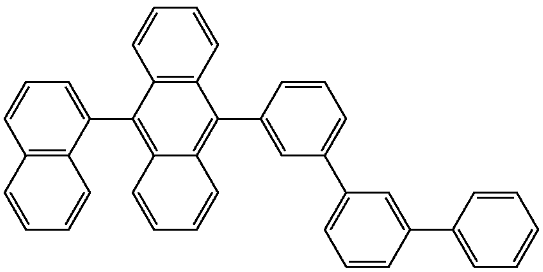

-continued
EM49
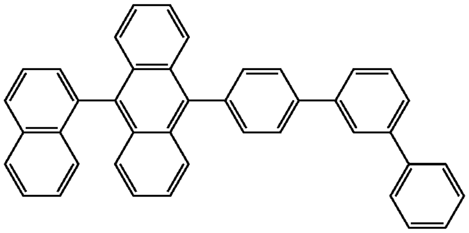
EM50
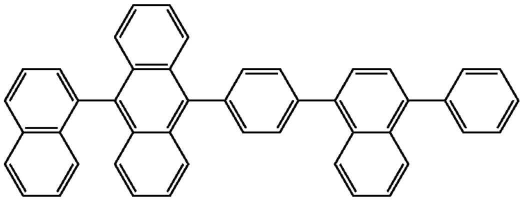
EM51
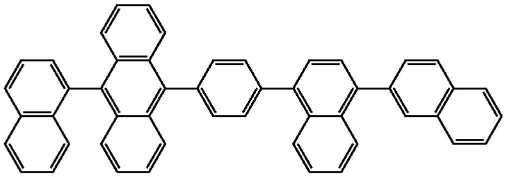
EM52
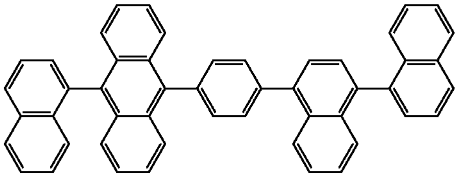
EM53
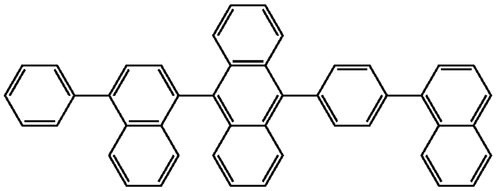
EM54
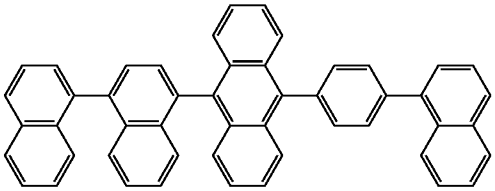
EM55
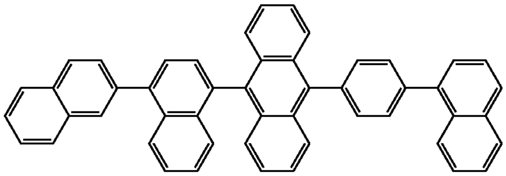
EM56
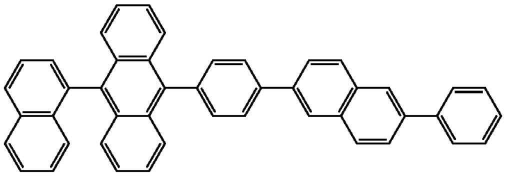
EM57
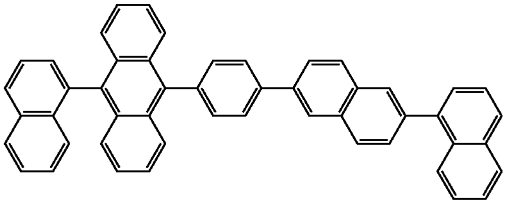
EM58
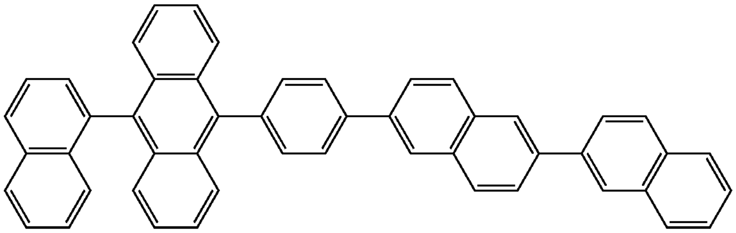

-continued
EM59
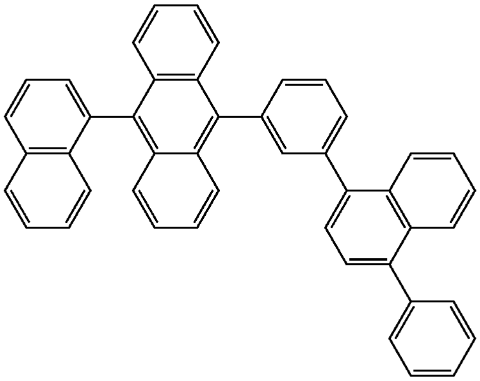
EM60
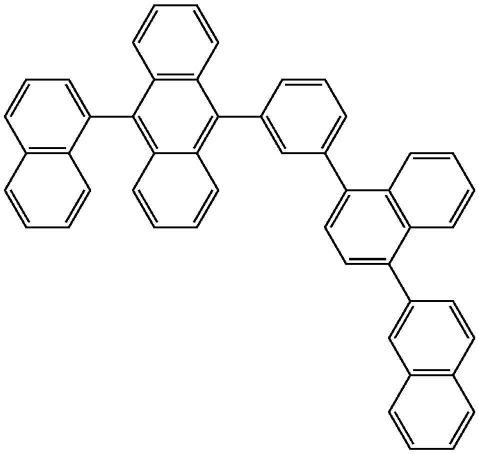
EM61
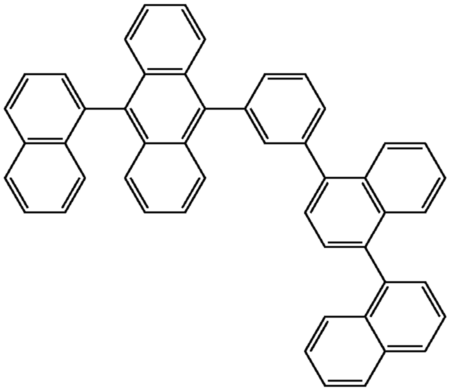
EM62
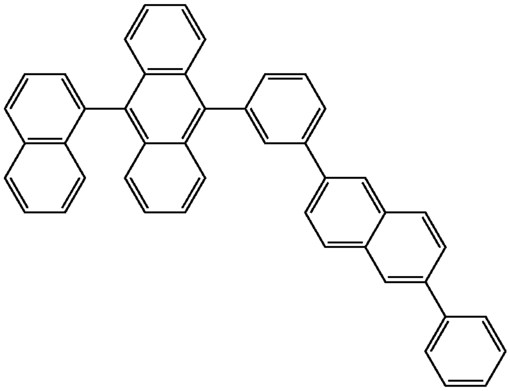
EM63
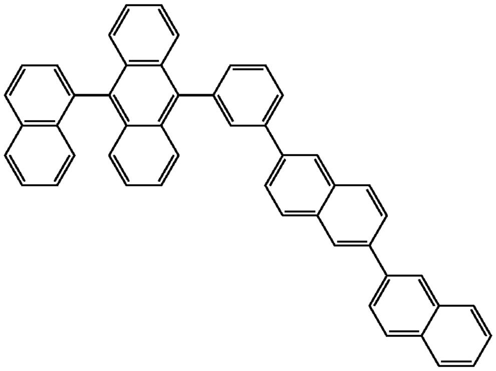
EM64
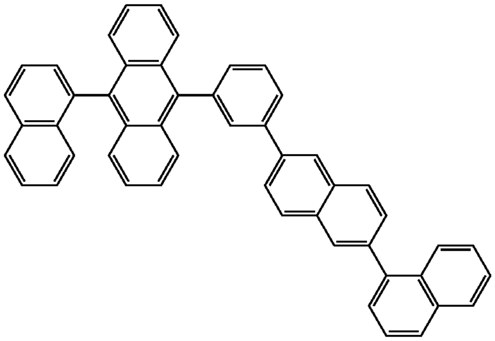
EM65
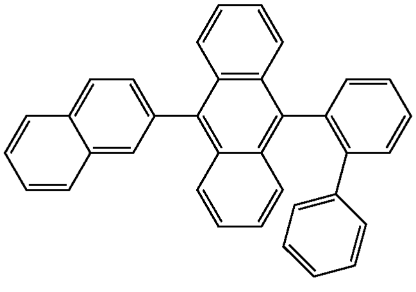
EM66
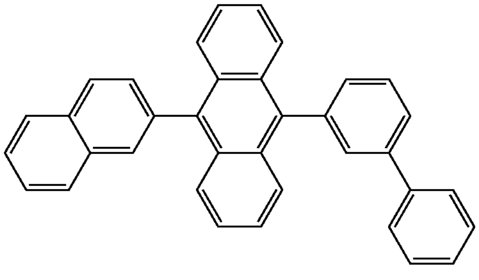

-continued
EM67
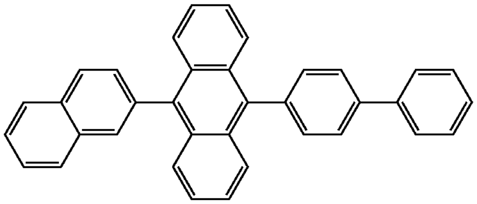
EM68
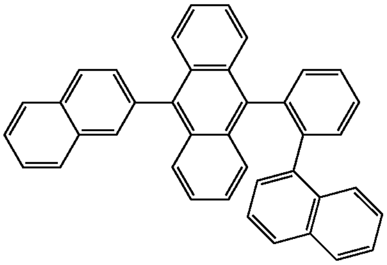
EM69
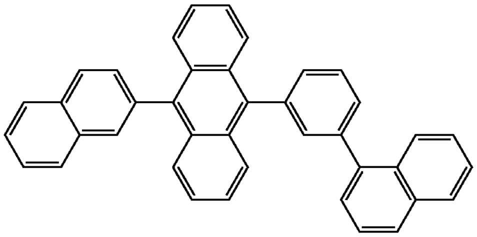
EM70
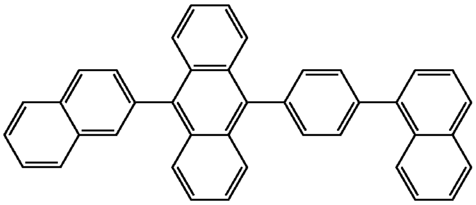
EM71
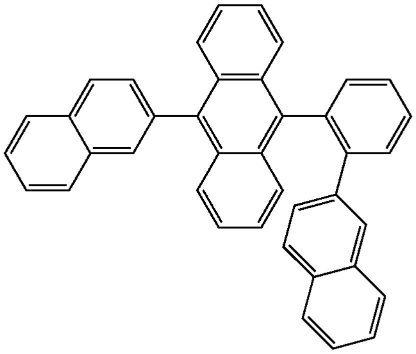
EM72
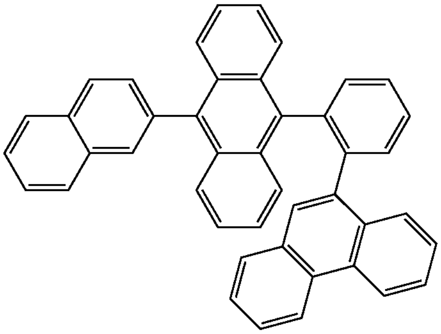
EM73
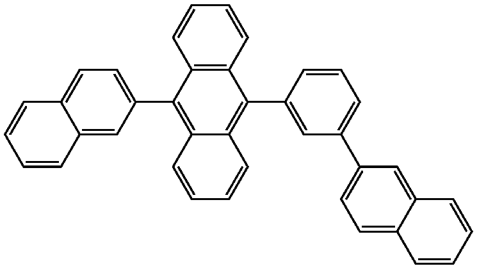
EM74
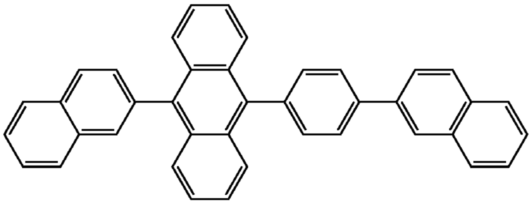
EM75
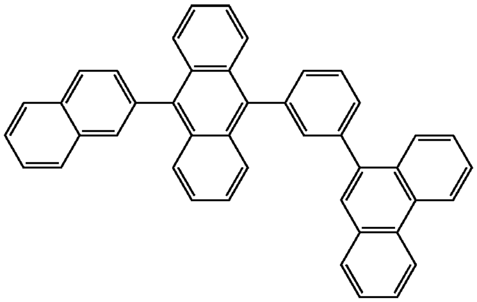
EM76
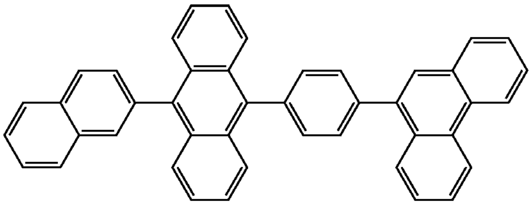

-continued
EM77
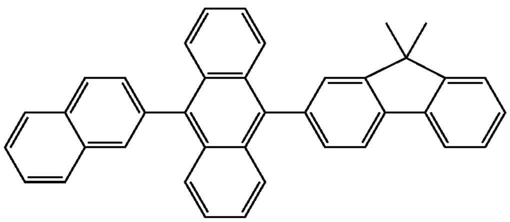
EM78
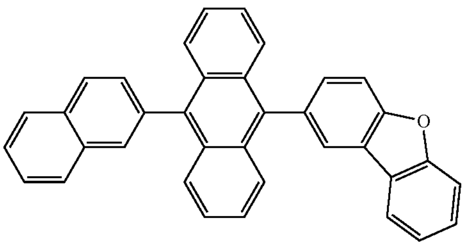
EM79
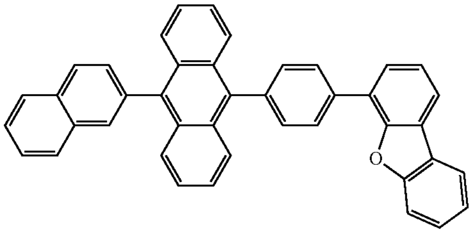
EM80
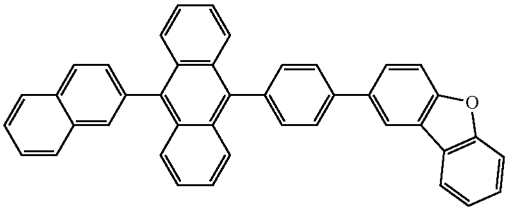
EM81
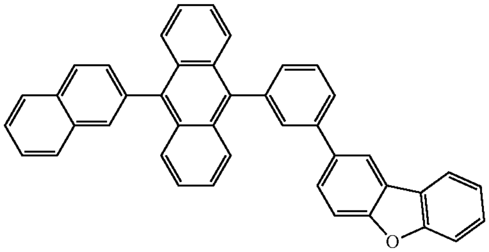
EM82
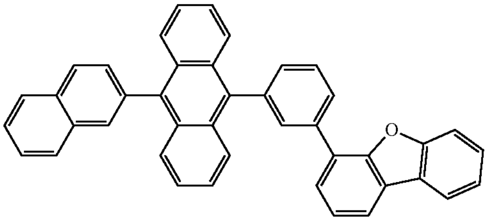
EM83
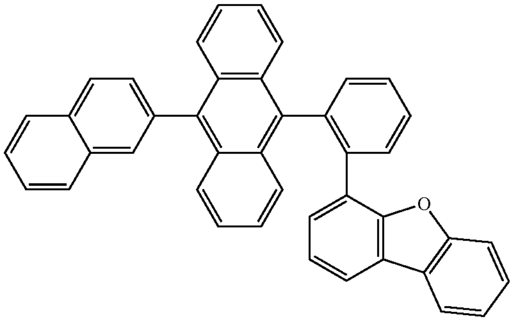
EM84
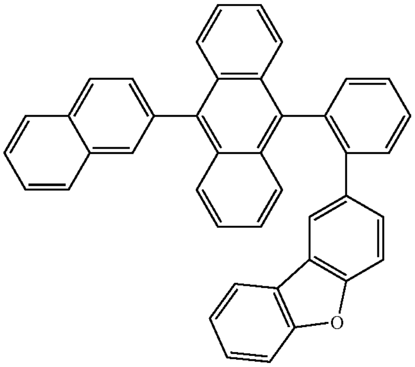
EM85
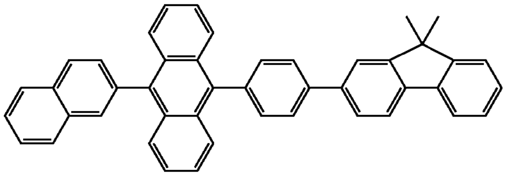
EM86
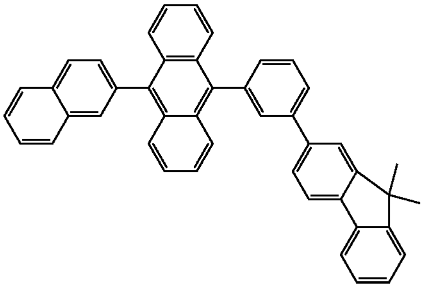

-continued
EM87
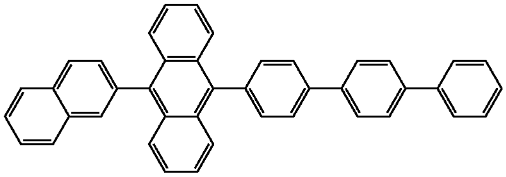
EM88
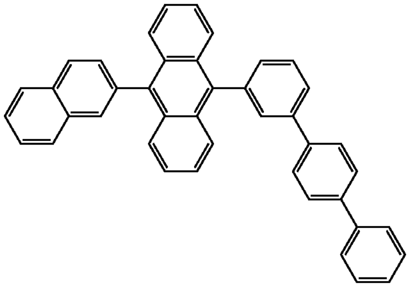
EM89
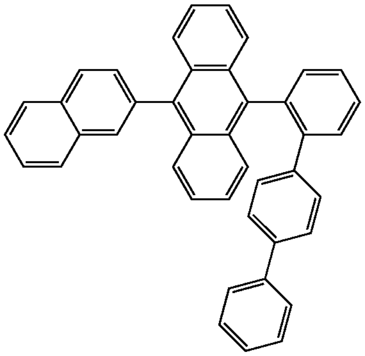
EM90
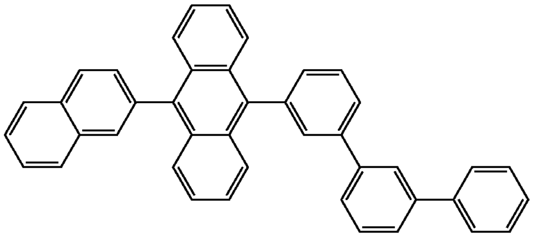
EM91
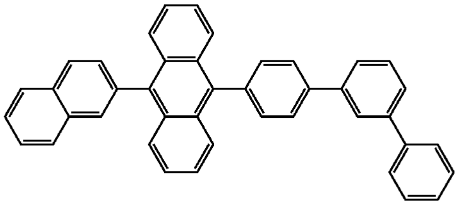
EM92
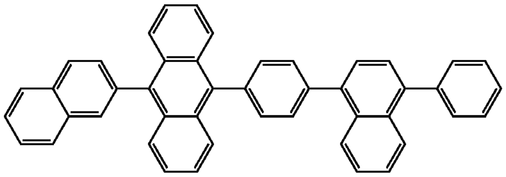
EM93
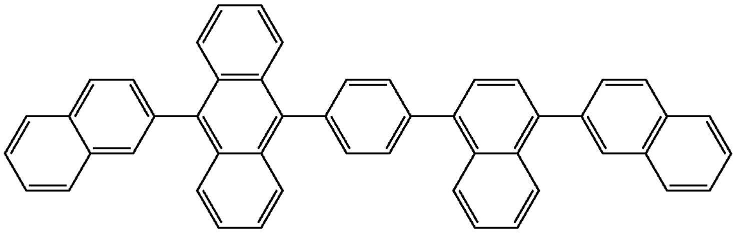
EM94
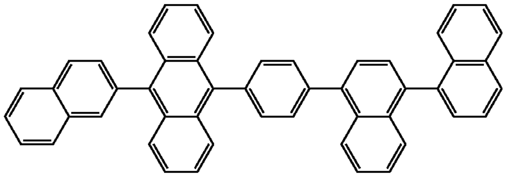
EM95
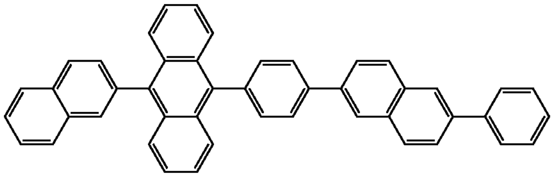
EM96
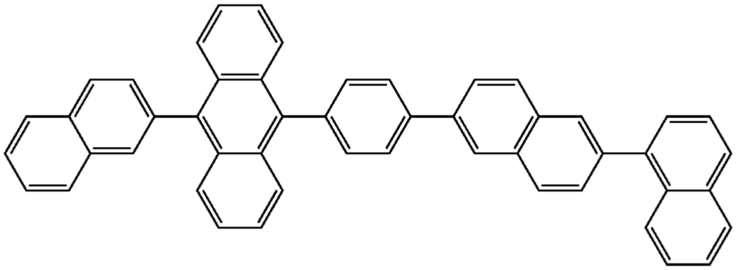

-continued
EM97
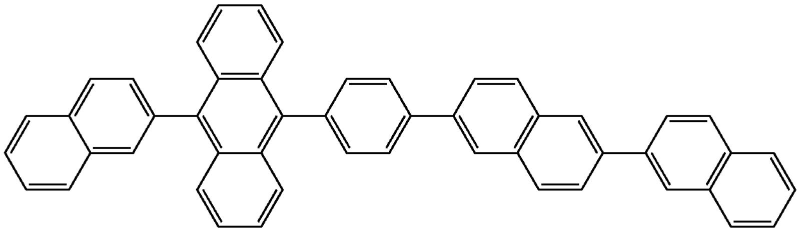
EM98
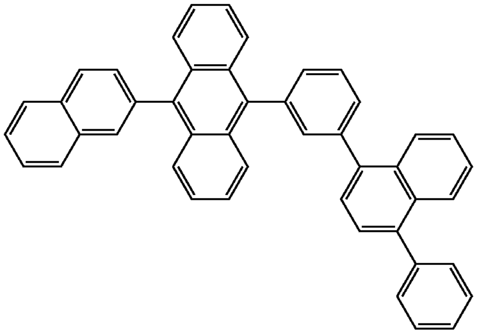
EM99
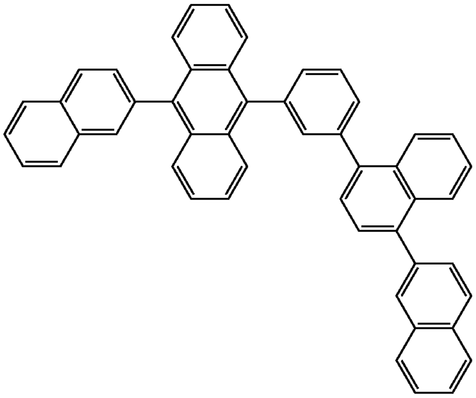
EM100
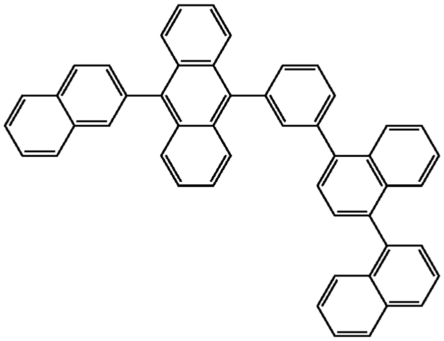
EM101
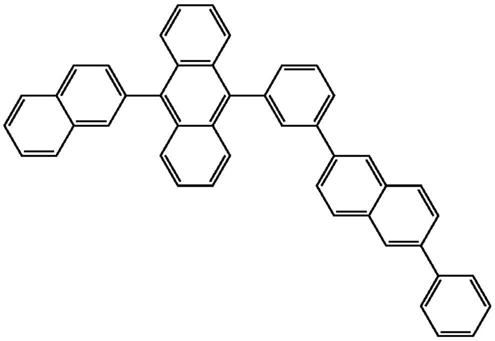
EM102
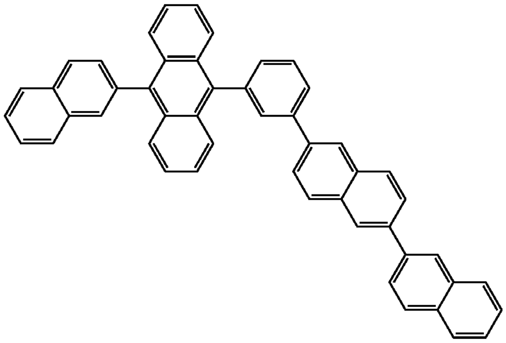
EM103
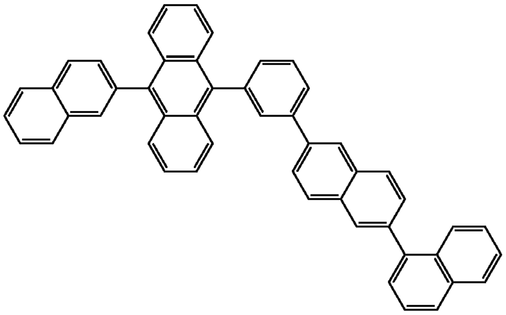
EM104
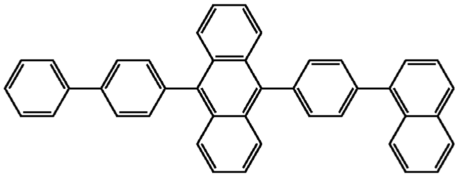
EM105
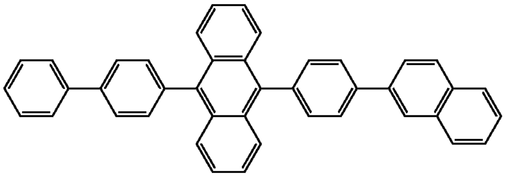

-continued
EM106
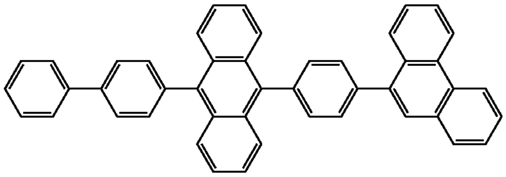
EM107
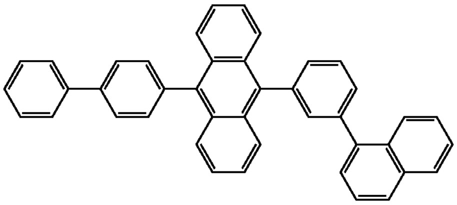
EM108
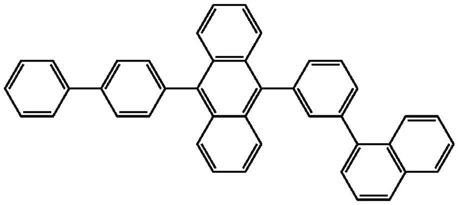
EM109
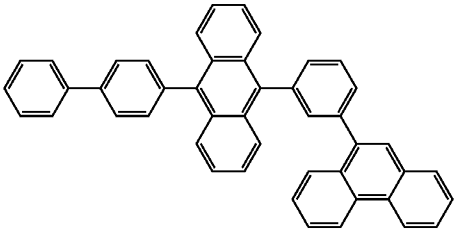
EM110
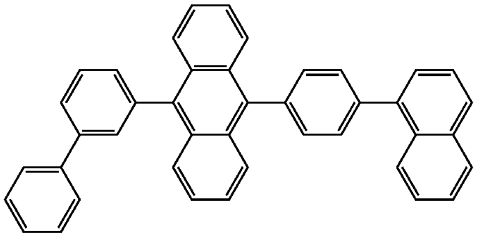
EM111
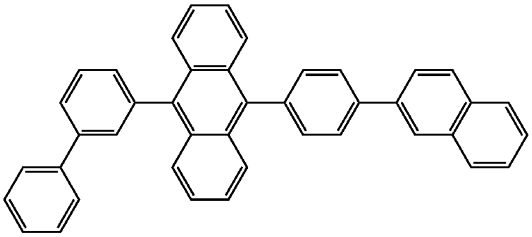
EM112
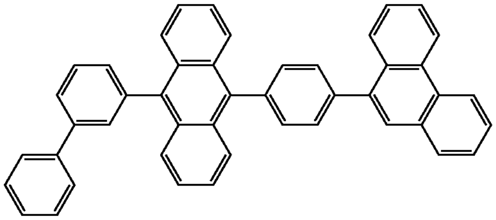
EM113
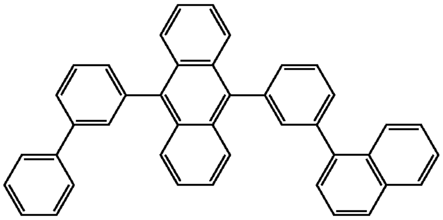
EM114
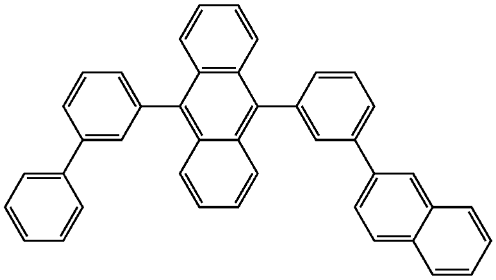
EM115
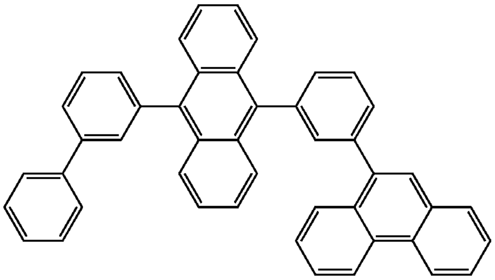
EM116
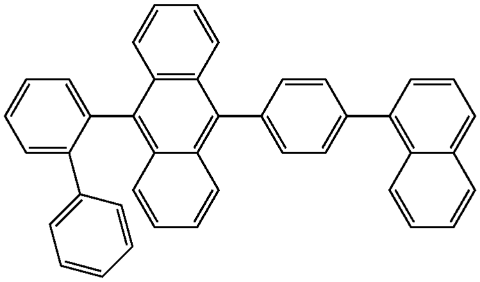
EM117
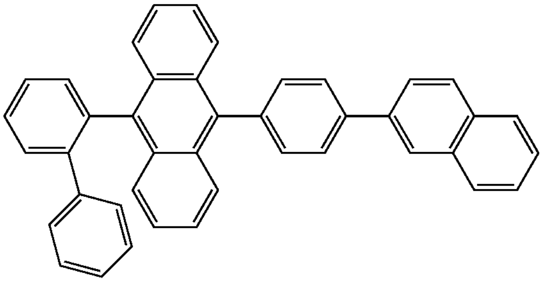

-continued
EM118
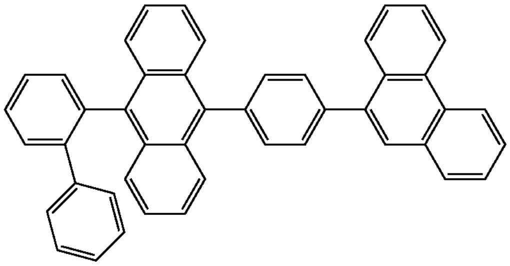
EM119
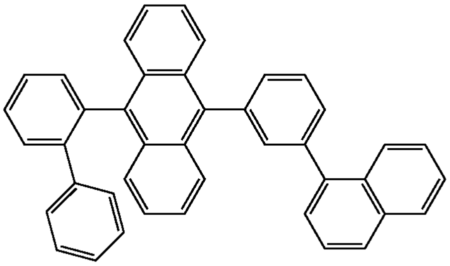
EM120
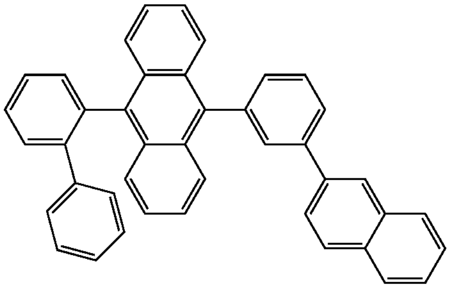
EM121
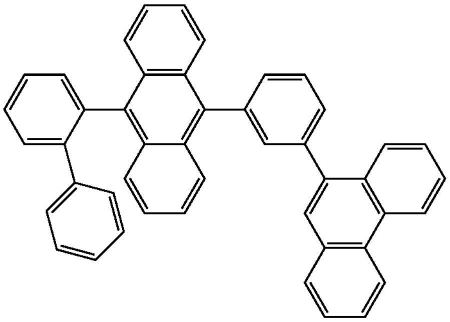
EM122
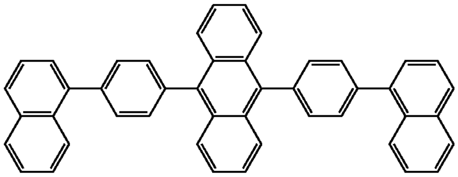
EM123
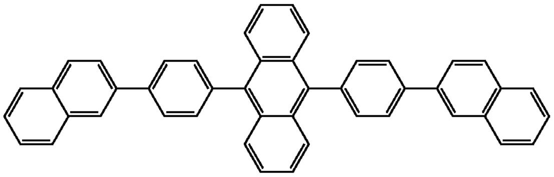
EM124
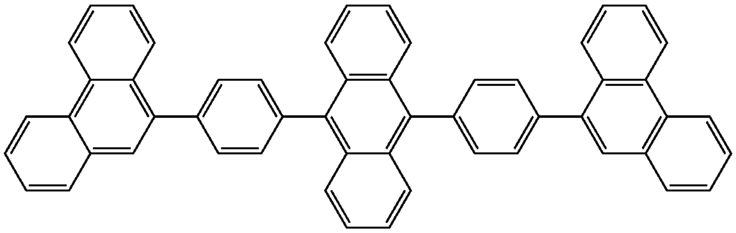
EM125
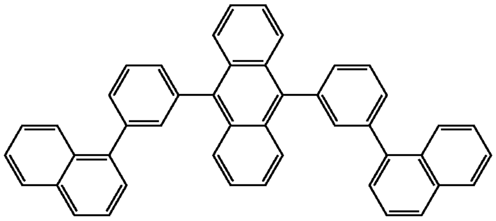
EM126
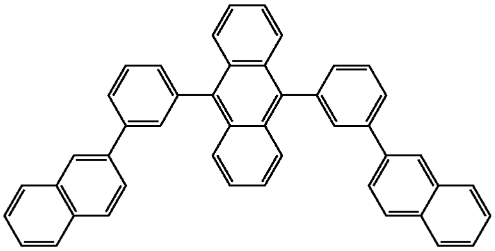
EM127
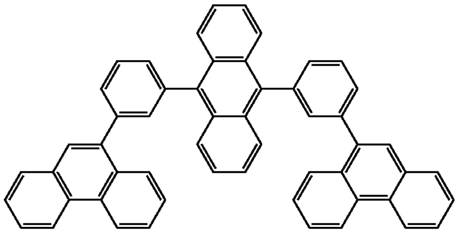
EM128
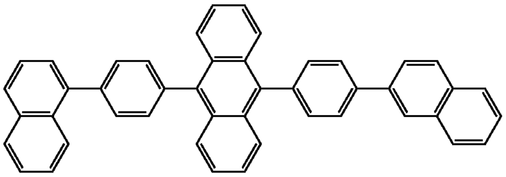

-continued
EM129
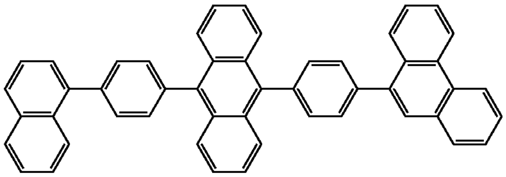
EM130
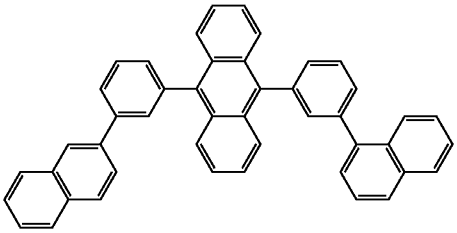
EM131
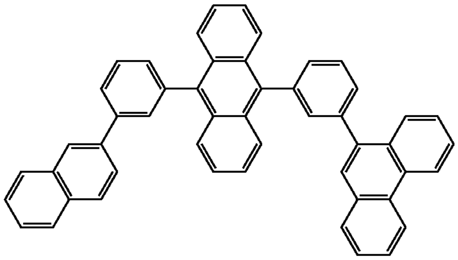
EM132
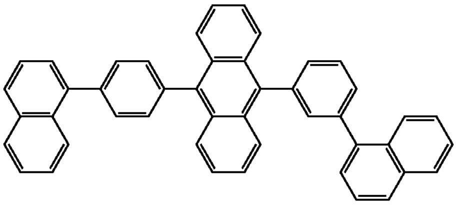
EM133
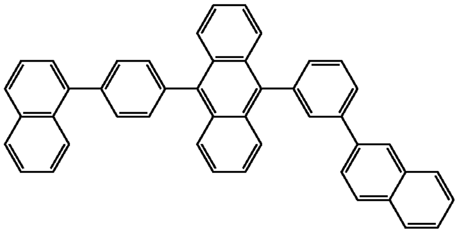
EM134
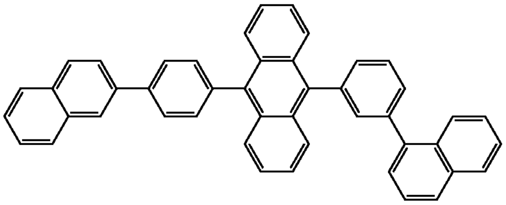
EM135
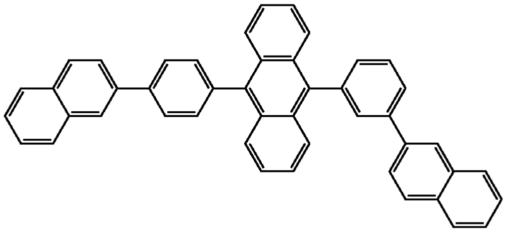
EM136
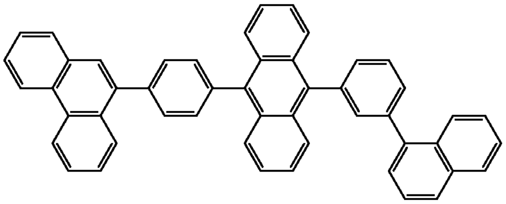
EM137
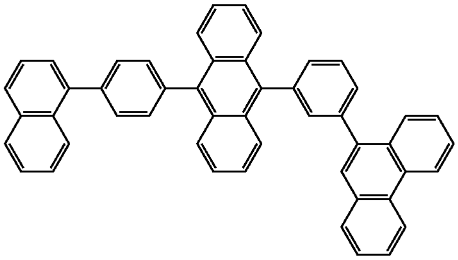
EM138
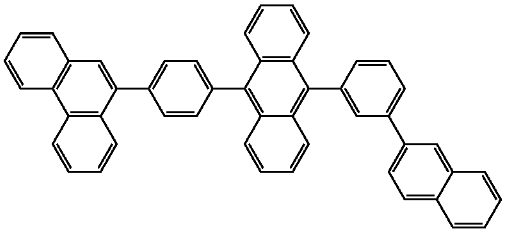
EM139
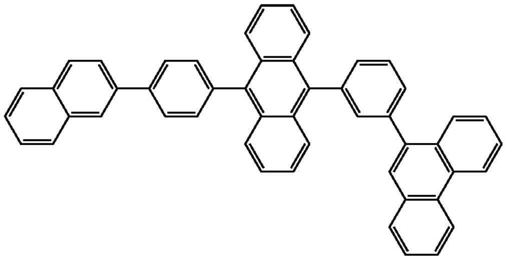
EM140
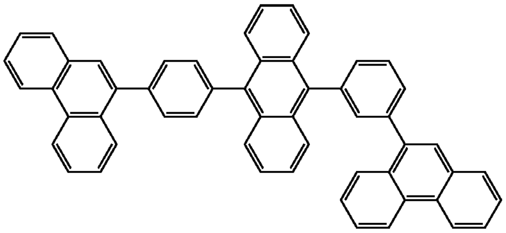

-continued
EM141
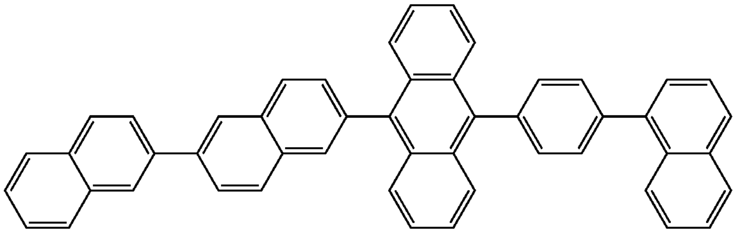
EM142
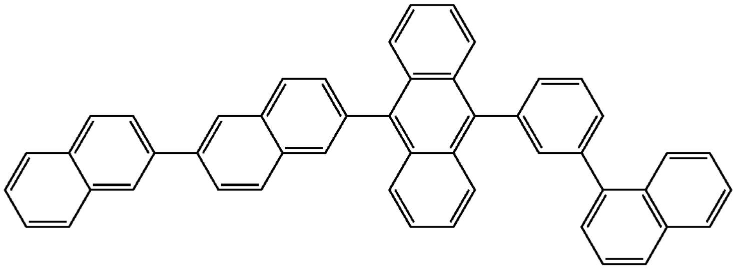
EM143
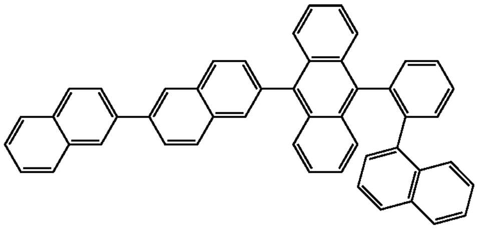
EM144
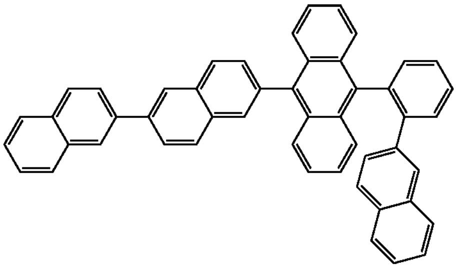
EM145
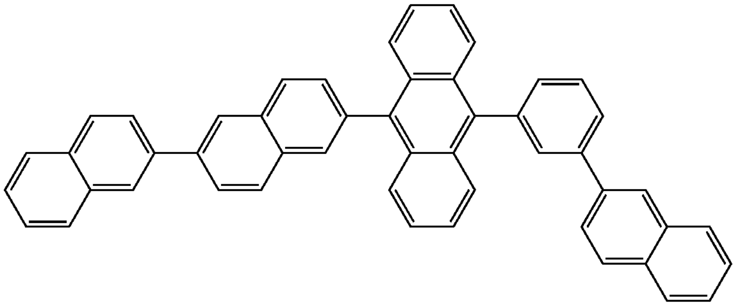
EM146
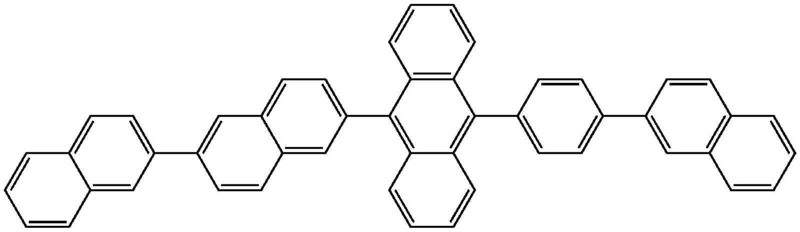
EM147
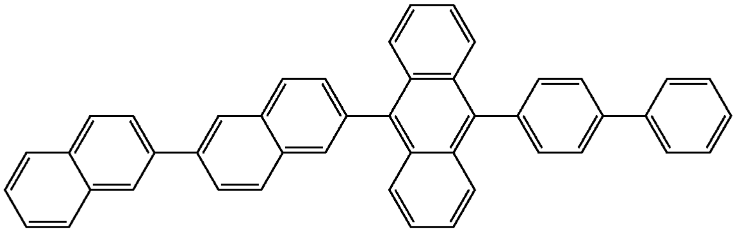

-continued
EM148
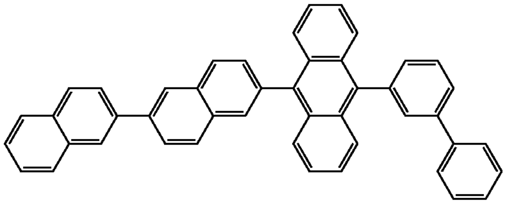
EM149
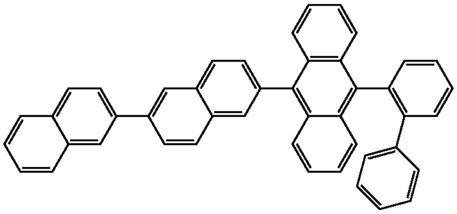
EM150
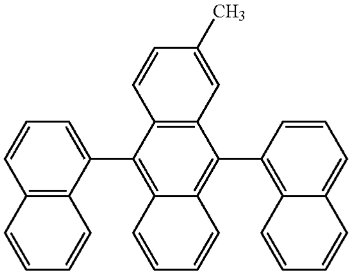
EM151
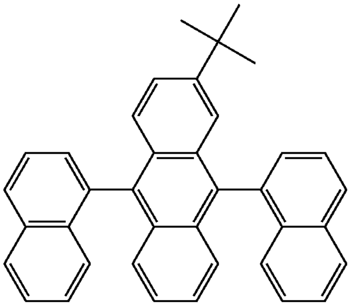
EM152
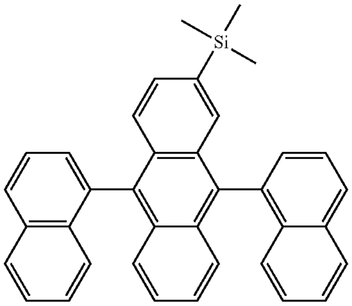
EM153
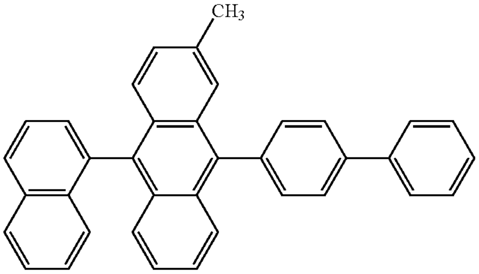
EM154
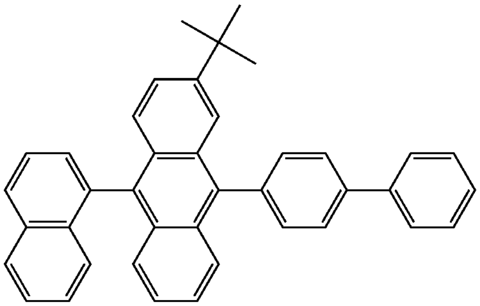
EM155
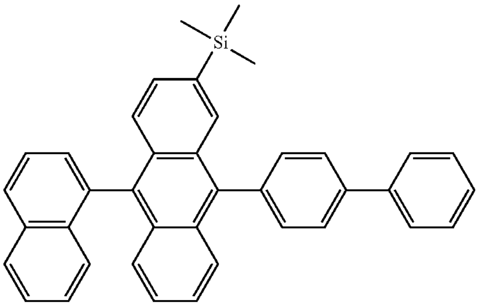
EM156
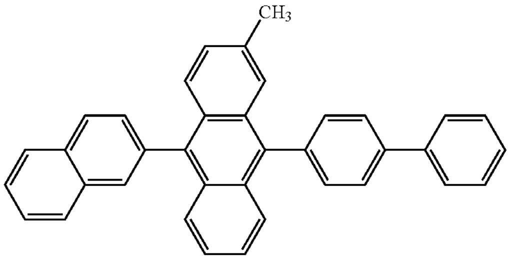
EM157
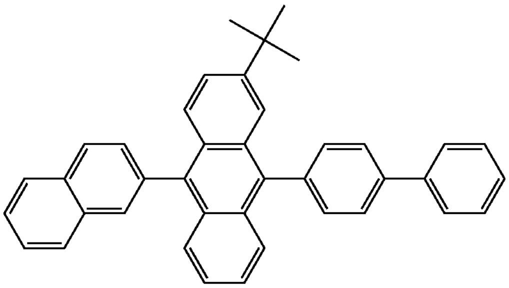

-continued
EM158
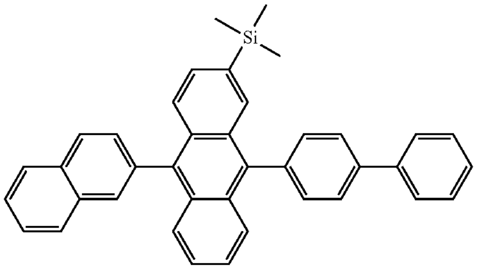
EM159
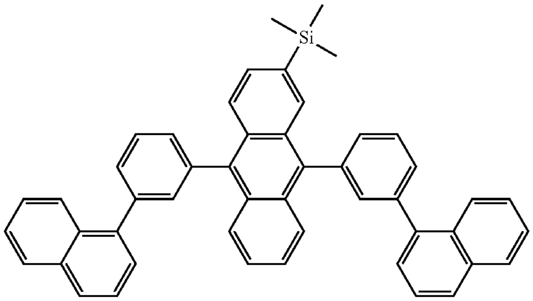
EM160
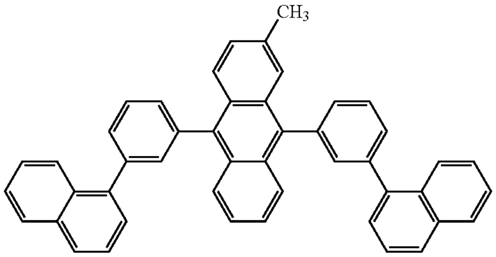
EM161
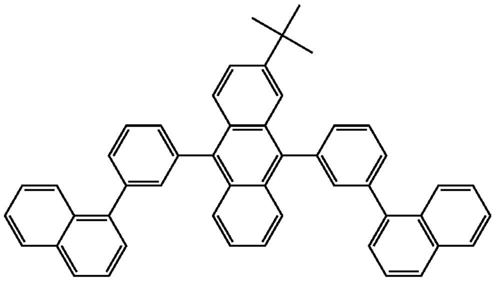
EM162
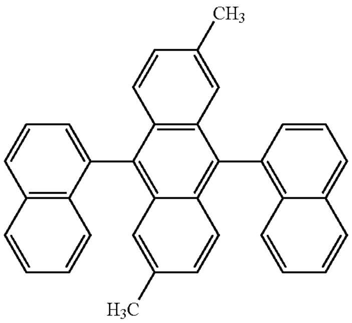
EM163
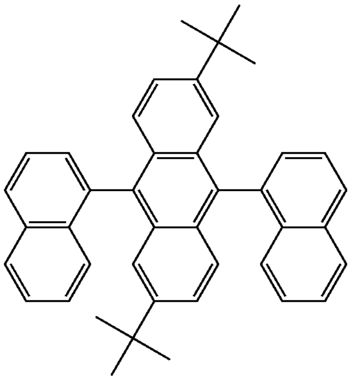
EM164
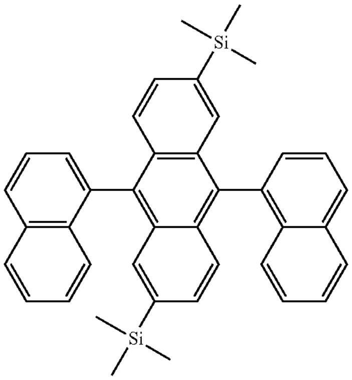
EM165
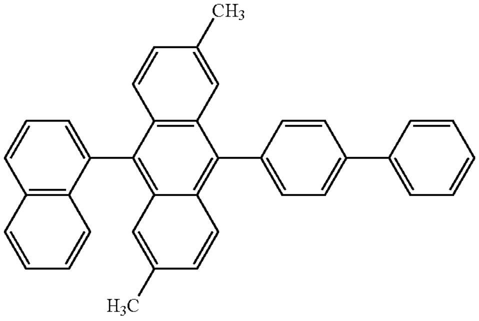

-continued
EM166
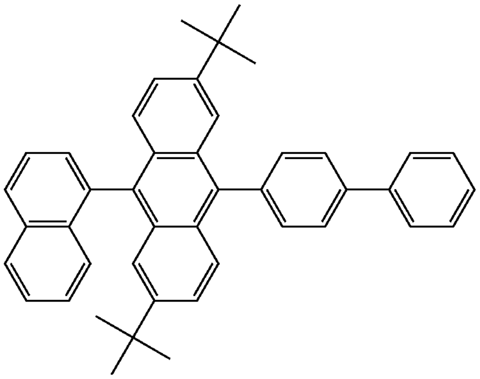
EM167
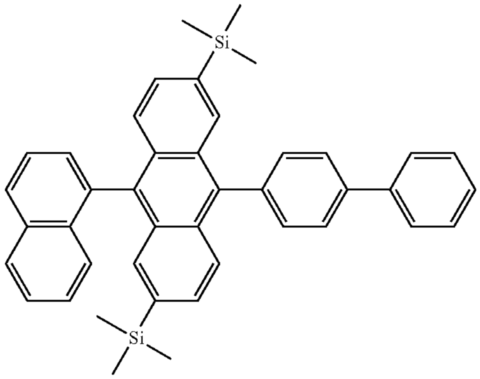
EM168
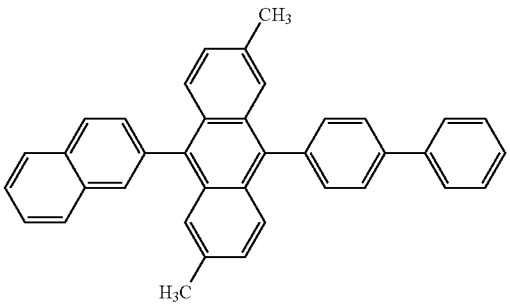
EM169
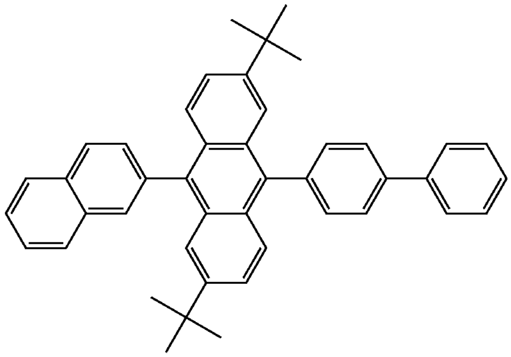
EM170
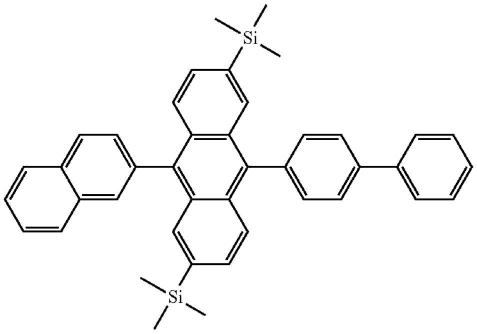
EM171
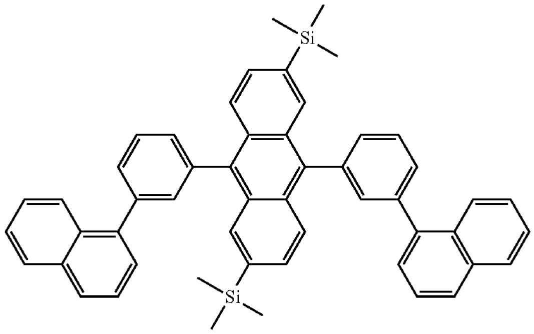
EM172
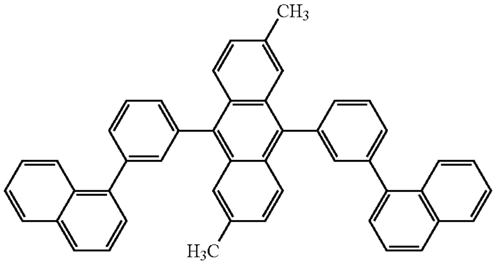
EM173
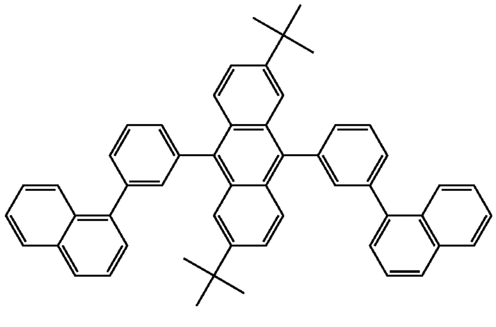

-continued
EM174
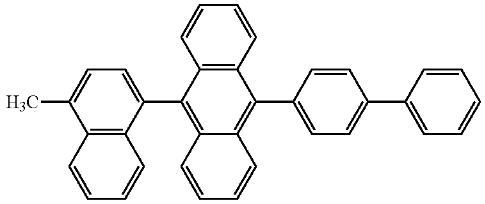
EM175
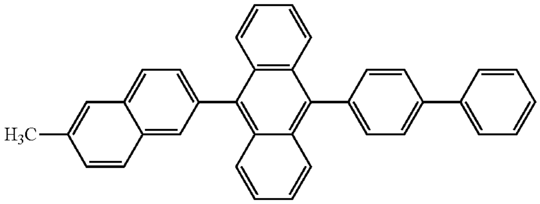
EM176
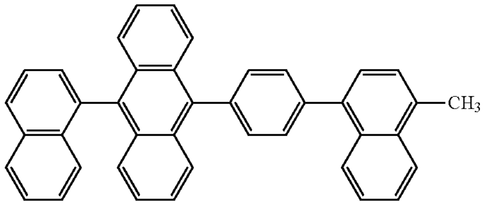
EM177
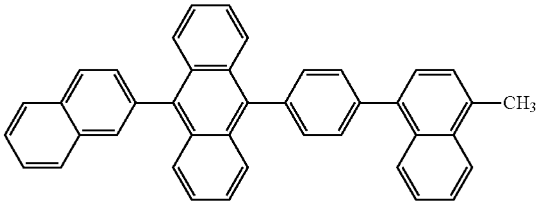
EM178
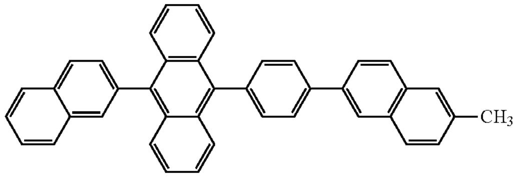
EM179
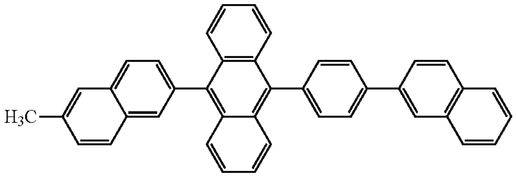
EM180
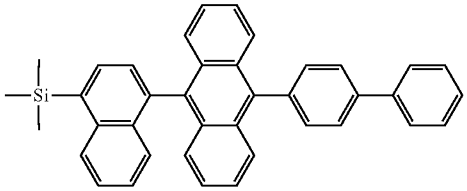
EM181
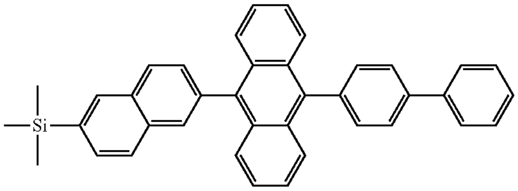
EM182
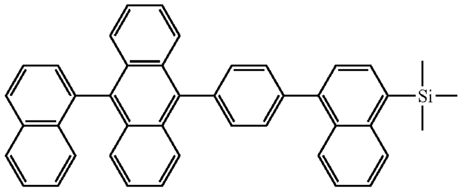
EM183
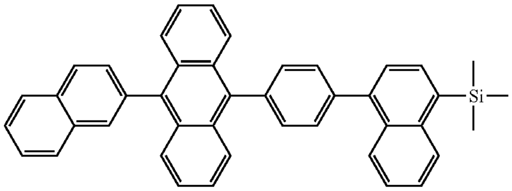
EM184
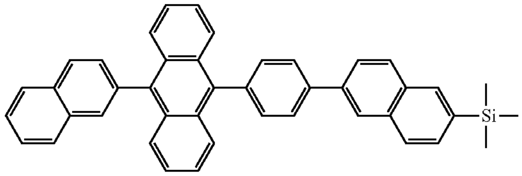
EM185
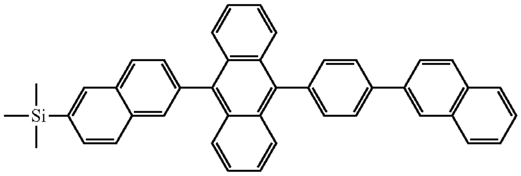

-continued
EM186
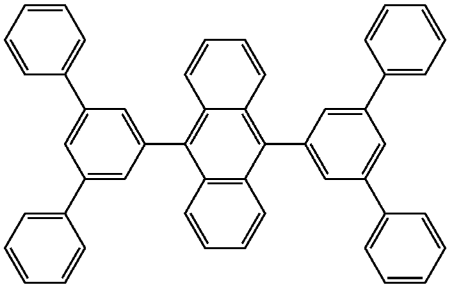
EM187
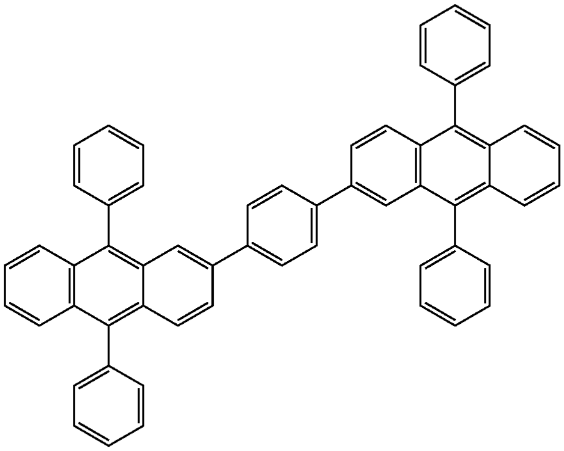
EM188
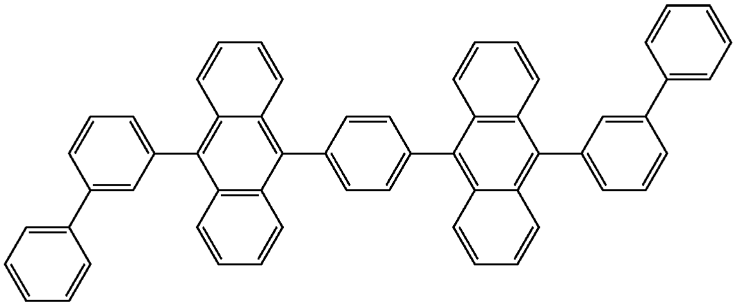
EM189
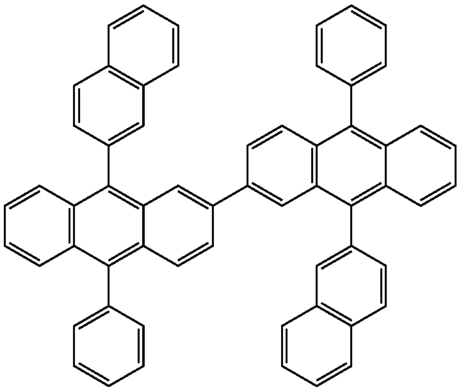
EM190
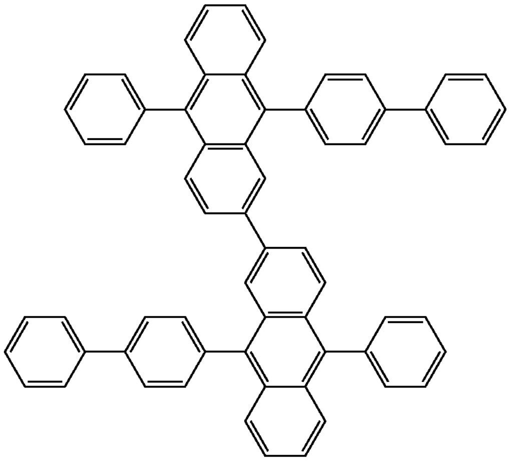
EM191
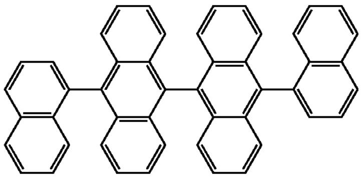
EM192
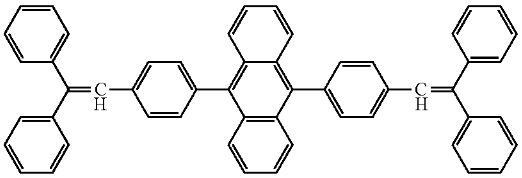

-continued
EM193
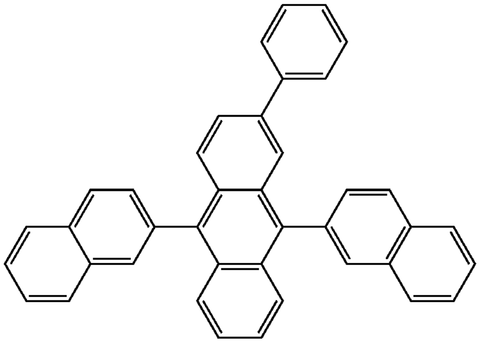
EM194
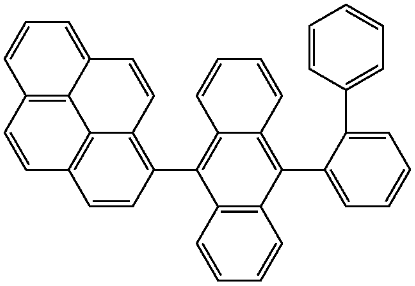
EM195
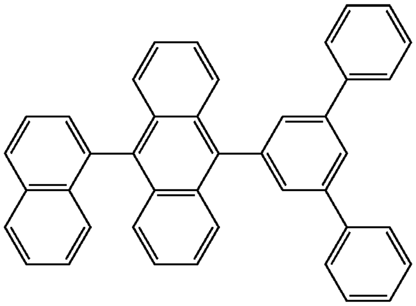
EM196
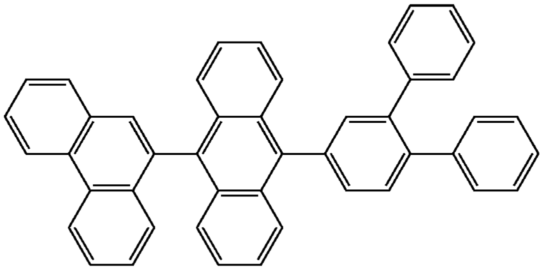
EM197
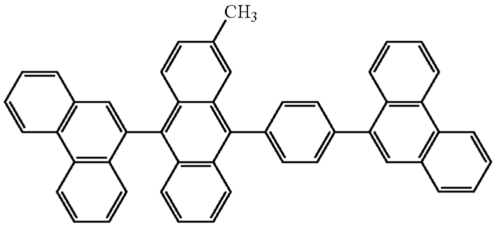
EM198
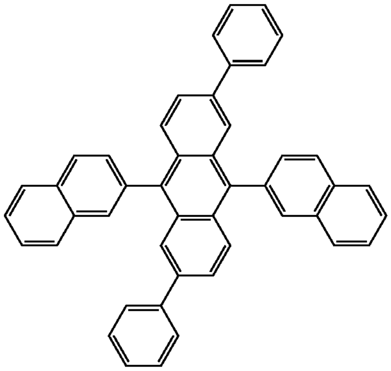
EM199
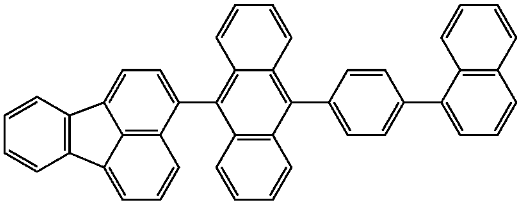
EM200
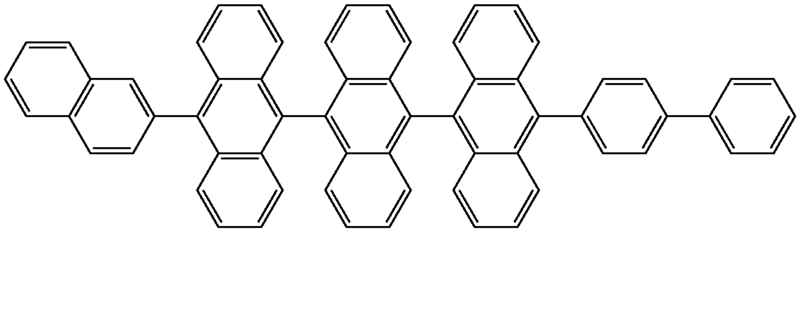

-continued
EM201
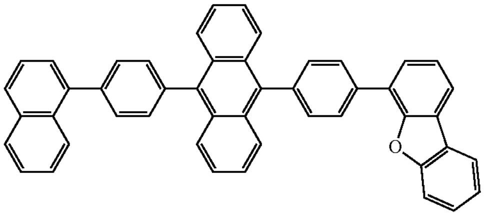
EM202
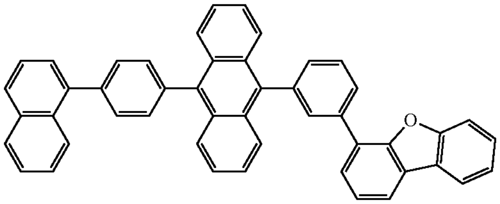
EM203
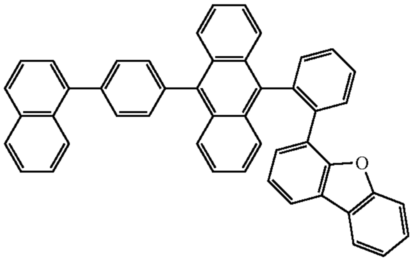
EM204
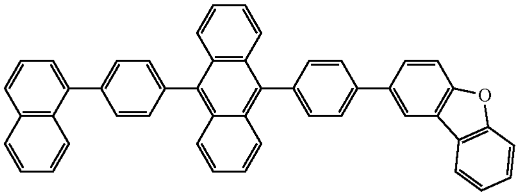
EM205
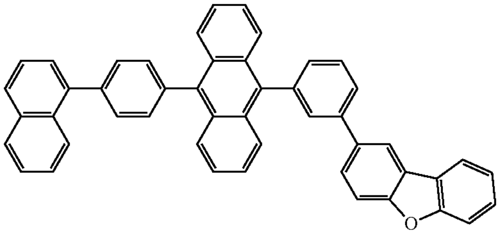
EM206
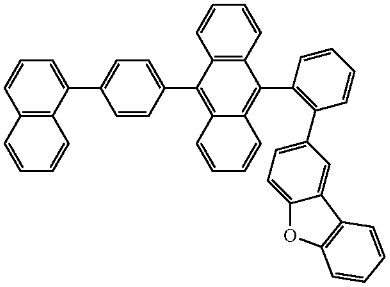
EM207
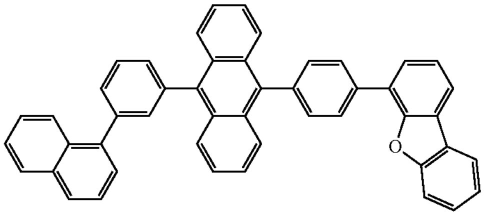
EM208
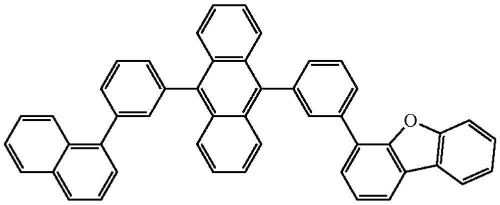
EM209
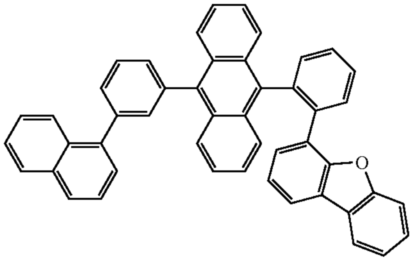
EM210
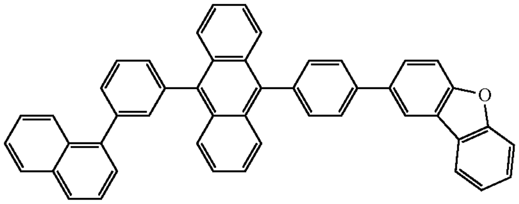

-continued
EM211
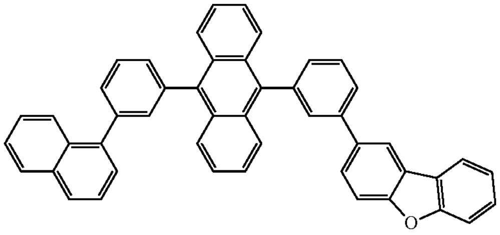
EM212
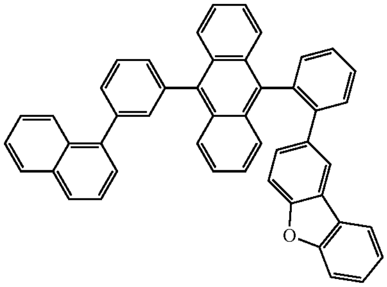
EM213
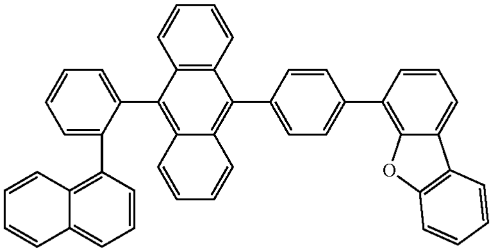
EM214
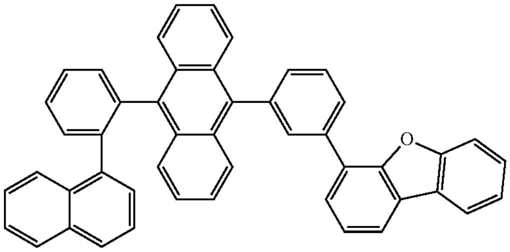
EM215
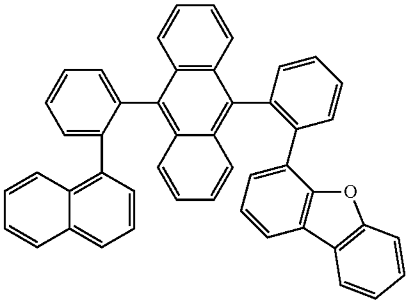
EM216
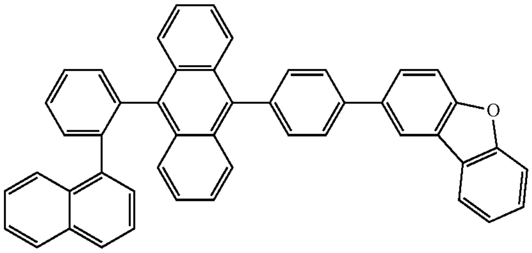
EM217
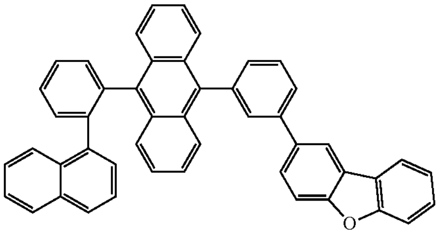
EM218
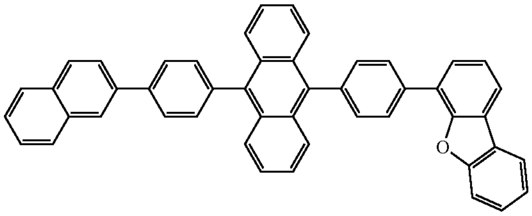
EM219
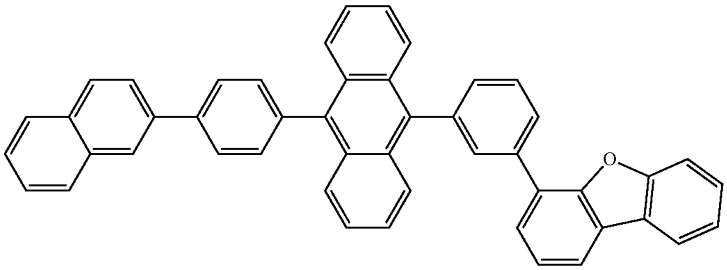

-continued
EM220
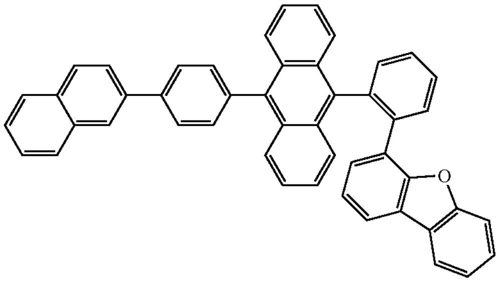
EM221
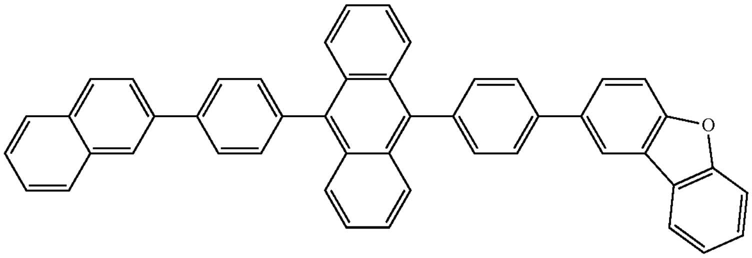
EM222
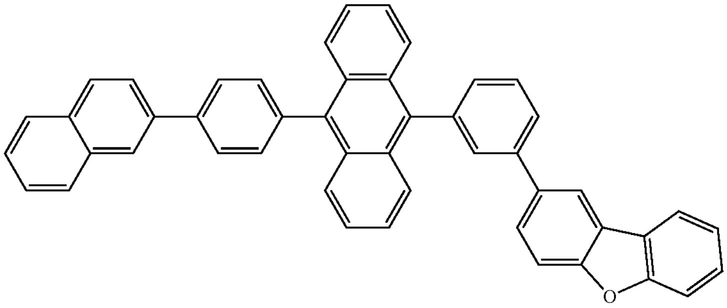
EM223
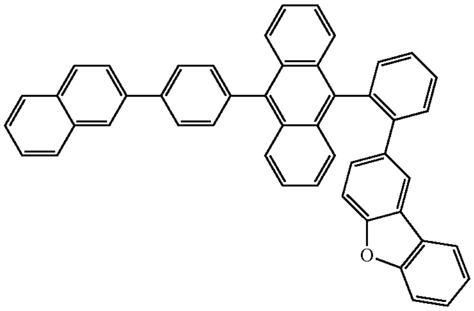
EM224
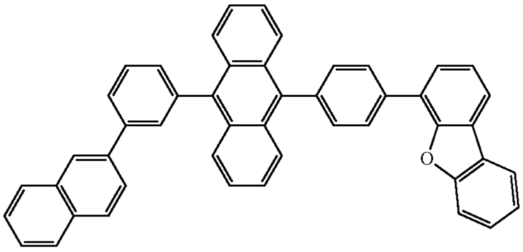
EM225
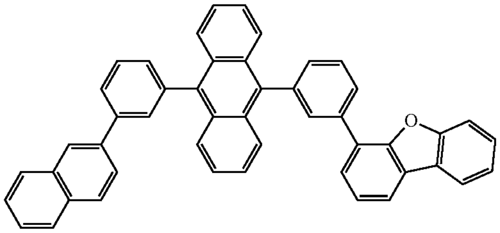
EM226
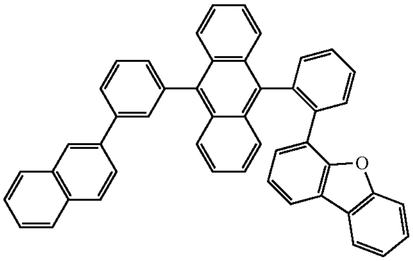

-continued
EM227
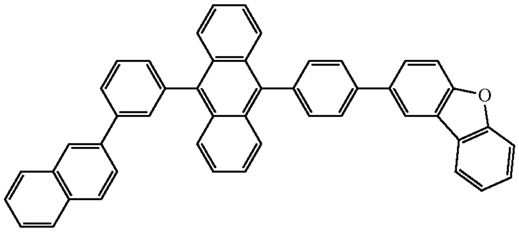
EM228
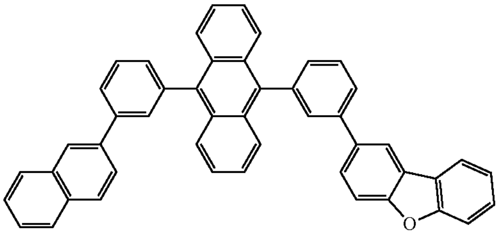
EM229
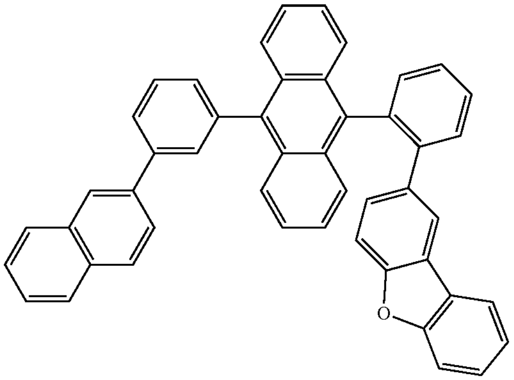
EM230
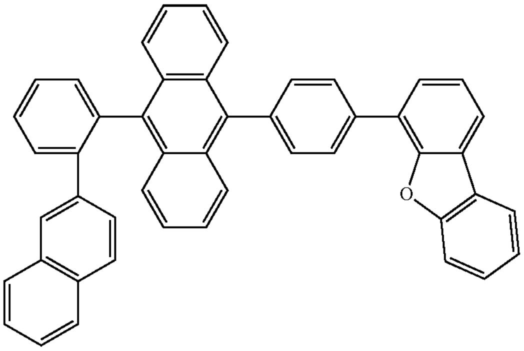
EM231
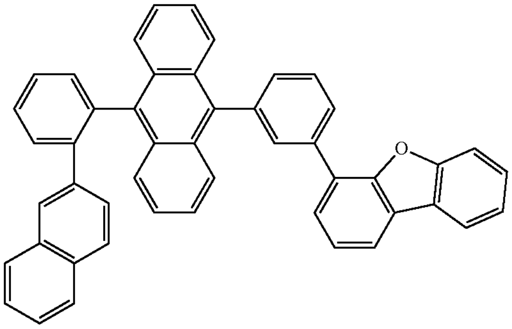
EM232
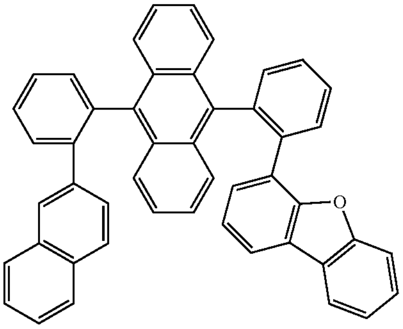
EM233
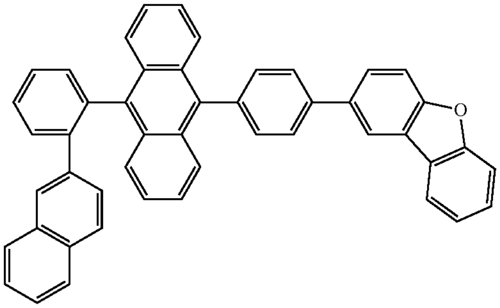
EM234
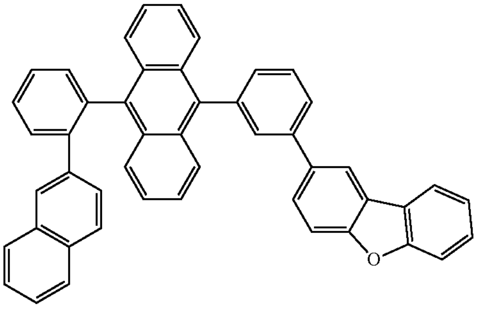

-continued
EM235
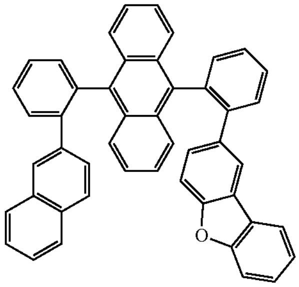
EM236
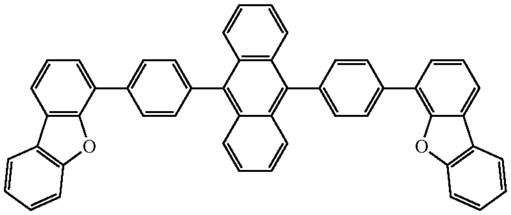
EM237
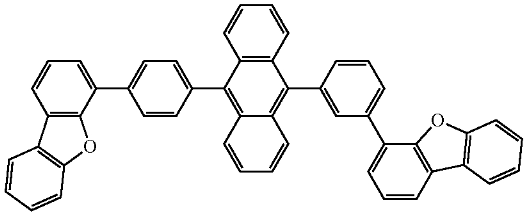
EM238
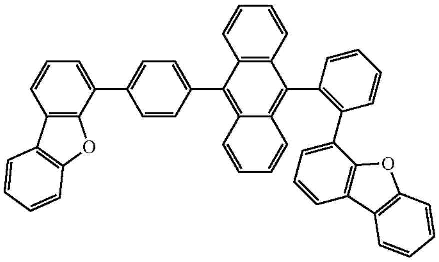
EM239
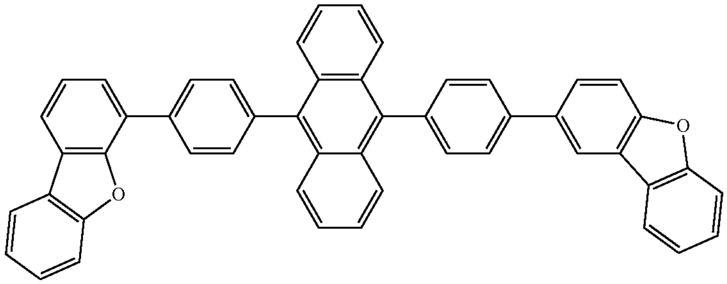
EM240
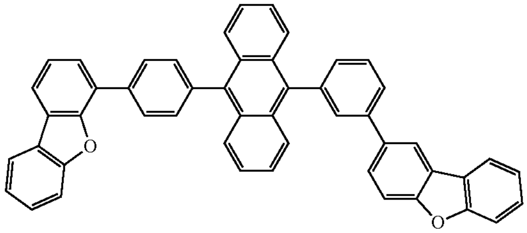
EM241
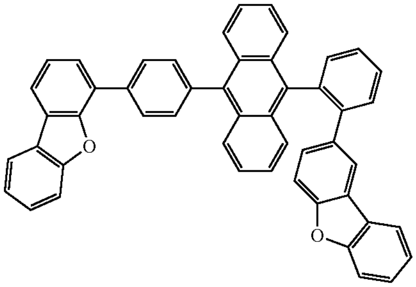
EM242
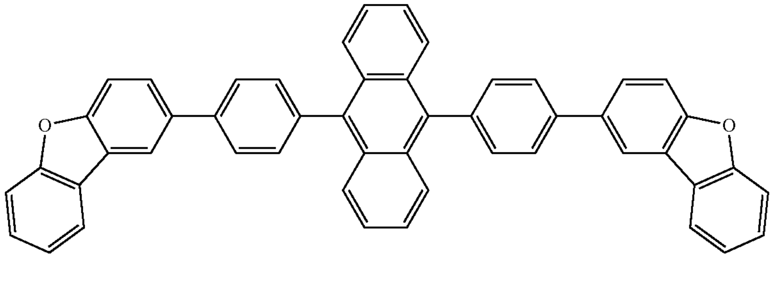

-continued
EM243
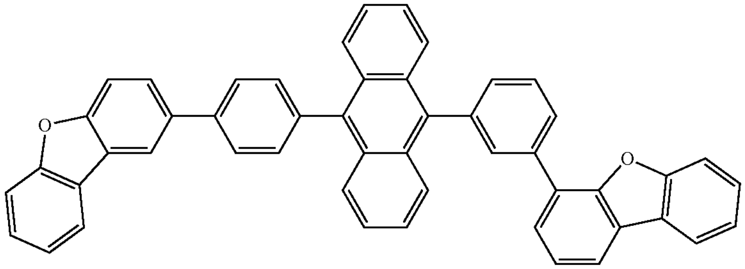
EM244
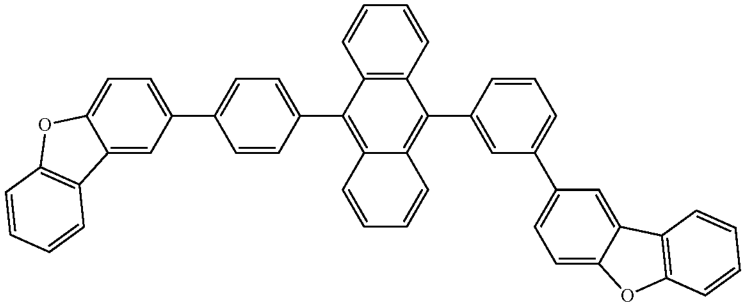
EM245
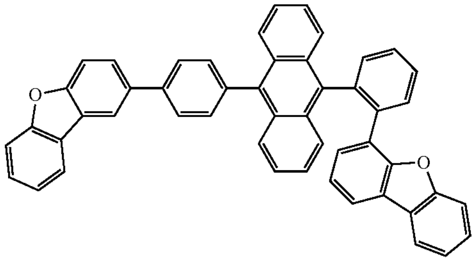
EM246
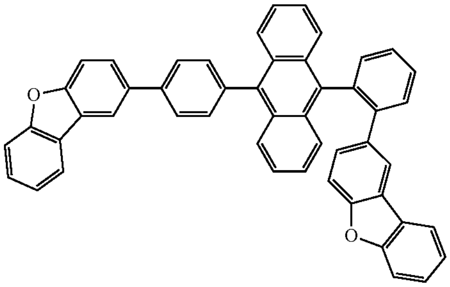
EM247
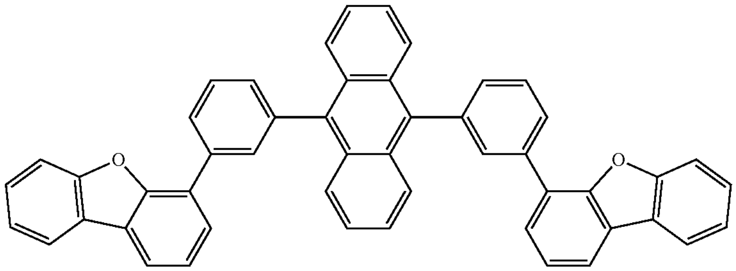
EM248
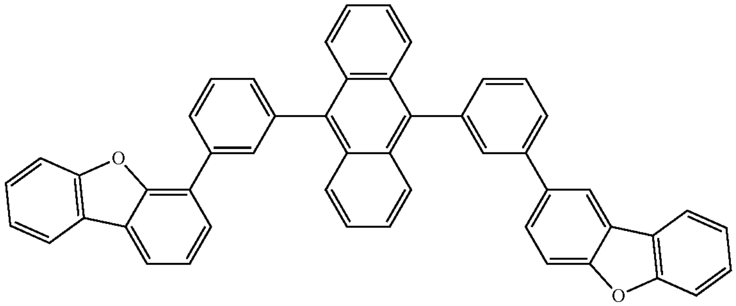

-continued
EM249
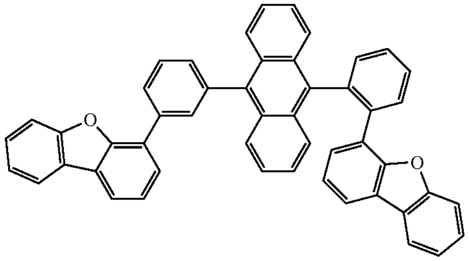
EM250
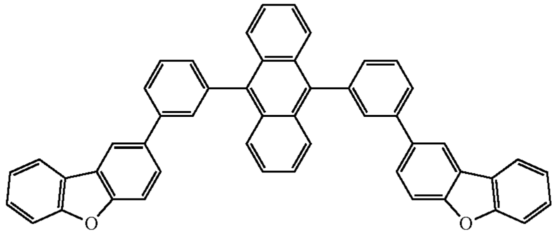
EM251
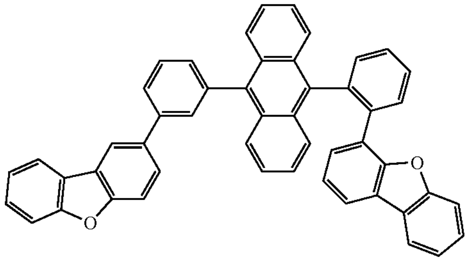
EM252
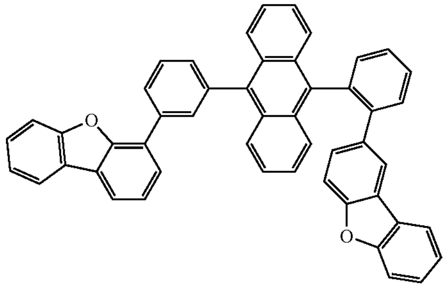
EM253
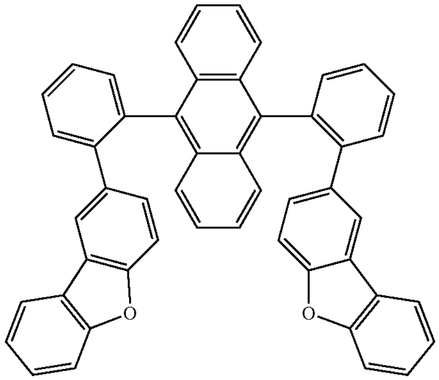
EM254
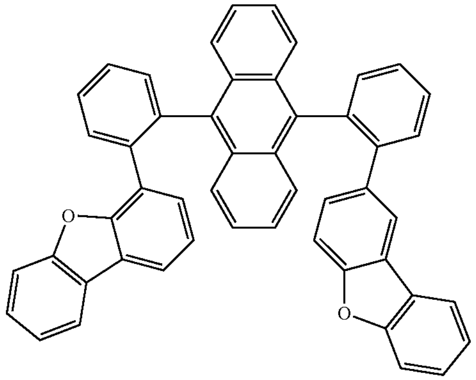
EM255
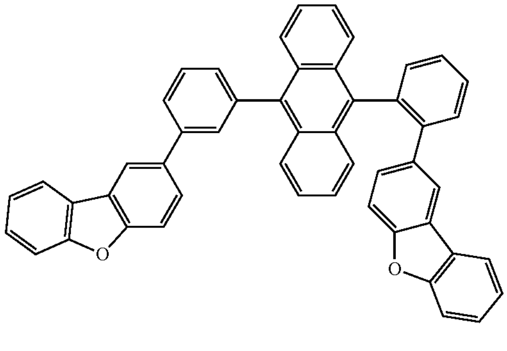
EM256
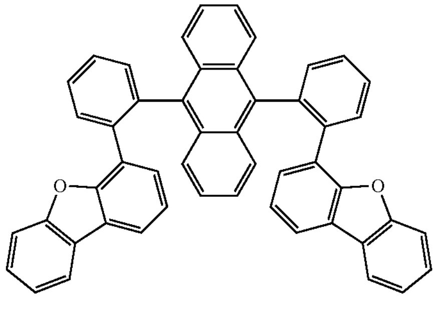
EM257
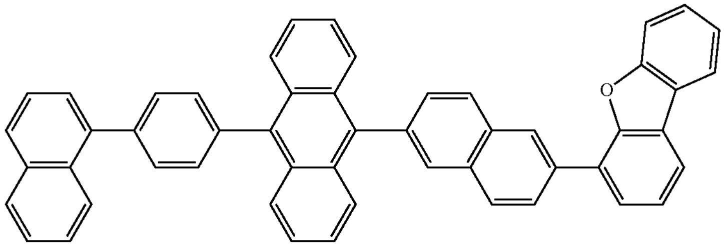

-continued
EM258
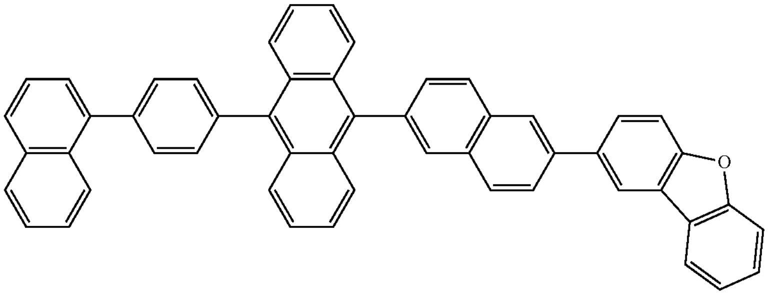
EM259
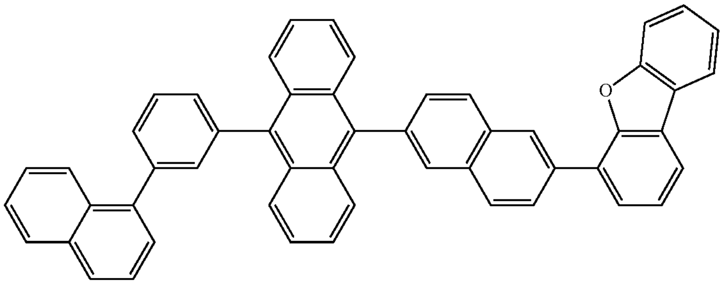
EM260
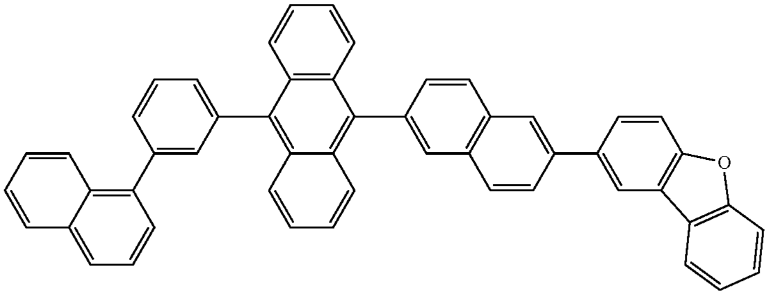
EM261
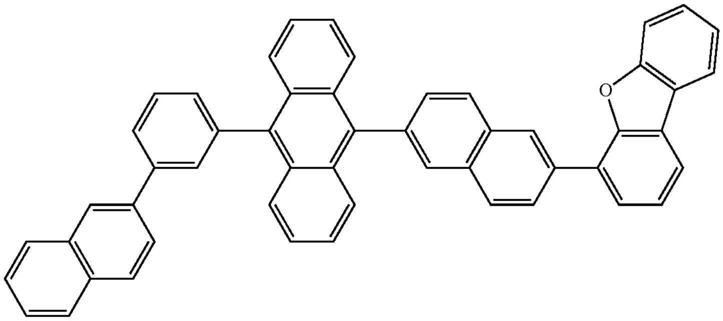
EM262
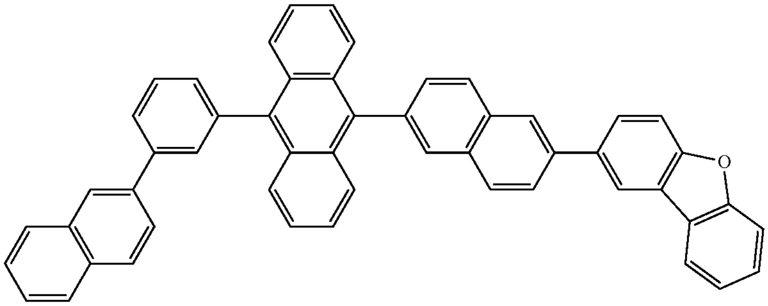

-continued
EM263
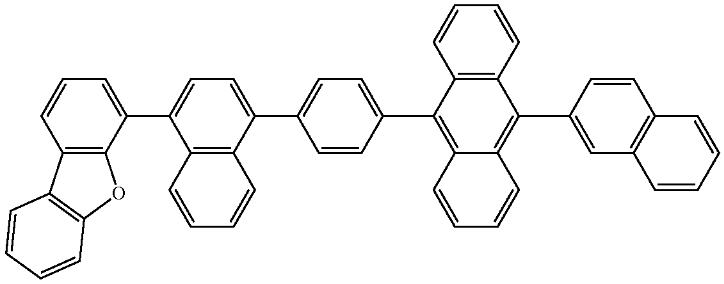
EM264
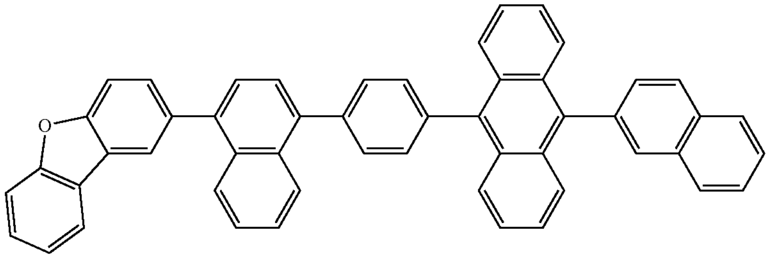
EM265
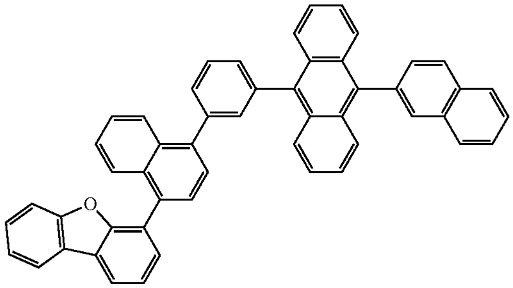
EM266
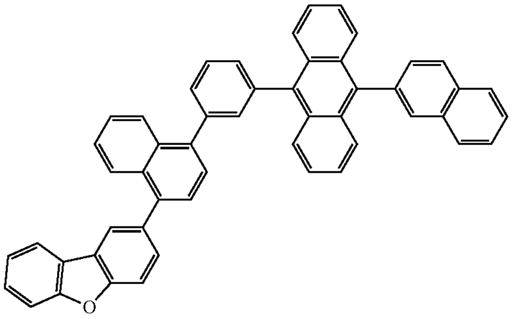
EM267
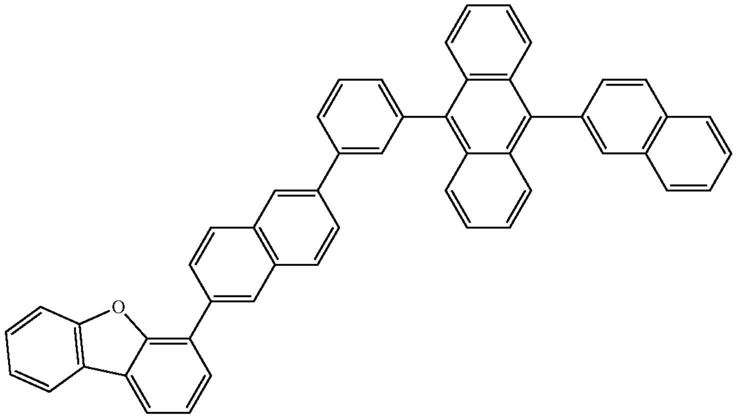

-continued
EM268
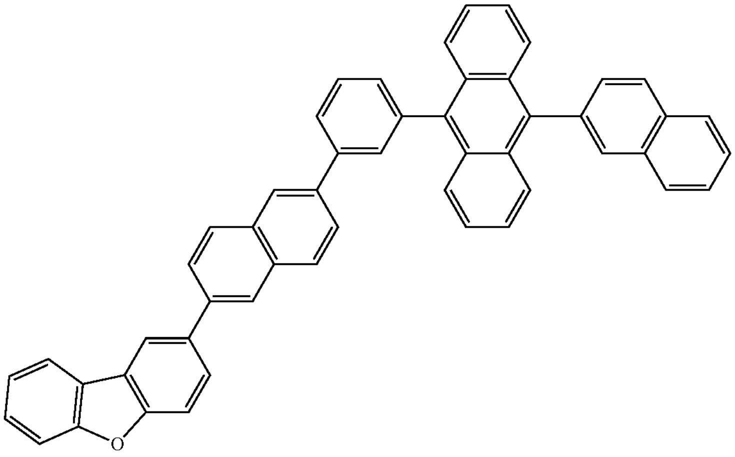
EM269
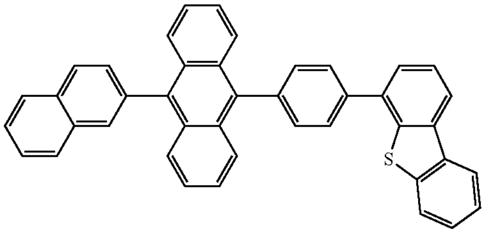
EM270
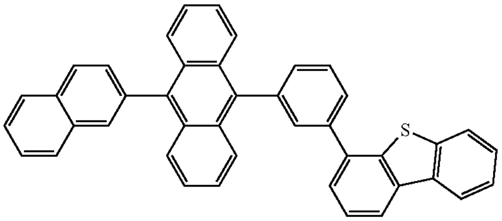
EM271
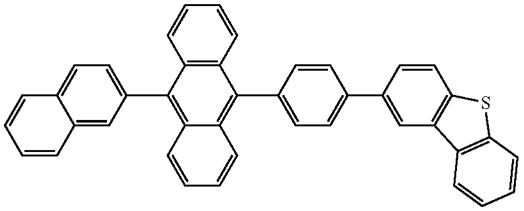
EM272
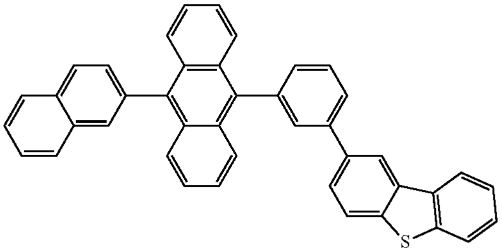
EM273
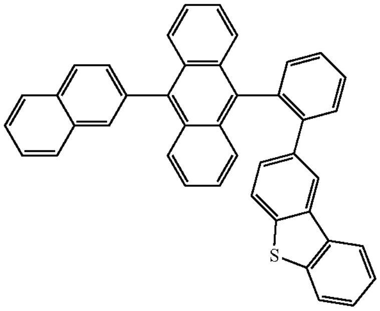
EM274
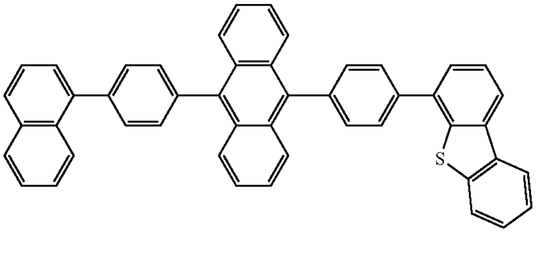
EM275
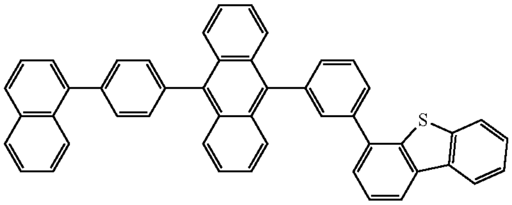
EM276
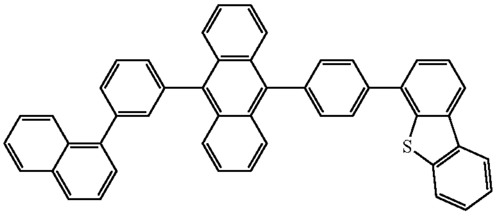

-continued
EM277
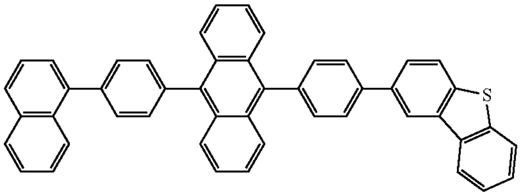
EM278
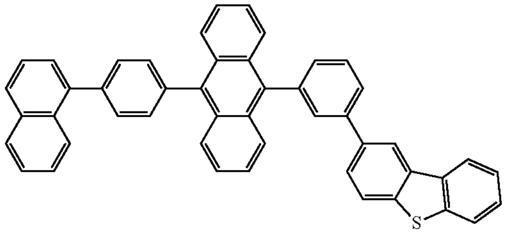
EM279
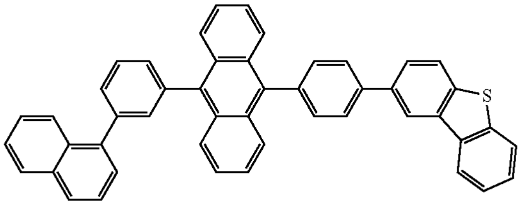
EM280
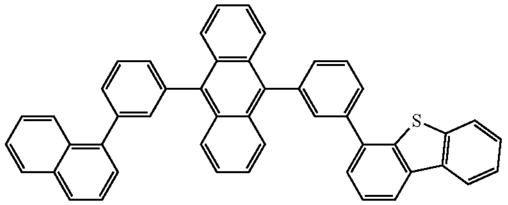
EM281
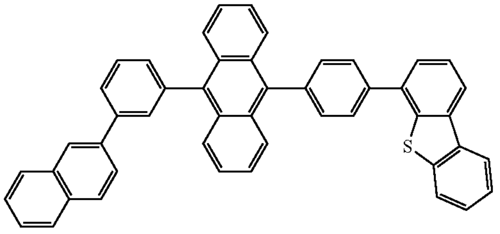
EM282
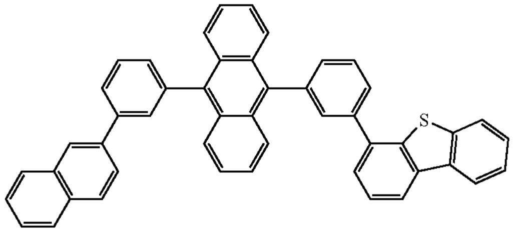
EM283
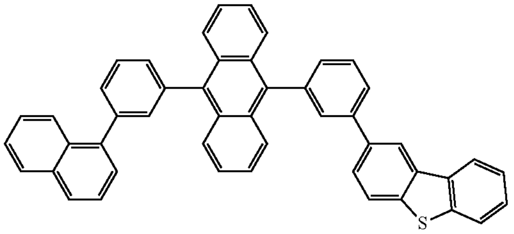
EM284
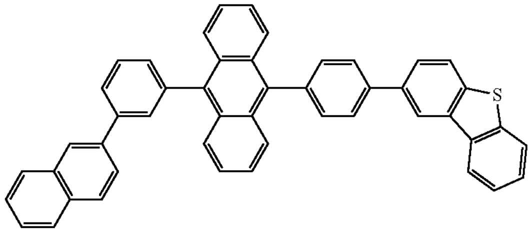
EM285
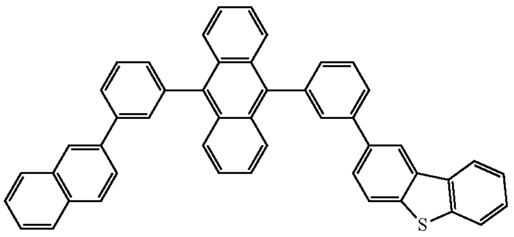

-continued
EM286
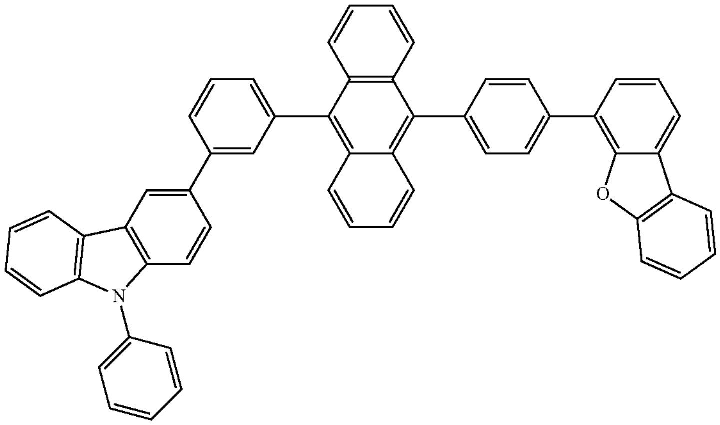
EM287
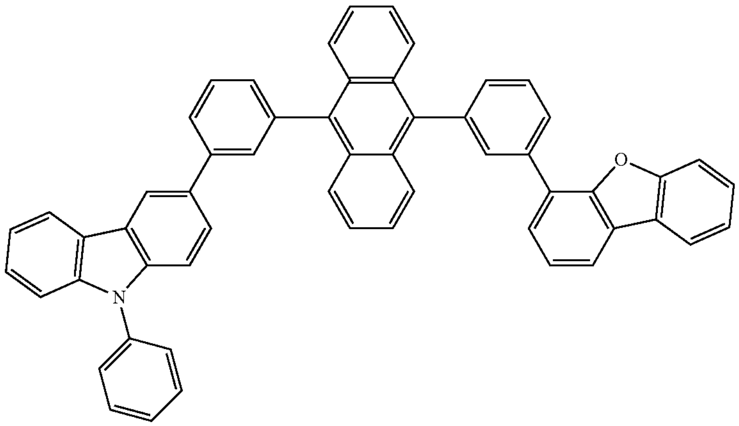
EM288
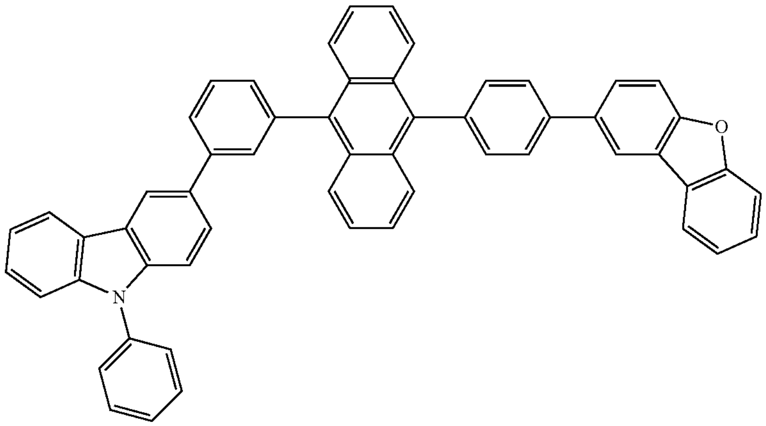

-continued
EM289
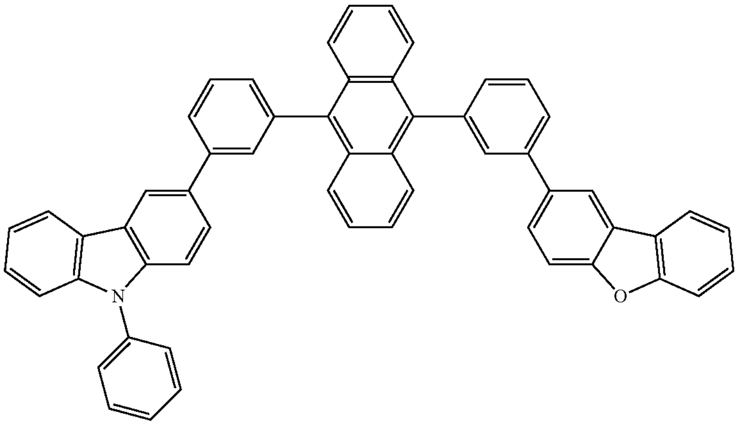
EM290
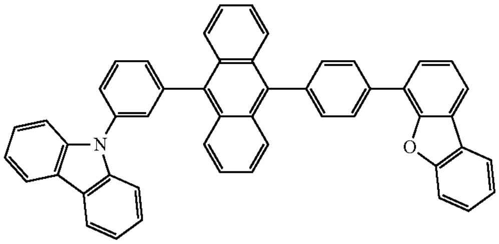
EM291
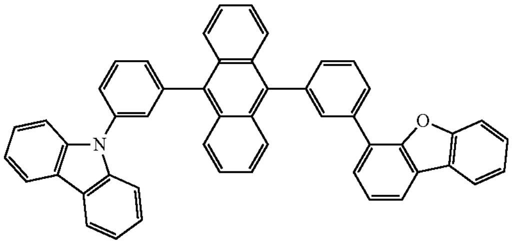
EM292
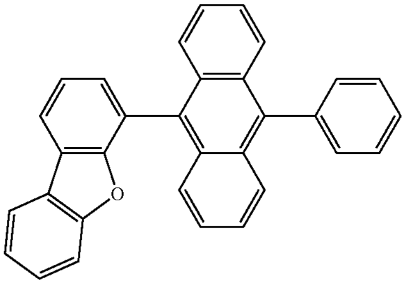
EM293
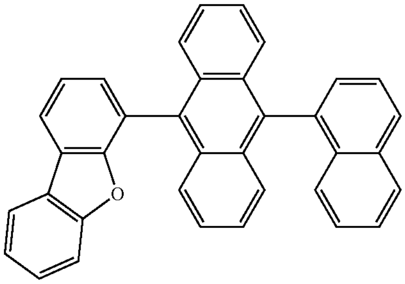
EM294
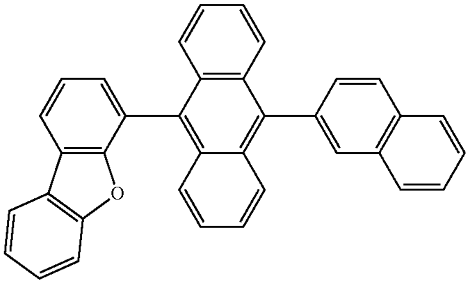
EM295
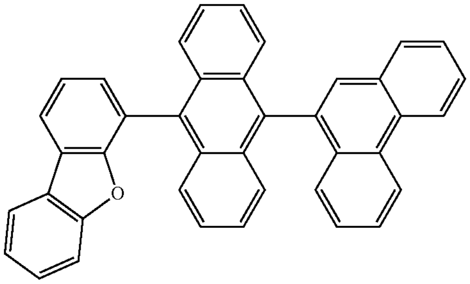
EM296
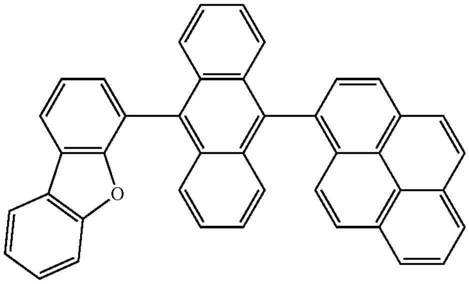
EM297
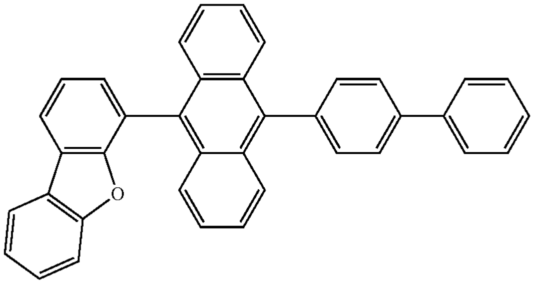

-continued
EM298
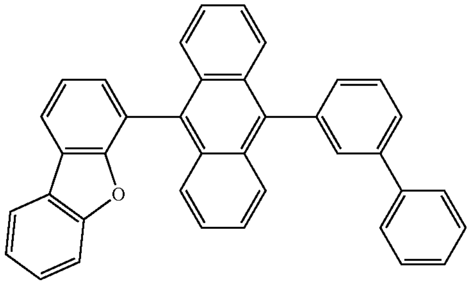
EM299
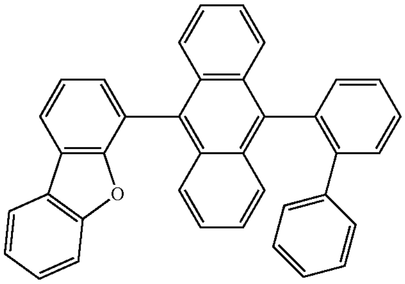
EM300
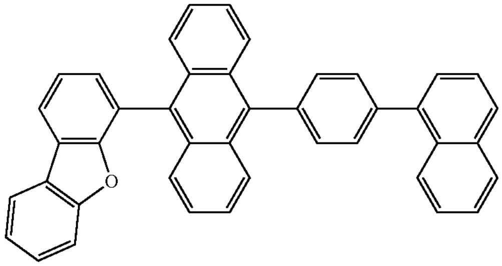
EM301
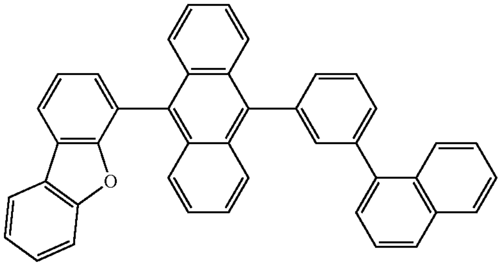
EM302
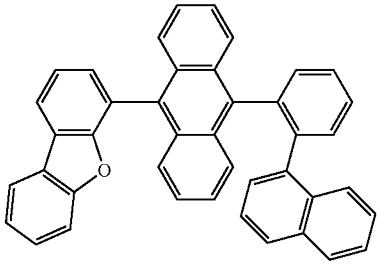
EM303
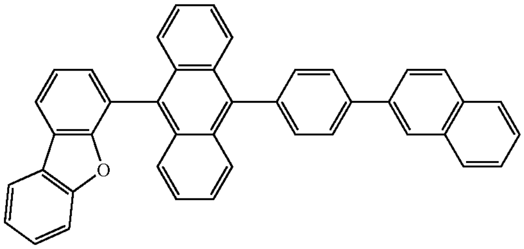
EM304
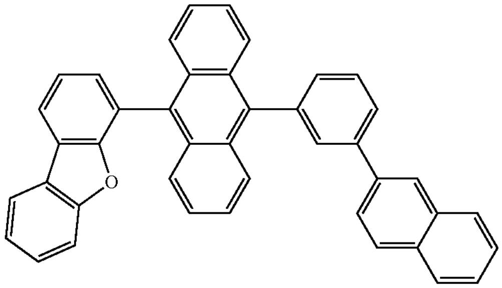
EM305
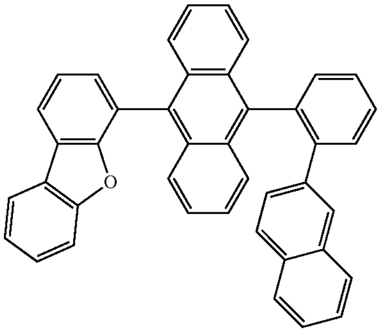
EM306
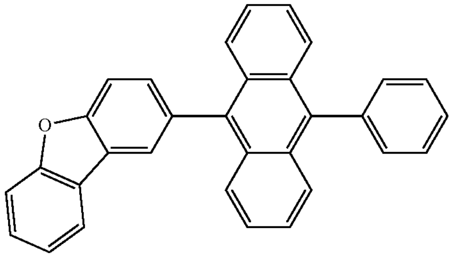
EM307
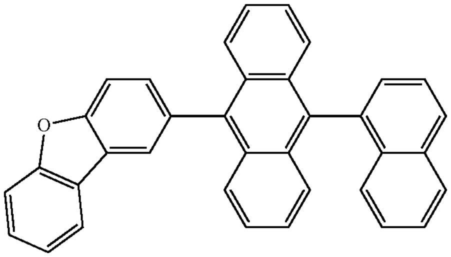

-continued
EM308
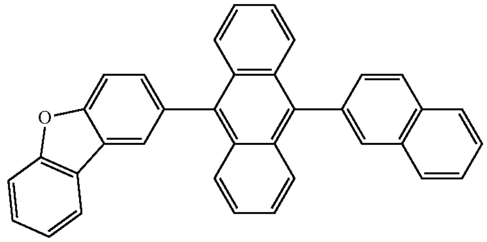
EM309
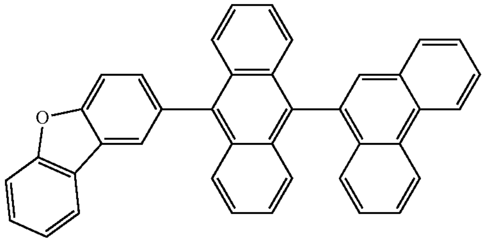
EM310
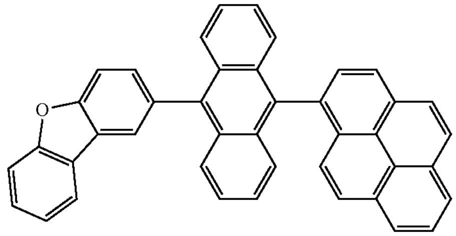
EM311
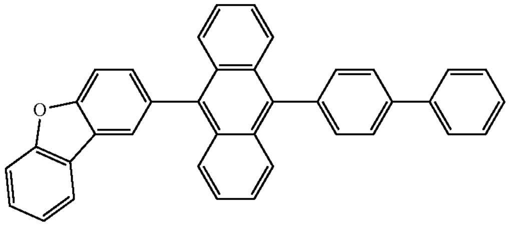
EM312
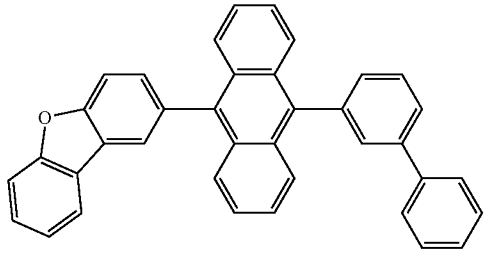
EM313
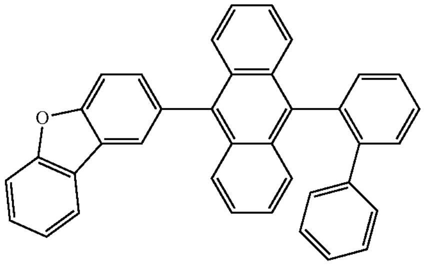
EM314
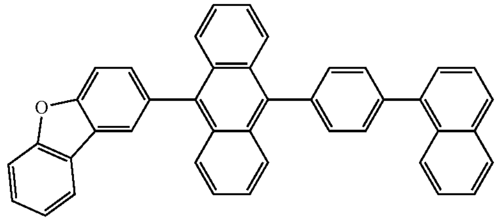
EM315
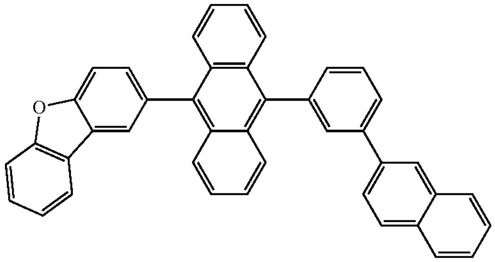
EM316
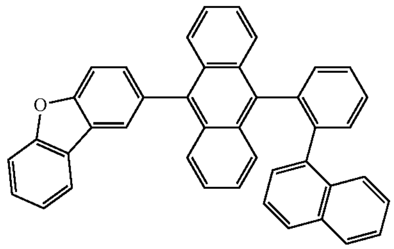
EM317
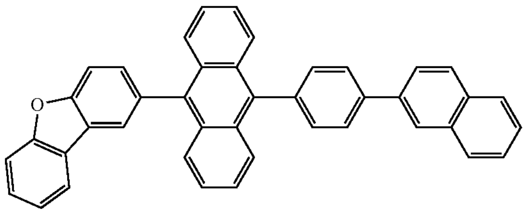
EM318
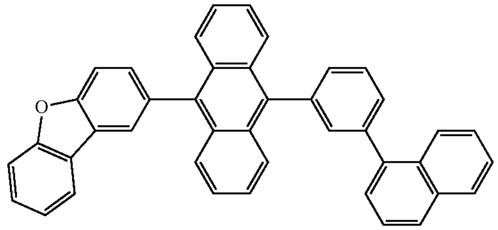
EM319
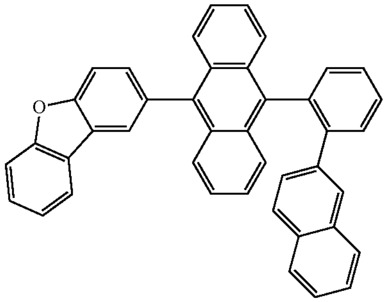

-continued
EM320
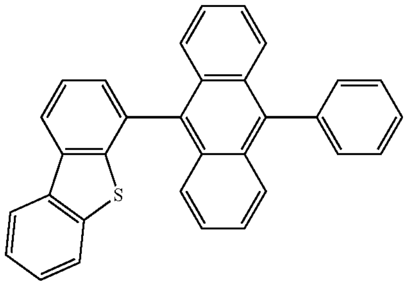
EM321
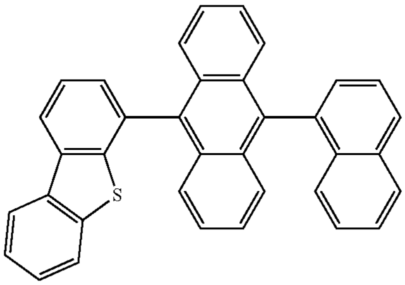
EM322
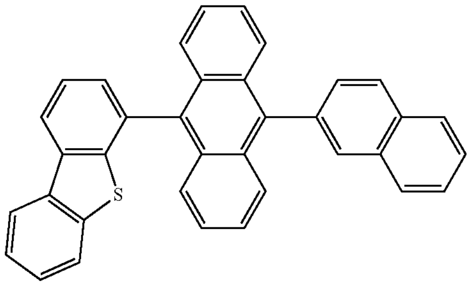
EM323
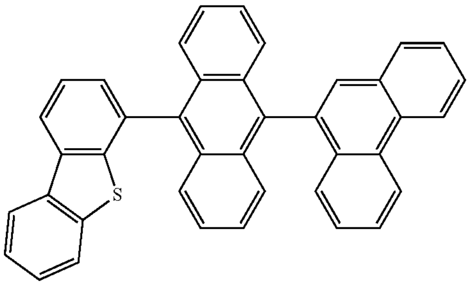
EM324
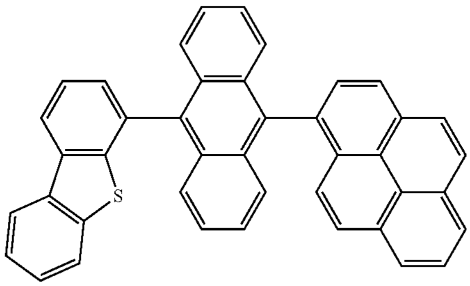
EM325
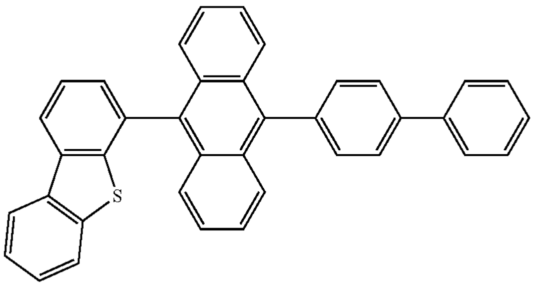
EM326
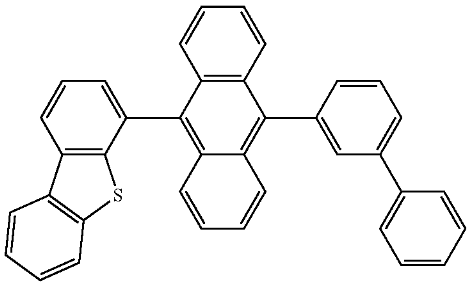
EM327
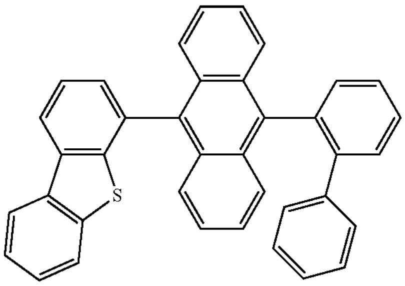
EM328
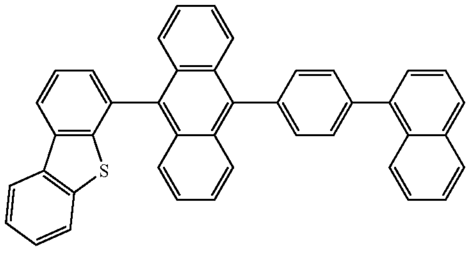
EM329
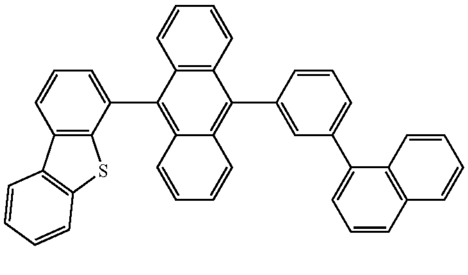

-continued
EM330
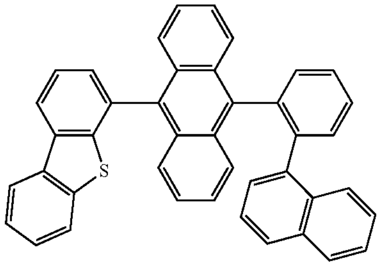
EM331
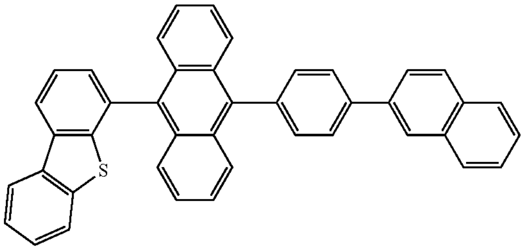
EM332
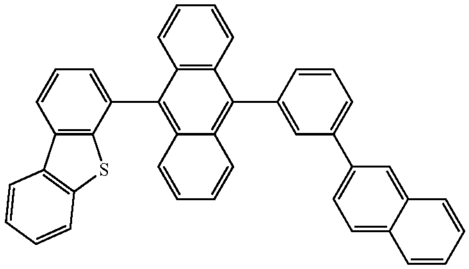
EM333
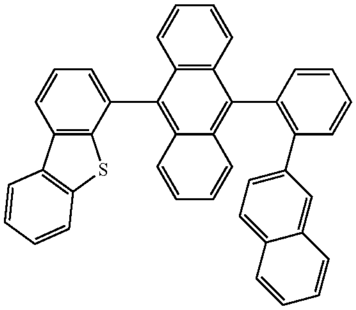
EM334
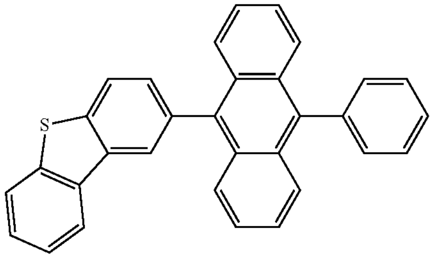
EM335
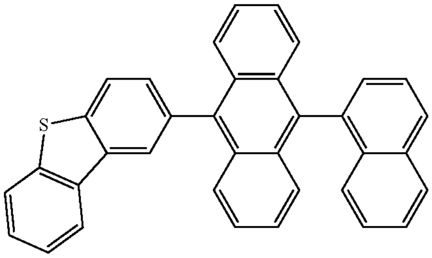
EM336
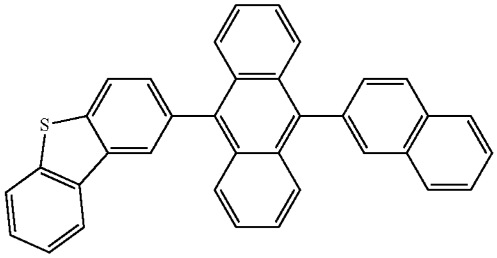
EM337
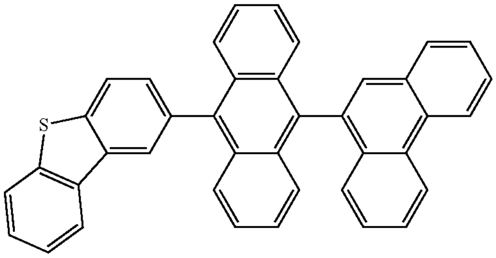
EM338
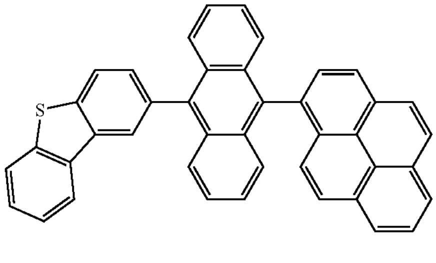
EM339
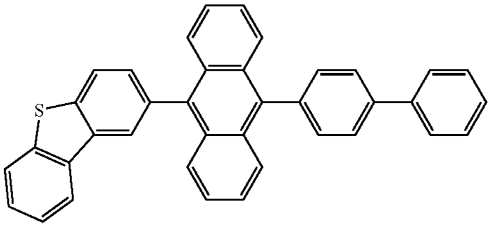

-continued
EM340
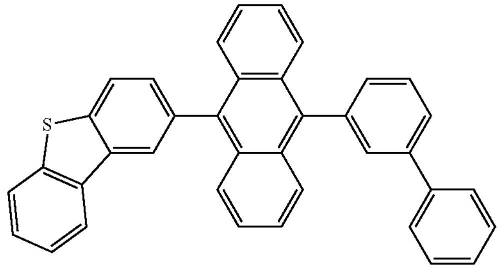
EM341
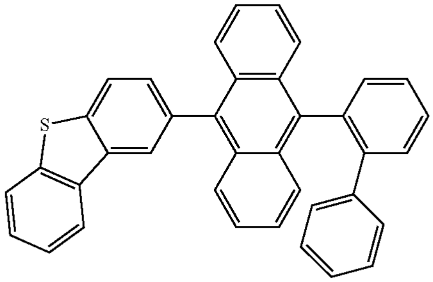
EM342
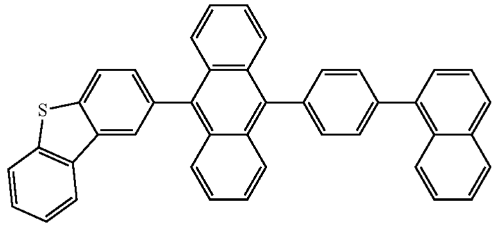
EM343
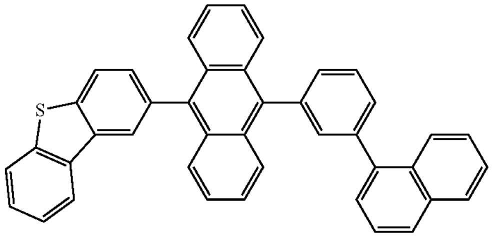
EM344
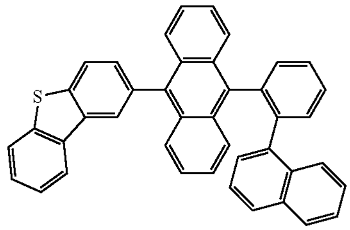
EM345
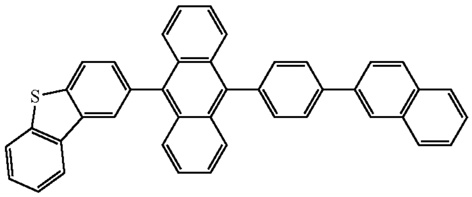
EM346
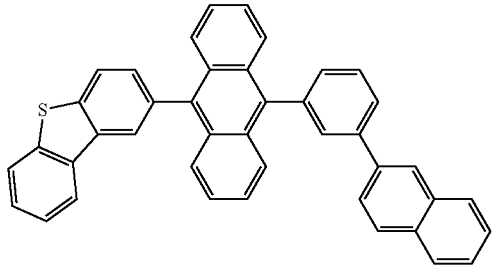
EM347
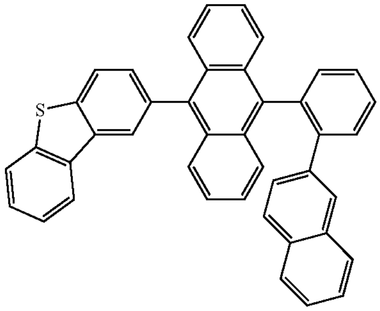
EM348
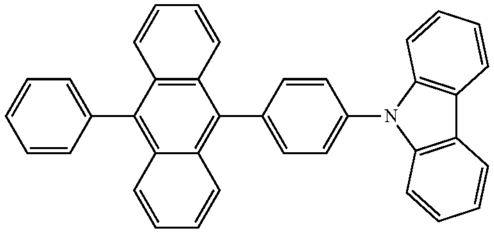
EM349
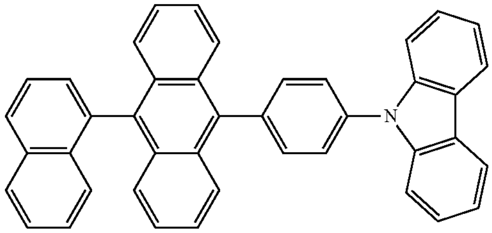

-continued
EM350
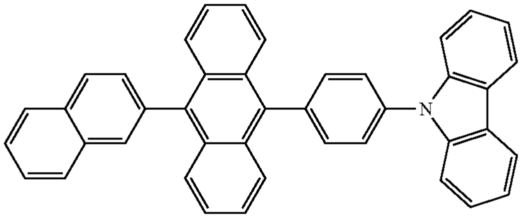
EM351
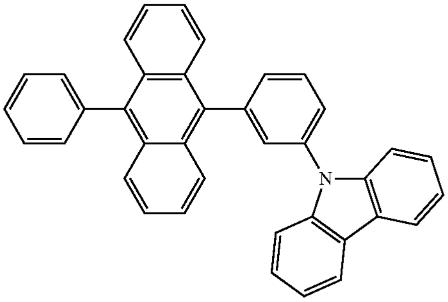
EM352
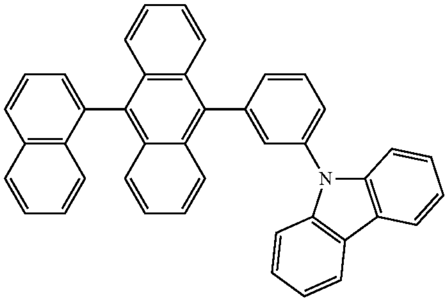
EM353
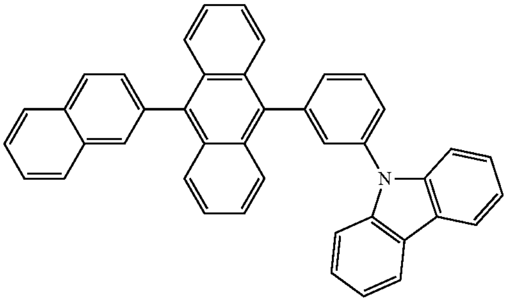
EM354
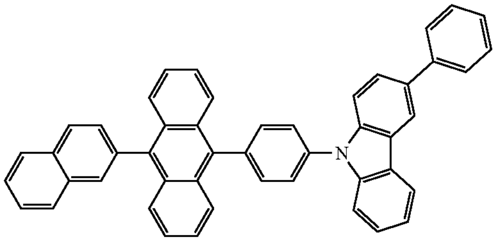
EM355
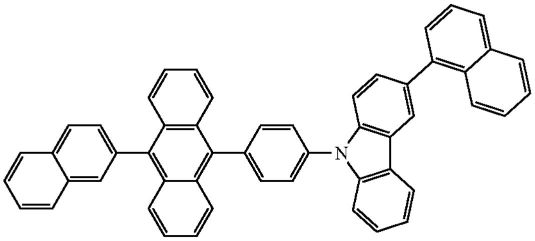
EM356
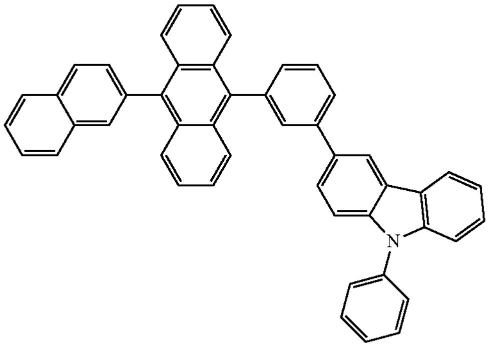
EM357
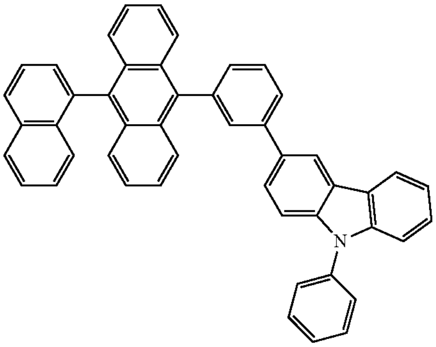
EM358
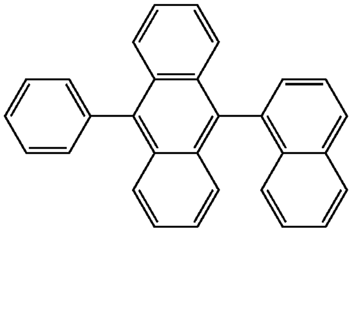
EM359
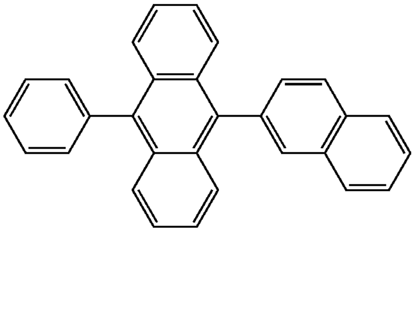

-continued
EM360
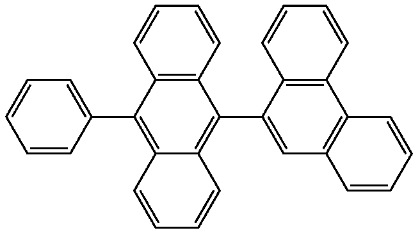
EM361
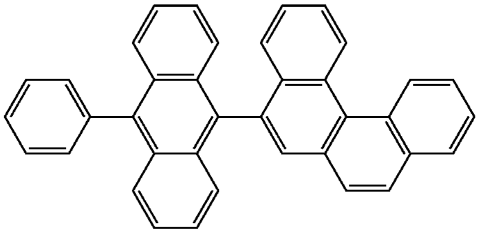
EM362
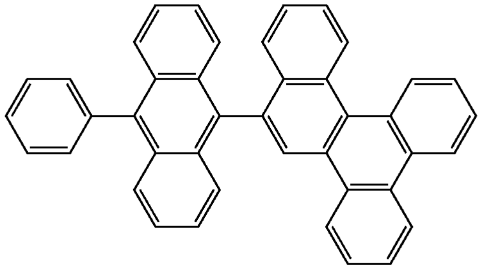
EM363
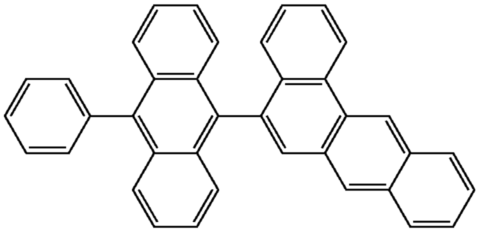
EM364
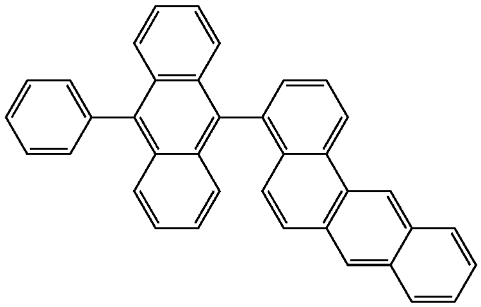
EM365
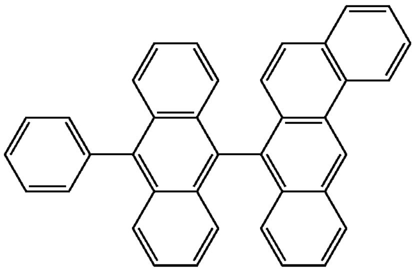
EM366
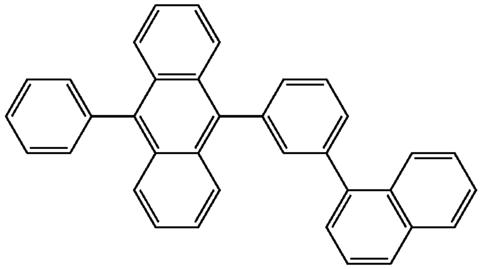
EM367
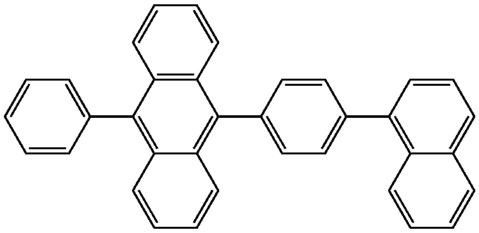
EM368
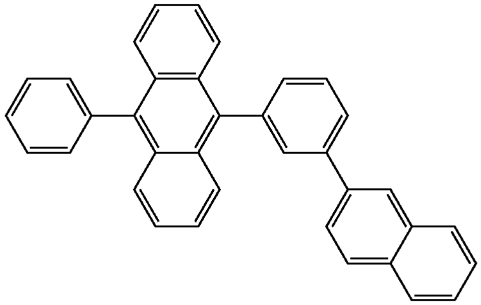
EM369
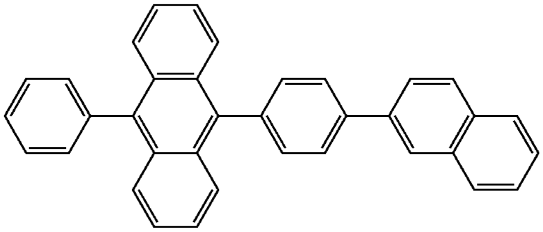

-continued
EM370
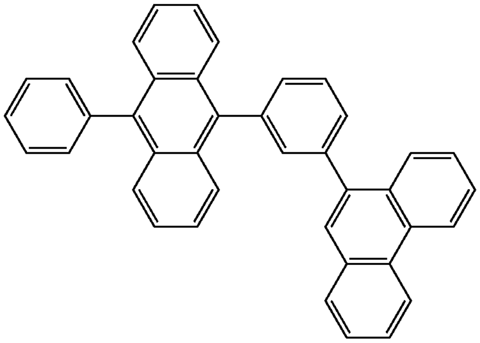
EM371
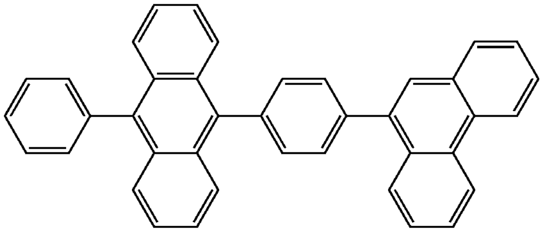
EM372
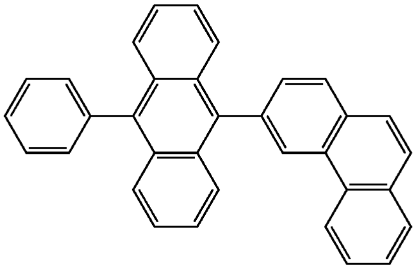
EM373
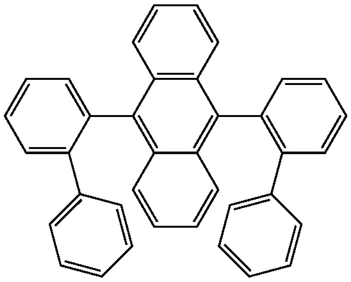
EM374
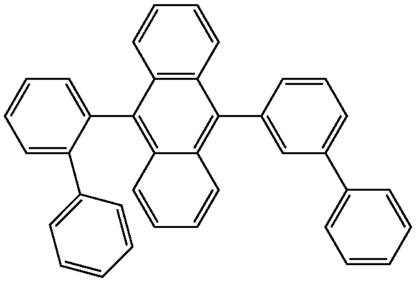
EM375
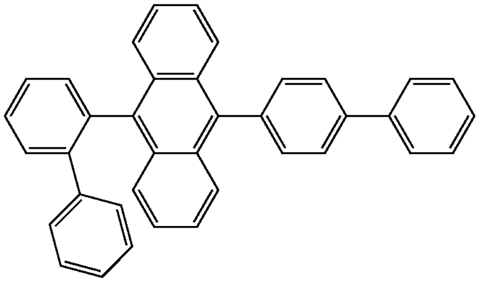
EM376
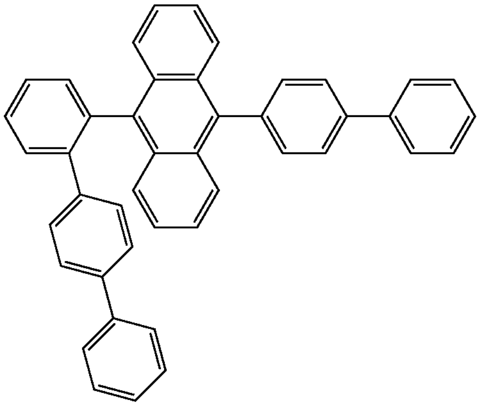
EM377
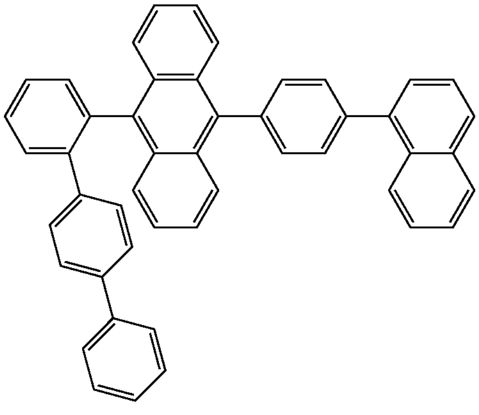

-continued
EM378
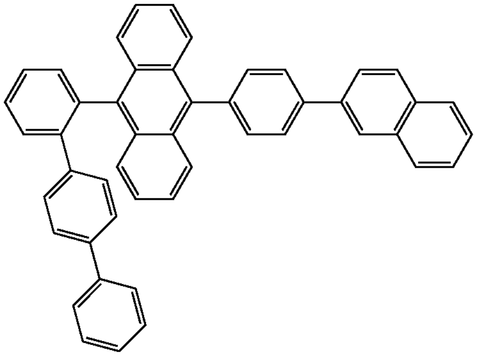
EM379
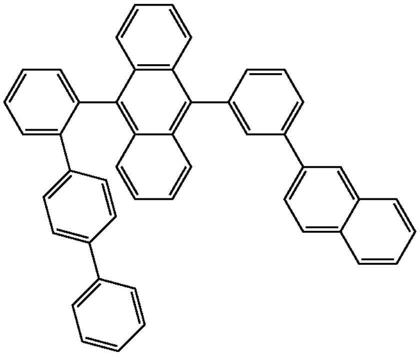
EM380
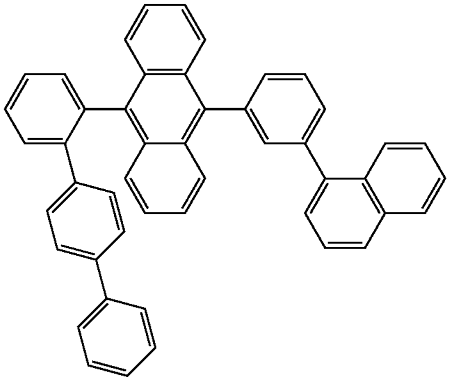
EM381
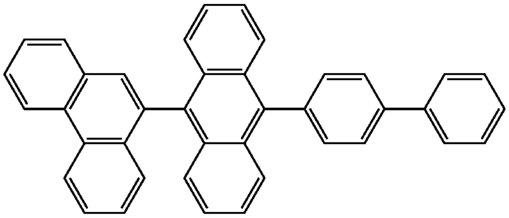
EM382
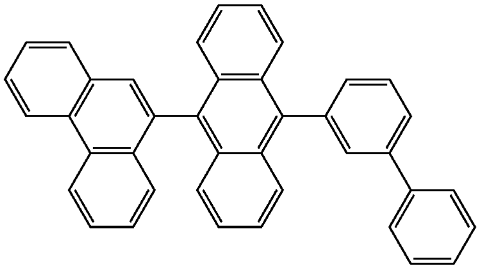
EM383
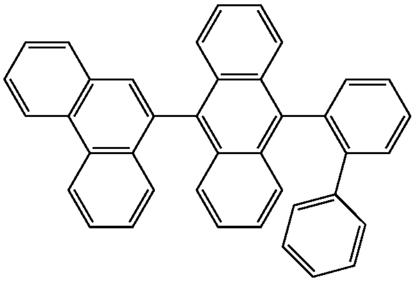
EM384
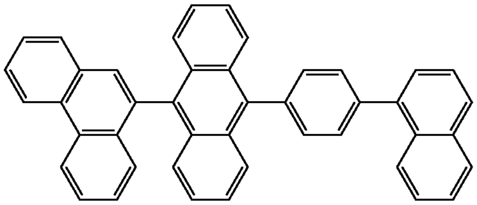
EM385
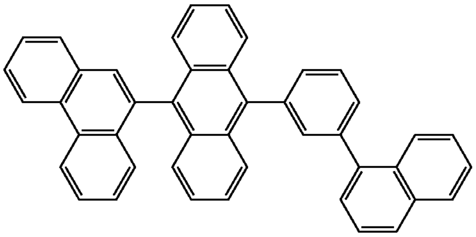
EM386
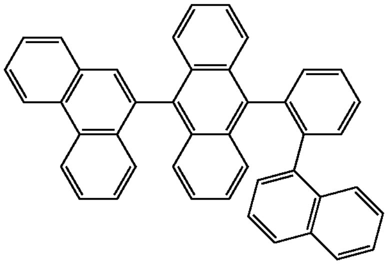
EM387
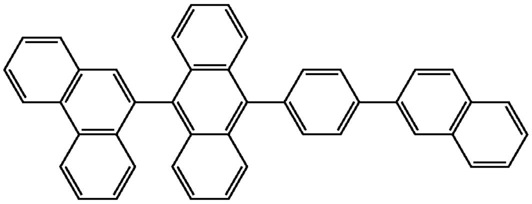

-continued

EM388

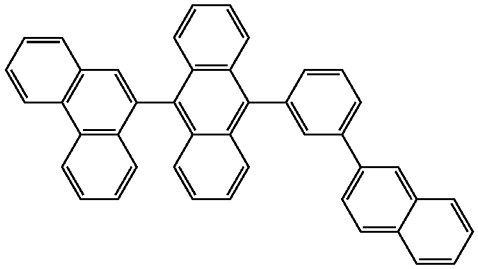

EM389

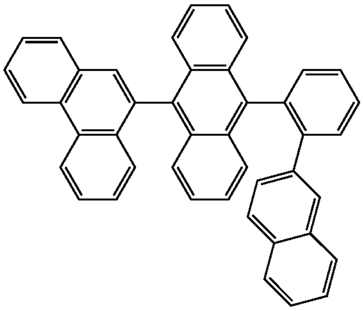

EM390

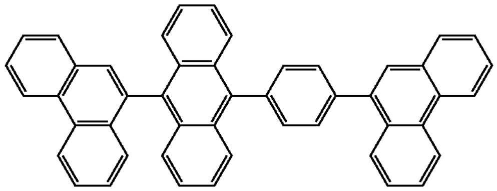

EM391

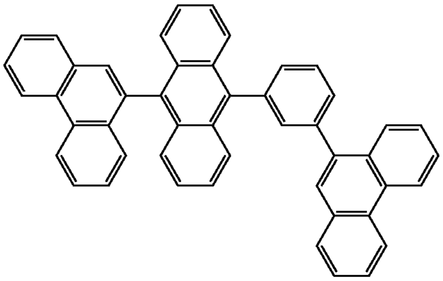

EM392

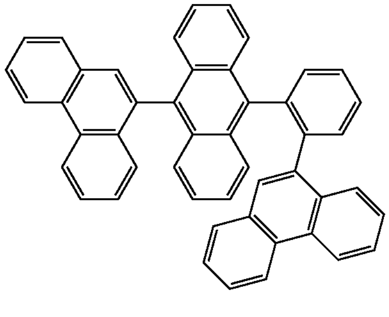

In another embodiment, the organic electroluminescence device may be a device in which at least one of the organic thin film layers comprises the aromatic amine derivative represented by the above formula (1) and a pyrene derivative represented by the following formula (6). It is more preferred that the emitting layer contain the aromatic amine derivative as a dopant and contain the pyrene derivative as a host.

(6)

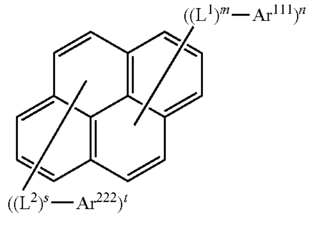

In the formula (6), $Ar^{111}$ and $Ar^{222}$ are independently a substituted or unsubstituted aryl group having 6 to 30 ring carbon atoms;

$L^1$ and $L^2$ are independently a substituted or unsubstituted divalent aryl group having 6 to 30 ring carbon atoms or a heterocyclic group;

m is an integer of 0 to 1, n is an integer of 1 to 4, s is an integer of 0 to 1, and t is an integer of 0 to 3; and $L^1$ or $Ar^{111}$ bonds to any position of the $1^{st}$ to $5^{th}$ positions of pyrene, and $L^2$ or $Ar^{222}$ bonds to any position of the $6^{th}$ to $10^{th}$ positions of pyrene.

$L^1$ and $L^2$ in the formula (6) are preferably a divalent aryl group composed of a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, or a combination of these substituents.

These substituents are the same as those of the "substituted or unsubstituted . . . " described above in the formulas (1) to (4). The substituents of $L^1$ and $L^2$ are preferably an alkyl group having 1 to 20 carbon atoms.

m in the formula (6) is preferably an integer of 0 to 1, and n in the formula (6) is preferably an integer of 1 to 2. s in the formula (6) is preferably an integer of 0 to 1.

t in the formula (6) is preferably an integer of 0 to 2.

The aryl groups of $Ar^{111}$ and $Ar^{222}$ are the same as those described in the formulas (1) to (4).

Preferable aryl groups are a substituted or unsubstituted aryl group having 6 to 20 ring carbon atoms, with a substituted or unsubstituted aryl group having 6 to 16 ring carbon atoms being more preferable. Preferable specific examples of the aryl groups include a phenyl group, naphthyl group, phenanthryl group, fluorenyl group, biphenyl group, anthryl group and pyrenyl group.

When the aromatic amine derivative is contained as a dopent, the amount thereof is preferably 0.1 to 20 mass %, more preferably 1 to 10 mass %.

The aromatic amine derivative and the anthracene derivative or the pyrene derivative may be used in a hole-injecting layer, a hole-transporting layer, an electron-injecting layer, and an electron-transporting layer in addition to an emitting layer.

In the invention, as the organic EL device in which the organic thin film layer is composed of plural layers, one in which an anode, a hole-injecting layer, an emitting layer and a cathode are sequentially stacked (anode/hole-injecting layer/emitting layer/cathode), one in which an anode, an emitting layer, an electron-injecting layer and a cathode are sequentially stacked (anode/emitting layer/electron-injecting layer/cathode), one in which an anode, a hole-injecting layer, an emitting layer, an electron-injecting layer and a cathode are sequentially stacked (anode/hole-injecting layer/emitting layer/electron-injecting layer/cathode), one in which an anode, a hole-injecting layer, a hole-transporting layer, an emitting layer, an electron-injecting layer and a cathode are sequentially stacked (anode/hole-injecting layer/hole-transporting layer/emitting layer/electron-injecting layer/cathode) or the like can be given.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the material other than those represented by the formula (5) which can be used in the emitting layer together with the aromatic amine derivative of the invention include, though not limited thereto, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene and derivatives thereof, organic metal complexes such as tris(8-quinolinolate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives and quinacrylidone derivatives.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2$Pc, CuPc, CoPc, NiPc, ZnPc, PdPc, FePc, MnPc, ClAlPc, ClGaPc, ClInPc, ClSnPc, $Cl_2$SiPc, (HO)AlPc, (HO)GaPc, VOPc, TiOPc, MoOPc and GaPc-O—GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeleton.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate) aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzoimidazole, imidazopyridine or the like are preferable, for example. Of these, a benzimidazole derivative, a phenanthroline derivative and an imidazopyridine derivative are prereable.

As a preferred embodiment, a dopant is further contained in these electron-injecting materials, and in order to facilitate receiving electrons from the cathode, it is further preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one of the above-mentioned aromatic amine derivatives represented by the formula (1), at least one of an emitting material, a doping material, a hole-injecting material, a hole-transporting material and an electron-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solution suitable for such wet film-forming method, it is possible to use an organic EL material-containing solution which contains the aromatic amine derivative of the invention as an organic EL material and a solvent.

It is preferred that the above-mentioned organic EL material contain a host material and a dopant material, the dopant material be the aromatic amine derivative of the invention and the host material be at least one selected from compounds represented by the formula (5).

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, a navigation light, or the like. The compound of the invention can be use not only in an organic EL device but also in the field of an electrophotographic photoreceptor, a photoelectric converting element, a solar cell and an image sensor.

EXAMPLES

Production Example 1

Aromatic amine derivative D-1 was produced as follows:

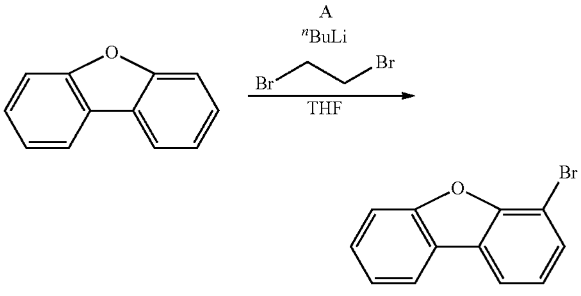

M1

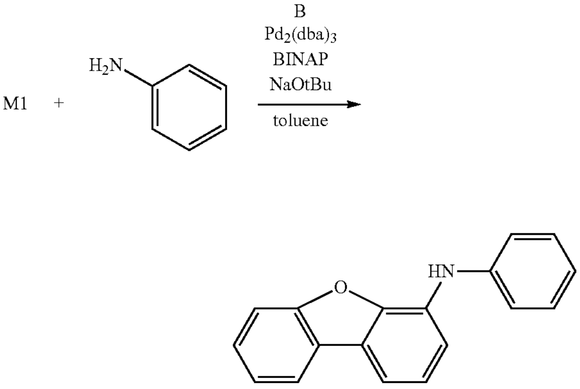

M2

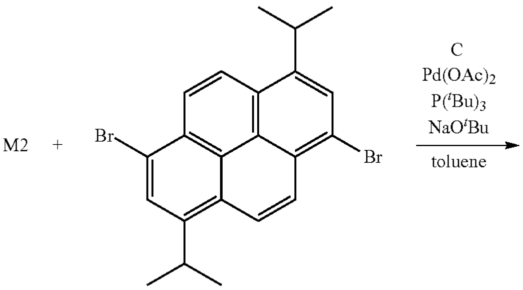

-continued

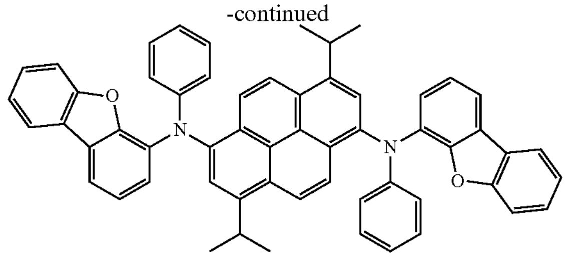

D-1

(1) Synthesis of Intermediate M1 (Reaction A)

In a stream of argon, 30.0 g of dibenzofuran and 300 mL of dehydrated tetrahydrofuran (THF) were put in a 1000 mL-recovery flask, and the resulting solution was cooled to −65° C. Then, 120 mL (1.65 M) of a hexane solution of n-butyllithium was added. The resulting mixture was heated gradually, and allowed to react at room temperature for 3 hours. After cooling to −65° C. again, 23.1 mL of 1,2-dibromoethane was added dropwise thereto, and the reaction mixture was heated gradually and a reaction was conducted for 3 hours at room temperature.

The reaction solution was separated and extracted by adding 2N hydrochloric acid and ethyl acetate, and then the organic phase was washed with clean water and saturated saline and dried with sodium sulfate, and concentrated to obtain a crude product. The crude product was purified with silica gel chromatography (methylene chloride), and solids obtained were dried under reduced pressure to obtain 43.0 g of white solids. The solids were identified as intermediate M1 by FD-MS (field desorption mass spectrometry) analysis.

(2) Synthesis of Intermediate M2 (Reaction B)

In a stream of argon, 11.7 g of intermediate M1, 10.7 mL of aniline, 0.63 g of tris(dibenzylideneacetone)dipalladium (0) [$Pd_2(dba)_3$], 0.87 g of 2,2'-bis(diphenylphosphino)-1,1'-binaphthyl [BINAP], 9.1 g of sodium tert-butoxide and 131 mL of dehydrated toluene were put in a 300 mL-recovery flask. A reaction was conducted at 85° C. for 6 hours.

After cooling, the reaction solution was filtered through cellite. A crude product obtained was purified by silica gel column chromatography (n-hexane/methylene chloride (3/1)). Solids obtained were dried under reduced pressure to obtain 10.0 g of white solids. The solids were identified as intermediate M2 by FD-MS (field desorption mass spectrometry) analysis.

(3) Synthesis of Compound D-1 (Reaction C)

In a stream of argon, 8.6 g of intermediate M2, 5.9 g of 1,6-dibromo-3,8-diisopropylpyrene which had been synthesized by a known method, 2.5 g of sodium tert-butoxide, 150 mg of palladium acetate (II) [$Pd(OAc)_2$], 135 mg of tri-tert-butylphosphine and 90 mL of dehydrated toluene were put in a 300 mL-recovery flask. A reaction was conducted at 85° C. for 7 hours.

The reaction solution was filtered, and a crude product obtained was purified by silica gel chlormatography (toluene). Solids obtained were recrystallized from toluene, and solids obtained were dried under reduced pressure, whereby 9.3 g of yellowish white solids were obtained. Analysis by FD-MS (field disorption mass spectrometery) was conducted for the compound obtained. The UV absorption maximum wavelength λmax and the flurescence emission maximum wavelength λmax in the toluene solution are given below.

FDMS, calcd for $C_{58}H_{44}N_2O_2$=800. found m/z=(M+).

UV(PhMe); λmax=419 nm, FL(PhMe, λex=390 nm); λmax=452 nm

Production Example 2

Aromatic amine derivative D-2 was produced as follows:

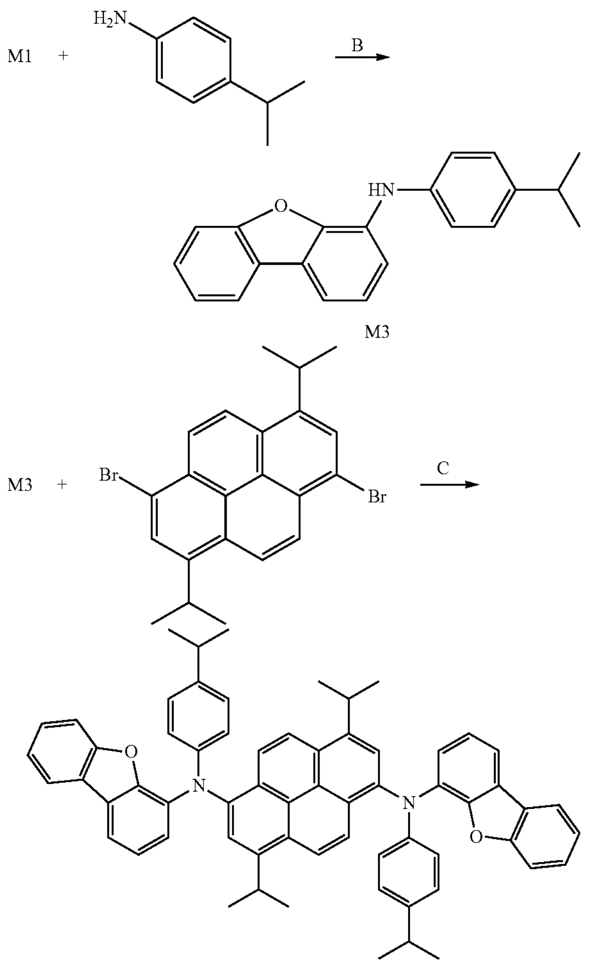

D-2

(1) Synthesis of Intermediate M3 (Reaction B)

An intermediate was synthesized in the same manner as in the synthesis of intermediate M2, except that 4-isopropylaniline was used instead of aniline. The intermediate obtained was identified as intermediate M3 by FD-MS (field desorption mass spectrometry) analysis.

(2) Synthesis of Compound D-2 (Reaction C)

A compound was synthesized in the same manner as in the synthesis of compound D-1, except that intermediate M3 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{64}H_{56}N_2O_2$=884. found m/z=884 (M+).

UV(PhMe); λmax=425 nm, FL(PhMe, λex=400 nm); λmax=457 nm

Production Example 3

Aromatic amine derivative D-3 was produced as follows:

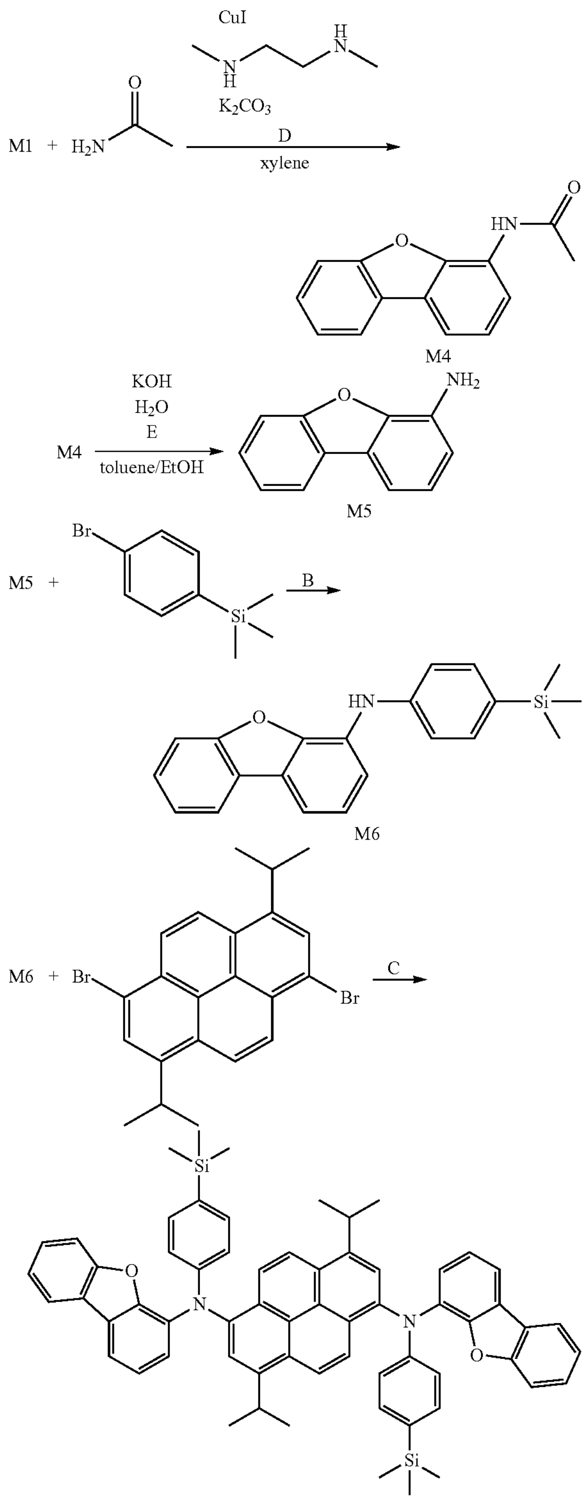

D-3

(1) Synthesis of Intermediate M4 (Reaction D)

In a stream of argon, 18.7 g of intermediate M1, 3.4 g of acetoamide, 0.81 of copper iodide (I), 15.7 g of potassium carbonate and 90 mL of xylene were put in a 300 mL-recovery flask. After stirring, 0.9 mL of N,N'-dimethylethylenediamine was put, and a reaction was conducted at 170° C. for 18 hours.

The reaction solution was filtered, and a crude product obtained was washed with toluene, clean water and methanol. Solids obtained were dried under reduced pressure, whereby 8.2 g of solids were obtained. The solids obtained were identified as intermediate M4 by FD-MS (field desorption mass spectrometry) analysis.

(2) Synthesis of Intermediate M5 (Reaction E)

8.2 g of intermediate M4, 12.2 g of potassium hydroxide, 14 mL of clean water, 37 mL of toluene and 74 mL of ethanol were put in a 300 mL-recovery flask. A reaction was conducted at 110° C. for 8 hours.

The reaction solution was separated and extracted by adding ethyl acetate, and then the organic phase was washed with clean water and saturated saline and dried with sodium sulfate, and concentrated to obtain a crude product. The crude product was purified with silica gel chromatography (ethyl acetate/hexane (1/1)), and solids obtained were dried under reduced pressure to obtain 6.6 g of white solids. The solids were identified as intermediate M5 by FD-MS (field desorption mass spectrometry) analysis.

(3) Synthesis of Intermediate M6 (Reaction B)

An intermediate was synthesized in the same manner as in the synthesis of intermediate M2, except that intermediate M5 was used instead of aniline and 1-bromo-4-(trimethylsilyl)benzene was used instead of intermediate M1. The intermediate obtained was identified as intermediate M6 by FD-MS (field desorption mass spectrometry) analysis.

(4) Synthesis of Compound D-3 (Reaction C)

A compound was synthesized in the same manner as in the synthesis of D-1, except that intermediate M6 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{64}H_{60}N_2O_2Si_2$=944. found m/z=944 (M+).

UV(PhMe); λmax=419 nm, FL(PhMe, λex=390 nm); λmax=452 nm

Production Example 4

Synthesis of Compound D-29 (Reaction C)

Aromatic amine derivative D-29 was produced as follows:

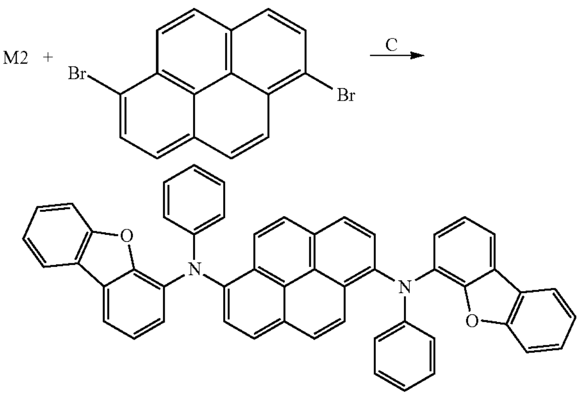

D-29

A compound was synthesized in the same manner as in the synthesis of D-1, except that 1,6-dibromopyrene was used instead of 1,6-dibromo-3,8-diisopropylpyrene. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{52}H_{32}N_2O_2$=716. found m/z=716 (M+).

UV(PhMe); λmax=420 nm, FL(PhMe, λex=390 nm); λmax=449 nm

Production Example 5

Synthesis of Compound D-30 (Reaction C)

Aromatic amine derivative D-30 was produced as follows:

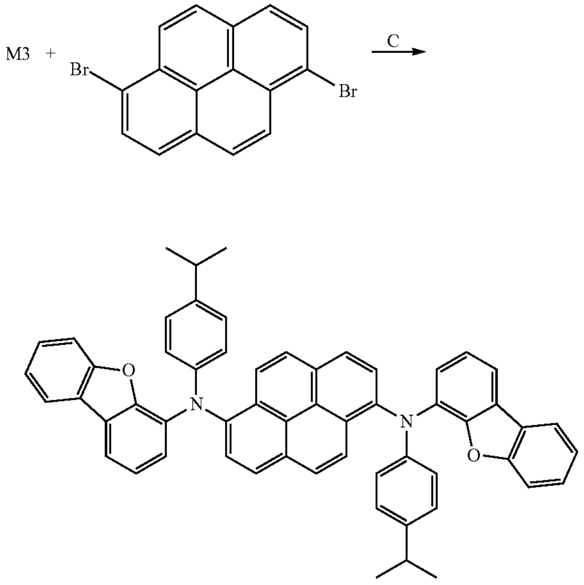

D-30

A compound was synthesized in the same manner as in the synthesis of D-1, except that 1,6-dibromopyrene was used instead of 1,6-dibromo-3,8-diisopropylpyrene and intermediate M3 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{58}H_{44}N_2O_2$=800. found m/z=800 (M+).

UV(PhMe); λmax=426 nm, FL(PhMe, λex=400 nm); λmax=455 nm

Production Example 6

Synthesis of Compound D-32

Aromatic amine derivative D-32 was produced as follows:

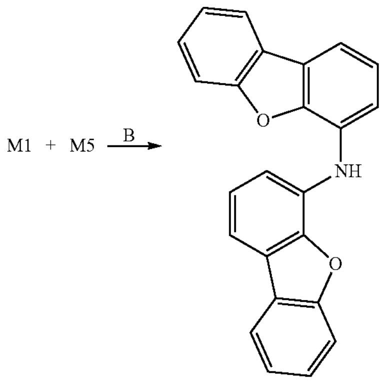

M7

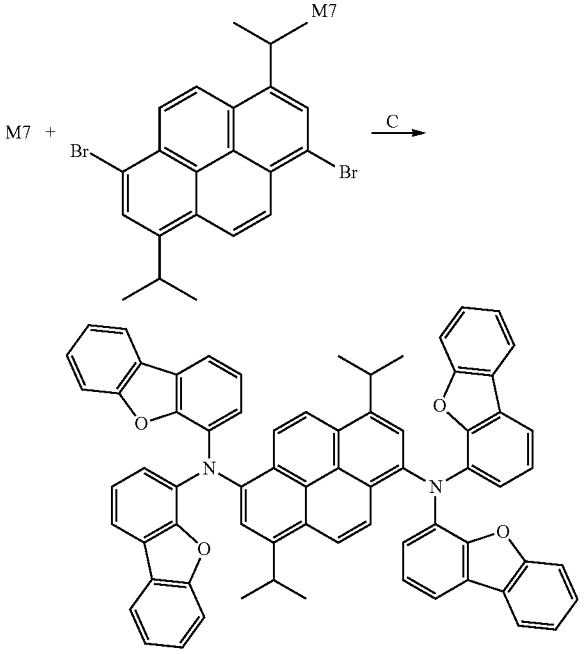

D-32

(1) Synthesis of Intermediate M7 (Reaction B)

An intermediate was synthesized in the same manner as in the synthesis of intermediate M2, except that intermediate M5 was used instead of aniline. The intermediate obtained was identified as intermediate M7 by FD-MS (field desorption mass spectrometry) analysis.

(2) Synthesis of Compound D-32 (Reaction C)

A compound was synthesized in the same manner as in the synthesis of D-1, except that intermediate M7 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{70}H_{48}N_2O_2$=980. found m/z=980 (M+).

UV(PhMe); λmax=419 nm, FL(PhMe, λex=390 nm); λmax=448 nm

Production Example 7

Synthesis of Compound D-46

Aromatic amine derivative D-46 was produced as follows:

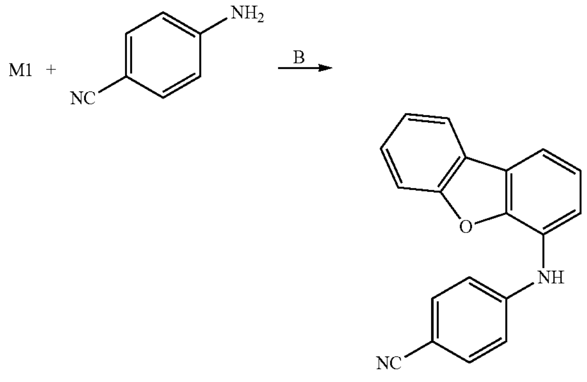

M8

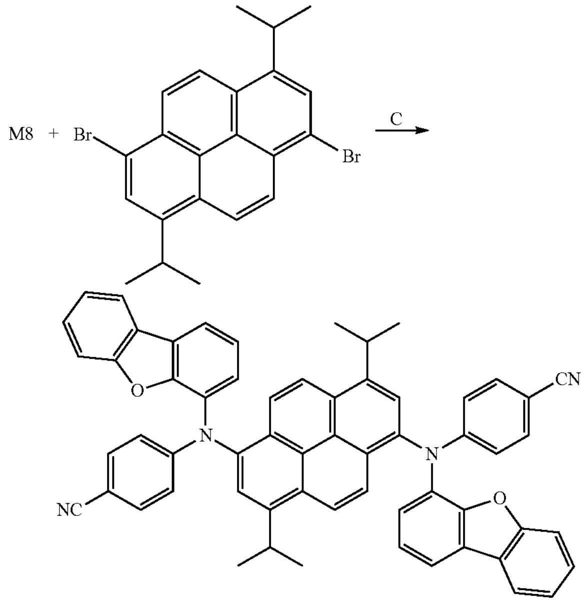

D-46

(1) Synthesis of Intermediate M8 (Reaction B)

An intermediate was synthesized in the same manner as in the synthesis of intermediate M2, except that 4-aminobenzonitrile was used instead of aniline. The intermediate obtained was identified as intermediate M8 by FD-MS (field desorption mass spectrometry) analysis.

(2) Synthesis of Compound D-46 (Reaction C)

A compound was synthesized in the same manner as in the synthesis of D-1, except that intermediate M8 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{60}H_{42}N_4O_2$=850. found m/z=850 (M+).

UV(PhMe); λmax=398 nm, FL(PhMe, λex=370 nm); λmax=444 nm

Production Example 8

Synthesis of Compound D-53

Aromatic amine derivative D-53 was produced as follows.

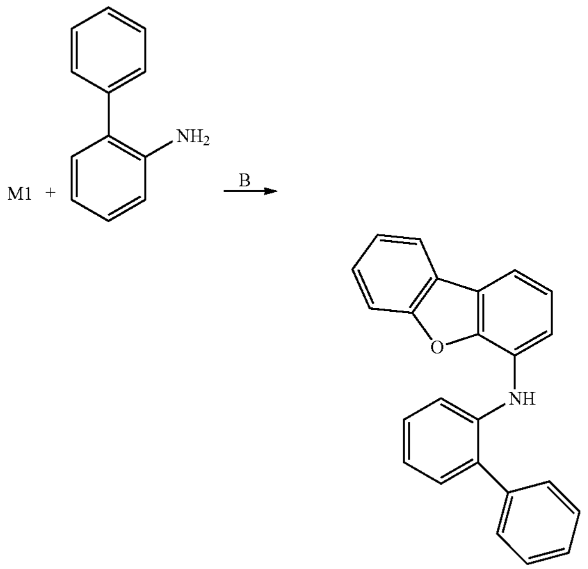

M9

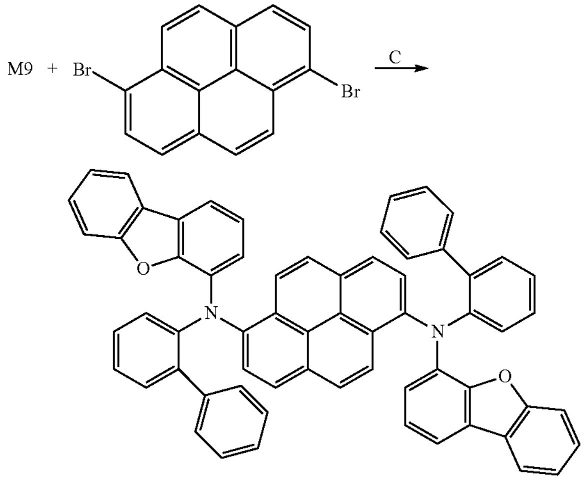

D-53

(1) Synthesis of Intermediate M9 (Reaction B)

An intermediate was synthesized in the same manner as in the synthesis of intermediate M2, except that o-biphenylamine was used instead of aniline. The intermediate obtained was identified as intermediate M9 by FD-MS (field desorption mass spectrometry) analysis.

(2) Synthesis of Compound D-53 (Reaction C)

A compound was synthesized in the same manner as in the synthesis of D-1, except that intermediate M9 was used instead of intermediate M2 and 1,6-dibromopyrene was used instead of 1,6-dibromo-3,8-diisopropylpyrene. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{60}H_{40}N_2O_2$=868. found m/z=868 (M+).

UV(PhMe); λmax=429 nm, FL(PhMe, λex=400 nm); λmax=452 nm

Production Example 9

Synthesis of Compound D-54

Aromatic amine derivative D-54 was produced as follows:

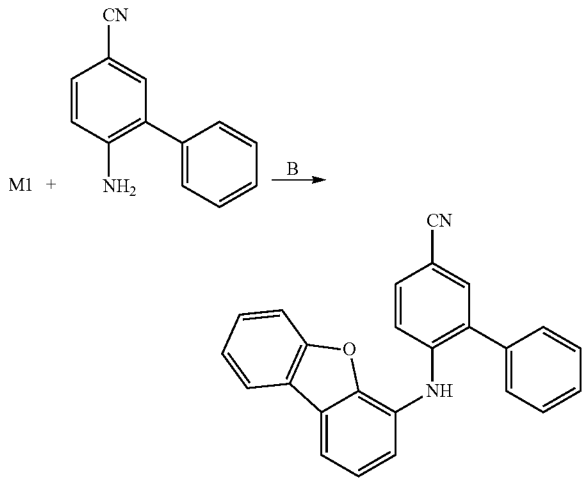

M10

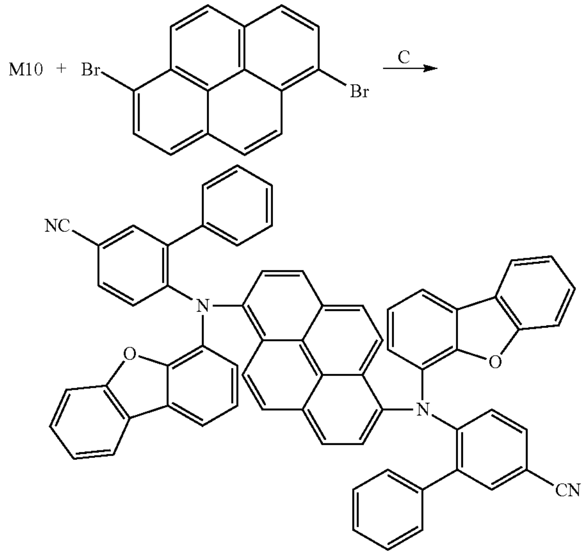

D-54

(1) Synthesis of Intermediate M10 (Reaction B)

An intermediate was synthesized in the same manner as in the synthesis of intermediate M2, except that 4-amino-3-phenylbenzonitrile was used instead of aniline. The intermediate obtained was identified as intermediate M10 by FD-MS (field desorption mass spectrometry) analysis.

(2) Synthesis of Compound D-54 (Reaction C)

A compound was synthesized in the same manner as in the synthesis of D-1, except that 1,6-dibromopyrene was used instead of 1,6-dibromo-3,8-diisopropylpyrene and intermediate M10 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{66}H_{38}N_4O_2$=918. found m/z=918 (M+).

UV(PhMe); λmax=424 nm, FL(PhMe, λex=400 nm); λmax=449 nm

Production Example 10

Synthesis of Compound D-68 (Reaction C)

Aromatic amine derivative D-68 was produced as follows:

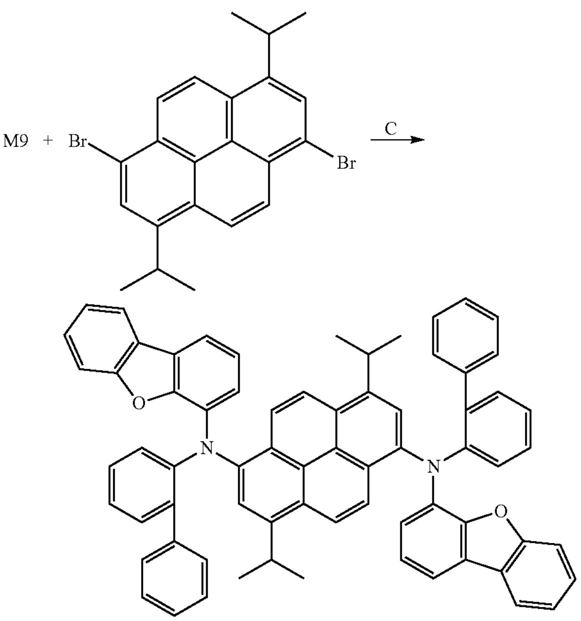

D-68

A compound was synthesized in the same manner as in the synthesis of D-1, except that intermediate M9 was used instead of intermediate M2. Analysis by FD-MS (field disorption mass spectrometery) was conducted for the compound obtained. The UV absorption maximum wavelength λmax and the flurescence emission maximum wavelength in the toluene solution are given below.

FDMS, calcd for $C_{70}H_{52}N_2O_2$=952. found m/z=952 (M+).

UV(PhMe); λmax=432 nm, FL(PhMe, λex=400 nm); λmax=456 nm

Production Example 11

Synthesis of Compound D-76

Aromatic amine derivative D-76 was produced as follows:

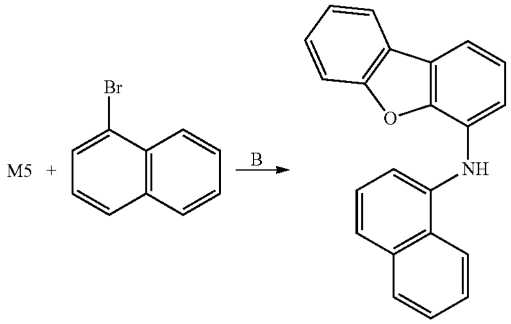

M11

-continued

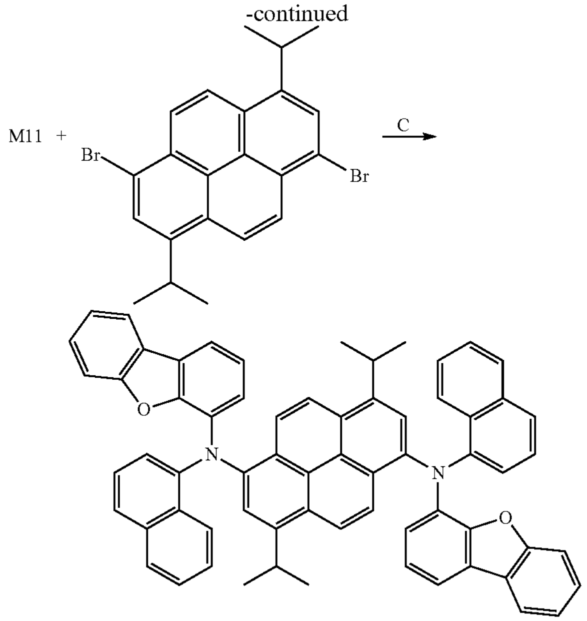

D-76

(1) Synthesis of Intermediate M11 (Reaction B)

An intermediate was synthesized in the same manner as in the synthesis of intermediate M2, except that intermediate M5 was used instead of aniline and 1-bromonaphthalene was used instead of intermediate M1. The intermediate obtained was identified as intermediate M11 by FD-MS (field desorption mass spectrometry) analysis.

(2) Synthesis of Compound D-76 (Reaction C)

A compound was synthesized in the same manner as in the synthesis of D-1, except that intermediate M11 was used instead of intermediate M2. Analysis by FD-MS (field disorption mass spectrometery) was conducted for the compound obtained. The UV absorption maximum wavelength λmax and the fluresœnce emission maximum wavelength in the toluene solution are given below.

FDMS, calcd for $C_{66}H_{48}N_2O_2$=900. found m/z=900 (M+).

UV(PhMe); λmax=424 nm, FL(PhMe, λex=400 nm); λmax=451 nm

Production Example 12

Synthesis of Compound D-81 (Reaction C)

Aromatic amine derivative D-81 was produced as follows:

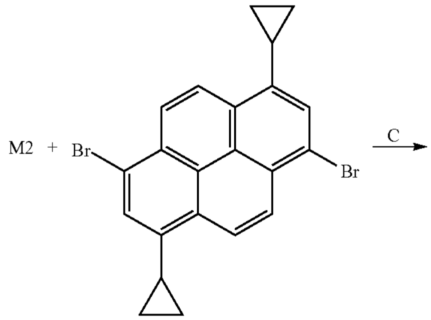

-continued

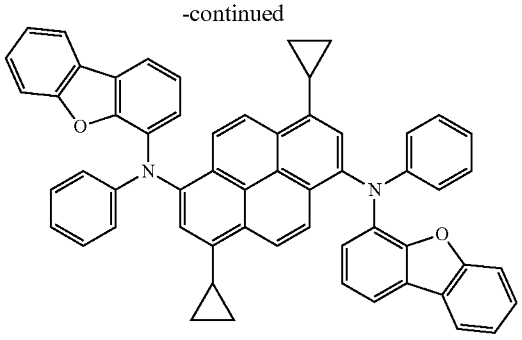

D-81

A compound was synthesized in the same manner as in the synthesis of D-1, except that 1,6-dibromo-3,8-dicyclopropylpyrene was used instead of 1,6-dibromo-3,8-diisopropylpyrene. Analysis by FD-MS (field disorption mass spectrometery) was conducted for the compound obtained. The UV absorption maximum wavelength λmax and the fluresœnce emission maximum wavelength in the toluene solution are given below.

FDMS, calcd for $C_{58}H_{40}N_2O_2$=796. found m/z=796 (M+).

UV(PhMe); λmax=426 nm, FL(PhMe, λex=400 nm); λmax=457 nm

Production Example 13

Synthesis of Compound D-83 (Reaction C)

Aromatic amine derivative D-83 was produced as follows:

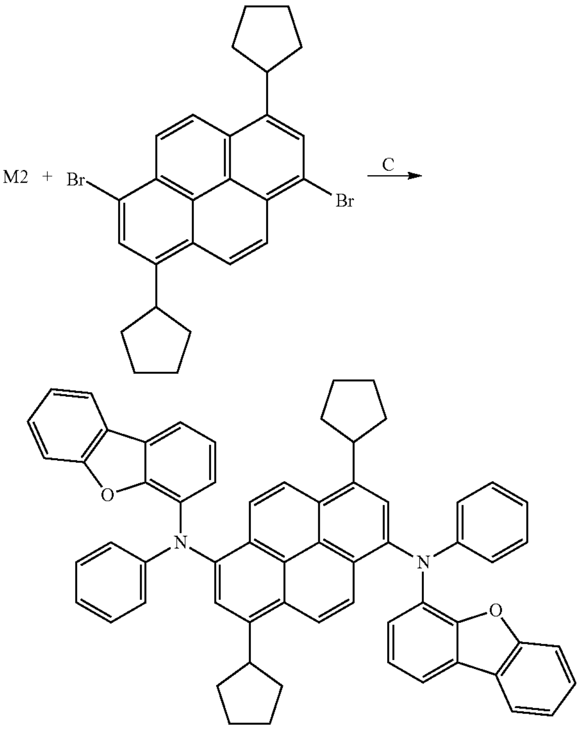

D-83

A compound was synthesized in the same manner as in the synthesis of D-1, except that 1,6-dibromo-3,8-dicyclopentylpyrene was used instead of 1,6-dibromo-3,8-diisopropylpyrene. Analysis by FD-MS (field disorption mass spectrometery) was conducted for the compound obtained. The UV absorption maximum wavelength λmax and the fluresence emission maximum wavelength in the toluene solution are given below.

FDMS, calcd for $C_{62}H_{48}N_2O_2$=852. found m/z=852 (M+).

UV(PhMe); λmax=420 nm, FL(PhMe, λex=390 nm); λmax=453 nm

Production Example 14

Synthesis of Compound D-88 (Reaction C)

Aromatic amine derivative D-88 was produced as follows:

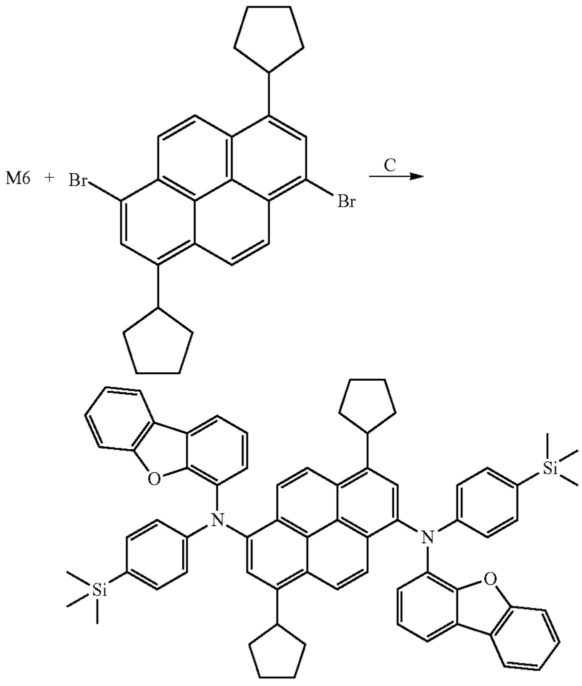

D-88

A compound was synthesized in the same manner as in the synthesis of D-1, except that 1,6-dibromo-3,8-dicyclopentylpyrene was used instead of 1,6-dibromo-3,8-diisopropylpyrene and intermediate M6 was used instead of intermediate M2. Analysis by FD-MS (field disorption mass spectrometery) was conducted for the compound obtained. The UV absorption maximum wavelength λmax and the fluresence emission maximum wavelength in the toluene solution are given below.

FDMS, calcd for $C_{68}H_{64}N_2O_2Si_2$=996. found m/z=996 (M+).

UV(PhMe); λmax=419 nm, FL(PhMe, λex=390 nm); λmax=453 nm

Production Example 15

Synthesis of Compound D-89 (Reaction C)

Aromatic amine derivative D-89 was produced as follows:

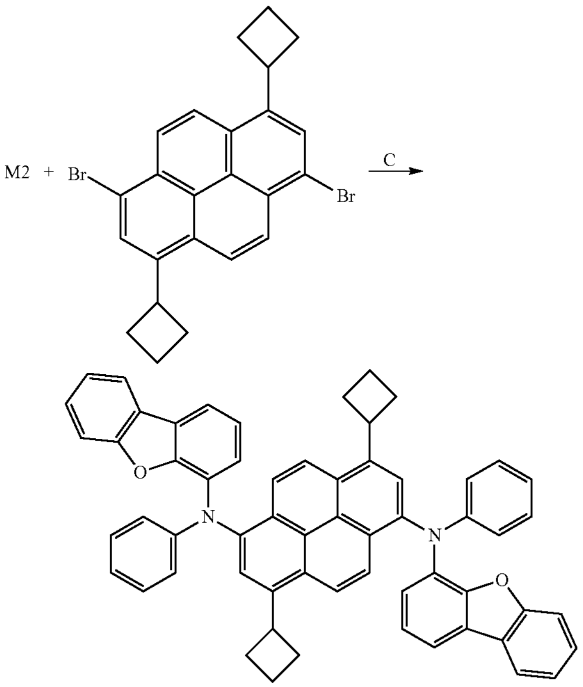

D-89

A compound was synthesized in the same manner as in the synthesis of D-1, except that 1,6-dibromo-3,8-dicyclobutylpyrene was used instead of 1,6-dibromo-3,8-diisopropylpyrene. Analysis by FD-MS (field disorption mass spectrometery) was conducted for the compound obtained. The UV absorption maximum wavelength λmax and the fluresence emission maximum wavelength in the toluene solution are given below.

FDMS, calcd for $C_{60}H_{44}N_2O_2$=824. found m/z=824 (M+).

UV(PhMe); λmax=425 nm, FL(PhMe, λex=400 nm); λmax=456 nm

Production Example 16

Synthesis of Compound D-90 (Reaction C)

Aromatic amine derivative D-90 was produced as follows:

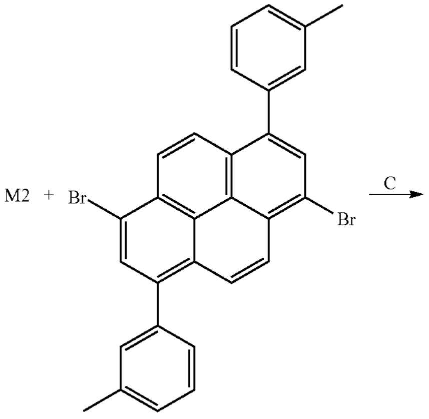

-continued

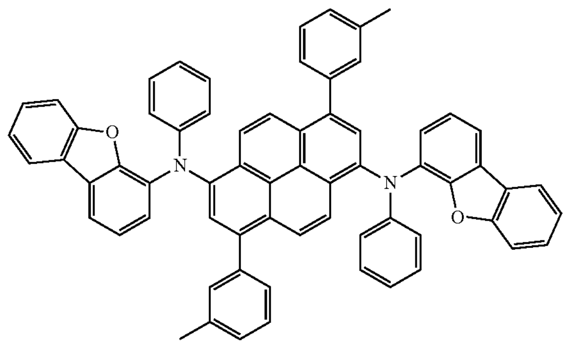

D-90

A compound was synthesized in the same manner as in the synthesis of D-1, except that 1,6-dibromo-3,8-di-m-tolylpyrene was used instead of 1,6-dibromo-3,8-diisopropylpyrene. Analysis by FD-MS (field disorption mass spectrometery) was conducted for the compound obtained. The UV absorption maximum wavelength λmax and the fluresence emission maximum wavelength in the toluene solution are given below.

FDMS, calcd for $C_{66}H_{44}N_2O_2$=896. found m/z=896 (M+).

UV(PhMe); λmax=432 nm, FL(PhMe, λex=400 nm); λmax=468 nm

Production Example 17

Synthesis of Compound D-96

Aromatic amine derivative D-96 was produced as follows:

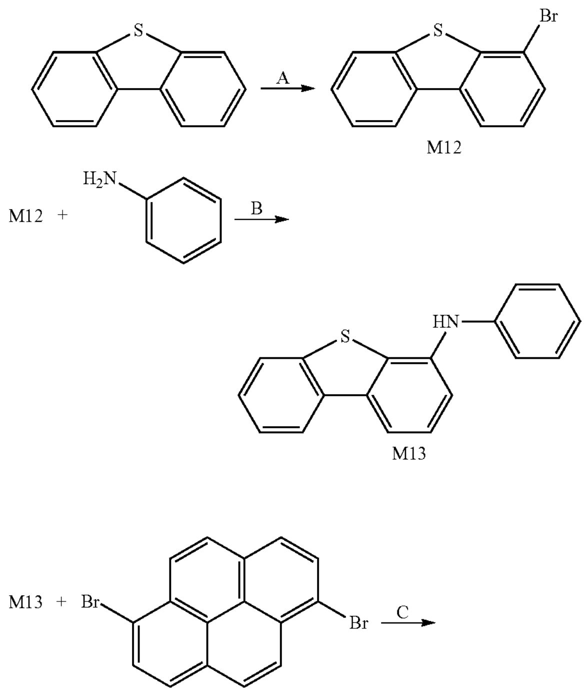

-continued

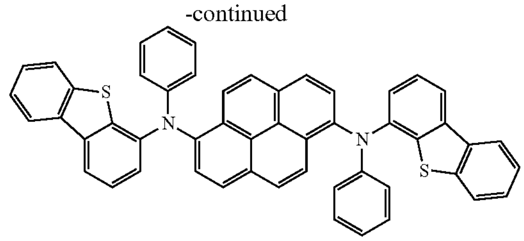

D-96

(1) Synthesis of Intermediate M12 (Reaction A)

An intermediate was synthesized in the same manner as in the synthesis of intermediate M1, except that dibenzothiophene was used instead of dibenzofuran. The intermediate obtained was identified as intermediate M12 by FD-MS (field desorption mass spectrometry) analysis.

(2) Synthesis of Intermediate M13 (Reaction B)

An intermediate was synthesized in the same manner as in the synthesis of intermediate M2, except that intermediate M12 was used instead of intermediate M1. The intermediate obtained was identified as intermediate M13 by FD-MS (field desorption mass spectrometry) analysis.

(3) Synthesis of Compound D-96 (Reaction C)

A compound was synthesized in the same manner as in the synthesis of D-1, except that 1,6-dibromopyrene was used instead of 1,6-dibromo-3,8-diisopropylpyrene and intermediate M13 was used instead of intermediate M2. Analysis by FD-MS (field disorption mass spectrometery) was conducted for the compound obtained. The UV absorption maximum wavelength λmax and the fluresence emission maximum wavelength in the toluene solution are given below.

FDMS, calcd for $C_{52}H_{32}N_2S_2$=748. found m/z=748 (M+).

UV(PhMe); λmax=423 nm, FL(PhMe, λex=400 nm); λmax=455 nm

In Examples 1 to 112 explained below, synthesis was conducted in the same manner as in Production Examples 1 to 15 for compounds of which the production example is not given.

Example 1

On a glass substrate with a dimension of 25×75×1.1 mm, a 120 nm-thick transparent electrode formed of indium tin oxide was provided. This transparent electrode functions as an anode. After subjecting to UV-ozone cleaning, the glass substrate was mounted in a vacuum vapor deposition apparatus.

First, a 60 nm-thick film formed of N',N"-bis[4-(diphenylamino)phenyl]-N',N"-diphenylbiphenyl-4,4'-diamine was deposited as a hole-injecting layer. Then, a 20 nm-thick film formed of N,N,N',N'-tetrakis(4-biphenyl)-4,4'-benzidine was deposited thereon as a hole-transporting layer. Subsequently, anthracene derivative EM2 as a host material and aromatic amine derivative D-1 as a doping material were co-deposited in a mass ratio of 40:2 to form a 40 nm-thick emitting layer.

Next, as an electron-injecting layer, a 20 nm-thick film formed of tris(8-hydroxyquinolinato)aluminum was deposited on this emitting layer.

Then, a 1 nm-thick film formed of lithium fluoride was deposited, and a 150 nm-thick film formed of aluminum was deposited, whereby an organic EL device was fabricated. The aluminum/lithium fluoride layer functions as a cathode.

For the organic EL device thus obtained, device performance (luminous efficiency) at a current density of 10 $mA/cm^2$ and the 1931 CIE (x,y) chromaticity coordinates were measured by the following methods. The results are shown in Table 1.

Luminance: Measured by means of a spectroradiometer (CS-1000, manufactured by Konica Minolta Holdings, Inc.).

The 1931 CIE (x,y) chromaticity coordinates: Measured by means of a spectroradiometer (CS-1000, manufactured by Konica Minolta Holdings, Inc.).

Luminous efficiency (L/J): L/J is the ratio of luminance to current density. Current and voltage were measured by means of SOURCE MEASURE UNIT 236 (manufactured by Keithley Instruments Inc.) and luminance was measured by means of a spectroradiometer. Current density was calculated based on a current value and an emission area, whereby L/J was obtained. Luminous efficiency (lm/W) was obtained by the following formula.

Luminous efficiency (lm/W)=*L/J*/Voltage×Circular constant

Example 2

An organic EL device was fabricated and evaluated in the same manner as in Example 1, except that aromatic amine derivative D-2 was used instead of aromatic amine derivative D-1. The results are shown in Table 1.

Example 3

An organic EL device was fabricated and evaluated in the same manner as in Example 1, except that aromatic amine derivative D-3 was used instead of aromatic amine derivative D-1. The results are shown in Table 1.

Comparative Example 1

An organic EL device was fabricated and evaluated in the same manner as in Example 1, except that the following compound H-1 was used instead of aromatic amine derivative D-1. The results are shown in Table 1.

H-1

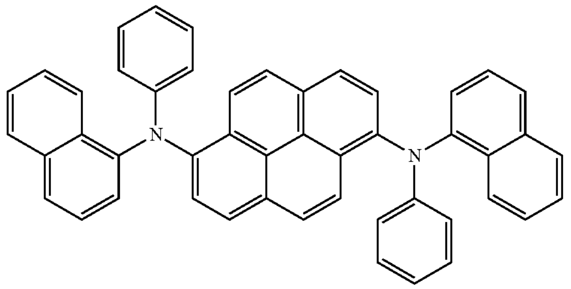

TABLE 1

| | Example 1 | Example 2 | Example 3 | Com. Ex. 1 |
|---|---|---|---|---|
| Host material | EM2 | EM2 | EM2 | EM2 |
| Doping material | D-1 | D-2 | D-3 | H-1 |
| Driving voltage (V) | 6.0 | 5.8 | 5.9 | 6.1 |
| CIEx | 0.139 | 0.131 | 0.133 | 0.133 |
| CIEy | 0.112 | 0.143 | 0.120 | 0.186 |
| Efficiency (lm/W) | 4.0 | 4.2 | 3.9 | 3.2 |

From Table 1, it is apparent that, as compared with the known compound H-1, the dibenzofuran derivative used in Examples contributed to improvement in efficiency and a significant decrease in CIEy value (emitted at a significantly shorter wavelength). The reason therefor is assumed as follows. In the compound of the invention, in the dibenzofuranyl group or the dibenzothiophenyl group, a lone pair of the nitrogen atom exerts influence on the electron density of the aromatic ring which is bonded to the nitrogen atom, and a lone pair of the oxygen atom or the sulfur atom exerts influence on the aromatic ring which is not bonded to the nitrogen atom. As a result, electron-attracting effects of the oxygen atom or the sulfur atom which has larger electronegativity than that of a carbon atom are exhibited in the aromatic ring which is bonded to the nitrogen atom. Therefore, as compared with a compound such as H-1 which has only an aromatic hydrocarbon group, the compound of the invention allows an organic EL device to emit at a shorter wavelength.

Example 4

On a glass substrate with a dimension of 25×75×1.1 mm, a 120 nm-thick transparent electrode formed of indium tin oxide was provided. This transparent electrode functions as an anode. After cleaning by irradiating UV rays and ozone, this substrate was mounted in a vacuum vapor deposition apparatus.

First, a 50 nm-thick film formed of HT-1 having the following structure was deposited as a hole-injecting layer. Then, a 45 nm-thick film formed of N,N,N',N'-tetrakis(4-biphenyl)-4,4'-benzidine was deposited thereon. Subsequently, anthracene derivative EM9 as a host material and aromatic amine derivative D-1 as a doping material were co-deposited in a mass ratio of 25:5 to form a 30 nm-thick emitting layer.

Next, as an electron-injecting layer, a 25 nm-thick film formed of ET-1 having the following structure was deposited on this emitting layer.

Then, a 1 nm-thick film formed of lithium fluoride was deposited, and a 150 nm-thick film formed of aluminum was deposited, whereby an organic EL device was fabricated. The aluminum/lithium fluoride layer functions as a cathode.

The organic EL device thus obtained was evaluated in the same manner as in Example 1. The results are shown in Table 2.

HT-1

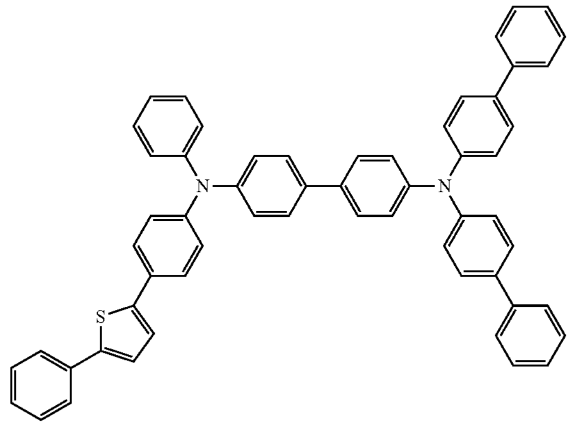

ET-1

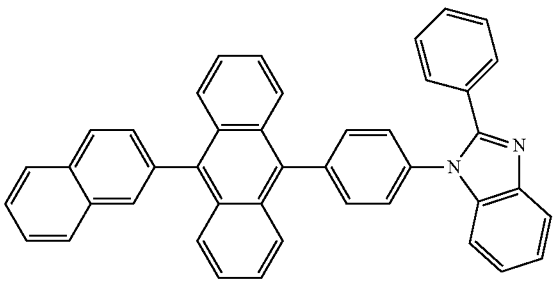

Examples 5 to 42 and Comparative Example 2

Organic EL devices were fabricated and evaluated in the same manner as in Example 4, except that the host material and the doping material were changed to those shown in Table 2. The results are shown in Table 2.

The external quantum yield was measured as follows:

Current with a current density of 10 $mA/cm^2$ was allowed to pass through each of the organic EL devices thus obtained. Emission spectrum was measured by means of a spectroradiometer (CS-1000, manufactured by Konica Minolta Holdings, Inc) and the external quantum yield was calculated by the following expression (1):

Expression (1)

$$E.Q.E = \frac{N_P}{N_F} \times 100 = \frac{\frac{(\pi/10^9)\int \phi(\lambda)\cdot d\lambda}{hc}}{\frac{J/10}{e}} \times 100 = \frac{\frac{(\pi/10^9)\sum(\phi(\lambda)\cdot(\lambda))}{hc}}{\frac{J/10}{e}} \times 100\ (\%)$$

$N_P$: Number of photons
$N_E$: Number of electrons
π: Circular constant=3.1416
λ: Wavelength (nm)
φ: Emission intensity (W/sr·$m^2$·nm)
h: Planck's constant=$6.63\times10^{-34}$ (J·s)
c: Speed of light=$3\times10^8$ (m/s)
J: Current density ($mA/cm^2$)
e: Electric charge=$1.6\times10^{-19}$ (C)

TABLE 2

| Examples | Host material | Doping material | CIEx | CIEy | External quantum yield (%) |
|---|---|---|---|---|---|
| 4 | EM9 | D-1 | 0.136 | 0.100 | 6.3 |
| 5 | EM13 | D-1 | 0.136 | 0.103 | 7.3 |
| 6 | EM28 | D-1 | 0.136 | 0.104 | 7.3 |
| 7 | EM29 | D-1 | 0.136 | 0.103 | 7.2 |
| 8 | EM31 | D-1 | 0.136 | 0.105 | 7.3 |
| 9 | EM32 | D-1 | 0.136 | 0.105 | 7.2 |
| 10 | EM69 | D-1 | 0.136 | 0.104 | 6.8 |
| 11 | EM70 | D-1 | 0.136 | 0.101 | 6.8 |
| 12 | EM73 | D-1 | 0.137 | 0.103 | 6.9 |
| 13 | EM125 | D-1 | 0.137 | 0.106 | 6.5 |
| 14 | EM133 | D-1 | 0.137 | 0.107 | 6.5 |
| 15 | EM364 | D-1 | 0.139 | 0.118 | 6.2 |
| 16 | EM367 | D-1 | 0.135 | 0.104 | 6.7 |
| 17 | EM9 | D-2 | 0.128 | 0.130 | 6.5 |
| 18 | EM13 | D-2 | 0.128 | 0.133 | 7.2 |
| 19 | EM28 | D-2 | 0.128 | 0.134 | 7.2 |
| 20 | EM29 | D-2 | 0.128 | 0.133 | 7.1 |
| 21 | EM31 | D-2 | 0.128 | 0.135 | 7.2 |
| 22 | EM32 | D-2 | 0.128 | 0.135 | 7.1 |
| 23 | EM69 | D-2 | 0.128 | 0.134 | 6.9 |
| 24 | EM70 | D-2 | 0.128 | 0.131 | 6.8 |
| 25 | EM73 | D-2 | 0.129 | 0.133 | 6.8 |
| 26 | EM125 | D-2 | 0.129 | 0.136 | 6.6 |
| 27 | EM133 | D-2 | 0.129 | 0.137 | 6.6 |
| 28 | EM364 | D-2 | 0.131 | 0.148 | 6.3 |
| 29 | EM367 | D-2 | 0.127 | 0.134 | 6.7 |
| 30 | EM9 | D-3 | 0.130 | 0.108 | 6.4 |
| 31 | EM13 | D-3 | 0.131 | 0.111 | 7.3 |
| 32 | EM28 | D-3 | 0.131 | 0.112 | 7.3 |
| 33 | EM29 | D-3 | 0.131 | 0.111 | 7.2 |
| 34 | EM31 | D-3 | 0.131 | 0.113 | 7.3 |
| 35 | EM32 | D-3 | 0.131 | 0.113 | 7.2 |
| 36 | EM69 | D-3 | 0.130 | 0.112 | 7.1 |
| 37 | EM70 | D-3 | 0.130 | 0.109 | 6.9 |
| 38 | EM73 | D-3 | 0.131 | 0.111 | 6.9 |
| 39 | EM125 | D-3 | 0.131 | 0.114 | 6.7 |
| 40 | EM133 | D-3 | 0.131 | 0.115 | 6.7 |
| 41 | EM364 | D-3 | 0.133 | 0.126 | 6.3 |
| 42 | EM367 | D-3 | 0.130 | 0.112 | 6.7 |
| Com. Ex. 2 | EM2 | H-1 | 0.133 | 0.185 | 5.9 |

Examples 43 to 71 and Comparative Example 3

Organic EL devices were fabricated and evaluated in the same manner as in Example 1, except that the host material and the doping material were changed to those shown in Table 3. The results are shown in Table 3.

The external quantum yield was measured by the same method as mentioned above.

H-2

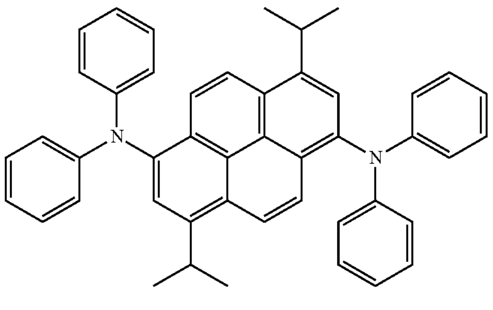

TABLE 3

| Examples | Host material | Doping material | Voltage (V) | CIEx | CIEy | External quantum yield (%) |
|---|---|---|---|---|---|---|
| 43 | EM2 | D-1 | 6.0 | 0.139 | 0.112 | 6.2 |
| 44 | EM2 | D-2 | 5.8 | 0.131 | 0.143 | 6.8 |
| 45 | EM2 | D-3 | 5.9 | 0.133 | 0.120 | 6.4 |
| 46 | EM2 | D-10 | 5.8 | 0.134 | 0.151 | 6.9 |
| 47 | EM2 | D-16 | 5.8 | 0.135 | 0.158 | 6.7 |
| 48 | EM2 | D-17 | 6.1 | 0.135 | 0.150 | 6.5 |
| 49 | EM2 | D-29 | 6.0 | 0.132 | 0.110 | 6.1 |
| 50 | EM2 | D-30 | 5.8 | 0.136 | 0.134 | 6.6 |
| 51 | EM2 | D-32 | 6.1 | 0.131 | 0.110 | 6.0 |
| 52 | EM2 | D-35 | 5.9 | 0.133 | 0.135 | 6.7 |
| 53 | EM2 | D-36 | 5.9 | 0.133 | 0.121 | 6.5 |
| 54 | EM2 | D-37 | 6.1 | 0.132 | 0.140 | 6.5 |
| 55 | EM2 | D-38 | 6.0 | 0.138 | 0.114 | 6.2 |
| 56 | EM2 | D-42 | 6.0 | 0.130 | 0.129 | 6.8 |
| 57 | EM2 | D-46 | 5.8 | 0.129 | 0.102 | 6.1 |
| 58 | EM2 | D-50 | 5.8 | 0.129 | 0.094 | 6.1 |
| 59 | EM2 | D-53 | 6.0 | 0.137 | 0.125 | 6.7 |
| 60 | EM2 | D-54 | 6.0 | 0.137 | 0.122 | 6.9 |
| 61 | EM2 | D-59 | 6.1 | 0.132 | 0.093 | 5.9 |
| 62 | EM2 | D-65 | 6.0 | 0.132 | 0.110 | 6.1 |
| 63 | EM2 | D-68 | 6.0 | 0.137 | 0.130 | 6.6 |
| 64 | EM2 | D-76 | 6.1 | 0.131 | 0.131 | 6.0 |
| 65 | EM2 | D-83 | 6.0 | 0.139 | 0.114 | 6.1 |
| 66 | EM2 | D-84 | 6.0 | 0.137 | 0.120 | 6.5 |
| 67 | EM2 | D-85 | 6.0 | 0.137 | 0.099 | 6.0 |
| 68 | EM2 | D-86 | 6.0 | 0.130 | 0.125 | 6.8 |
| 69 | EM2 | D-88 | 6.0 | 0.139 | 0.114 | 6.3 |
| 70 | EM2 | D-90 | 5.7 | 0.139 | 0.169 | 7.0 |
| 71 | EM2 | D-94 | 5.9 | 0.135 | 0.165 | 6.8 |
| Com. Ex. 3 | EM2 | H-2 | 5.9 | 0.137 | 0.180 | 4.1 |

Example 72

A glass substrate (GEOMATEC CO., LTD.) of 25 mm×75 mm×1.1 mm with an ITO transparent electrode (anode) was subjected to ultrasonic cleaning with isopropyl alcohol for 5 minutes, and cleaned with ultraviolet rays and ozone for 30 minutes. The resultant glass substrate with transparent electrode lines was mounted on a substrate holder in a vacuum vapor deposition apparatus. First, compound A-1 shown below was formed into a film in a thickness of 50 nm on the surface of the transparence electrode on which the transparence electrode lines were formed so as to cover the transparent electrode. Subsequent to the formation of the A-1 film, compound A-2 shown below was formed thereon into a film in a thickness of 45 nm.

Further, on this A-2 film, compound EM31 as a host material and compound D-1 of the invention as a doping material were formed into a film in a thickness of 25 nm with a film thickness ratio of 20:1, whereby a blue emitting layer was formed.

On this film, as an electron-transporting layer, ET-2 having the following structure was formed into a 25 nm-thick film by deposition. Thereafter, LiF was formed into a 1 nm-thick film. Metal Al was deposited in a thickness of 150 nm as a metal cathode, thereby fabricating an organic EL device.

The resulting organic emitting device was evaluated in the same manner as in Example 1. The external quantum yield was measured by the same method as mentioned above. The results are shown in Table 4.

A-1

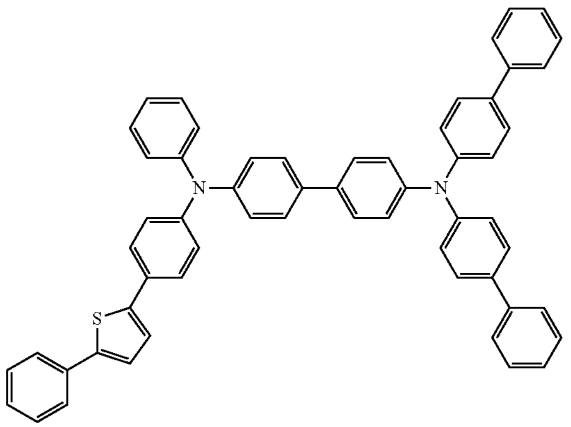

A-2

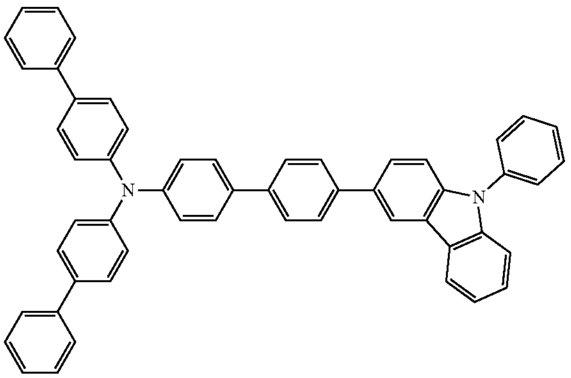

ET-2

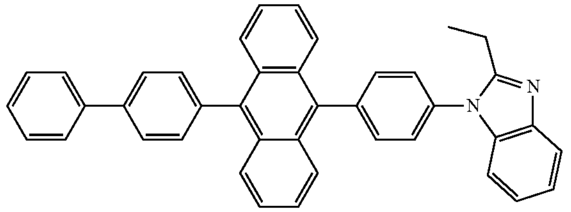

Examples 73 to 112 and Comparative Examples 4 and 5

Organic EL devices were fabricated and evaluated in the same manner as in Example 72, except that the host material and the doping material were changed to those shown in Table 4. The external quantum yield was measured by the same method as mentioned above. The results are shown in Table 4.

EMP1

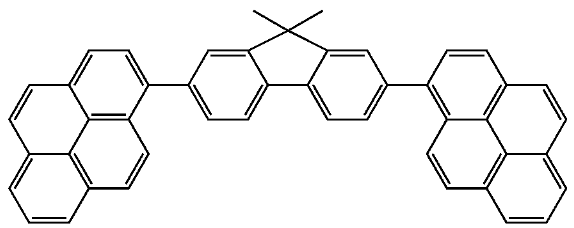

TABLE 4

| Examples | Host material | Doping material | Voltage (V) | CIEx | CIEy | External quantum yield (%) |
|---|---|---|---|---|---|---|
| 72 | EM31 | D-1 | 3.6 | 0.138 | 0.095 | 8.0 |
| 73 | EM31 | D-2 | 3.5 | 0.138 | 0.120 | 8.2 |
| 74 | EM31 | D-29 | 3.6 | 0.137 | 0.093 | 7.6 |
| 75 | EM31 | D-30 | 3.5 | 0.139 | 0.108 | 7.8 |
| 76 | EM31 | D-38 | 3.6 | 0.138 | 0.100 | 7.9 |
| 77 | EM31 | D-42 | 3.6 | 0.138 | 0.116 | 8.1 |
| 78 | EM31 | D-46 | 3.4 | 0.137 | 0.084 | 7.2 |
| 79 | EM31 | D-50 | 3.4 | 0.137 | 0.080 | 7.0 |
| 80 | EM31 | D-53 | 3.6 | 0.138 | 0.100 | 8.1 |
| 81 | EM31 | D-54 | 3.5 | 0.138 | 0.098 | 7.8 |
| 82 | EM31 | D-65 | 3.6 | 0.139 | 0.101 | 7.9 |
| 83 | EM31 | D-68 | 3.6 | 0.138 | 0.105 | 8.1 |
| 84 | EM31 | D-83 | 3.5 | 0.137 | 0.102 | 8.0 |
| 85 | EM31 | D-85 | 3.6 | 0.137 | 0.102 | 7.9 |
| 86 | EM31 | D-86 | 3.6 | 0.138 | 0.114 | 8.1 |
| 87 | EM31 | D-90 | 3.4 | 0.140 | 0.159 | 7.7 |
| 88 | EM116 | D-1 | 3.6 | 0.137 | 0.090 | 7.4 |
| 89 | EM116 | D-2 | 3.6 | 0.138 | 0.110 | 7.8 |
| 90 | EM116 | D-29 | 3.7 | 0.138 | 0.088 | 7.0 |
| 91 | EM116 | D-30 | 3.6 | 0.139 | 0.100 | 7.4 |
| 92 | EM116 | D-38 | 3.5 | 0.138 | 0.096 | 7.5 |
| 93 | EM116 | D-42 | 3.6 | 0.138 | 0.102 | 7.5 |
| 94 | EM116 | D-46 | 3.7 | 0.138 | 0.080 | 6.8 |
| 95 | EM116 | D-50 | 3.6 | 0.137 | 0.079 | 6.6 |
| 96 | EM116 | D-53 | 3.6 | 0.137 | 0.097 | 7.4 |
| 97 | EM116 | D-54 | 3.7 | 0.138 | 0.090 | 7.4 |
| 98 | EM116 | D-65 | 3.6 | 0.138 | 0.097 | 7.5 |
| 99 | EM116 | D-68 | 3.6 | 0.138 | 0.101 | 7.7 |
| 100 | EM116 | D-83 | 3.6 | 0.138 | 0.096 | 7.5 |
| 101 | EM116 | D-85 | 3.7 | 0.139 | 0.095 | 7.4 |
| 102 | EM116 | D-86 | 3.6 | 0.139 | 0.104 | 7.7 |
| 103 | EM116 | D-90 | 3.5 | 0.138 | 0.145 | 7.3 |
| 104 | EM205 | D-1 | 3.6 | 0.138 | 0.096 | 8.1 |
| 105 | EM205 | D-2 | 3.6 | 0.137 | 0.122 | 8.2 |
| 106 | EM205 | D-46 | 3.5 | 0.138 | 0.088 | 7.4 |
| 107 | EM205 | D-50 | 3.5 | 0.137 | 0.081 | 7.1 |
| 108 | EM205 | D-53 | 3.6 | 0.138 | 0.100 | 8.2 |
| 109 | EM205 | D-54 | 3.6 | 0.138 | 0.100 | 8.0 |
| 110 | EM205 | D-68 | 3.6 | 0.138 | 0.104 | 8.1 |
| 111 | EM205 | D-83 | 3.6 | 0.139 | 0.103 | 8.2 |
| 112 | EMP1 | D-1 | 3.2 | 0.143 | 0.115 | 6.8 |
| Com. Ex. 4 | EMP1 | H-2 | 3.2 | 0.143 | 0.201 | 5.8 |
| Com. Ex. 5 | EM31 | H-2 | 3.6 | 0.137 | 0.178 | 5.2 |

From Tables 1 to 4, it can be understood that the devices of Examples maintained high efficiency and exhibited high color reproducibility. As a result, the invention can realize a display device which exhibit high color reproducibility at low power consumption.

INDUSTRIAL APPLICABILITY

The organic EL device of the invention can be suitably used as a planar emitting body such as a flat panel display of a wall-hanging television, backlight of a copier, a printer, or a liquid crystal display, light sources for instruments, a display panel, a navigation light, and the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An organic electroluminescence device comprising one or more organic thin film layers comprising an emitting layer between an anode and a cathode, wherein at least one layer of the one or more organic thin film layers comprises:

an aromatic amine derivative represented by the following formula (A1):

(A1)

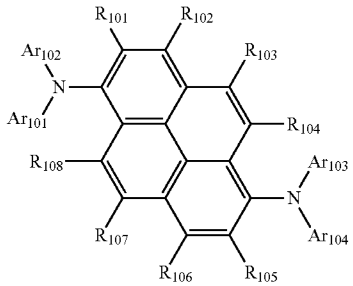

wherein $R_{101}$ to $R_{108}$ are independently a hydrogen atom, a halogen atom, a substituted or unsubstituted alkyl group having 1 to 20 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms or a cyano group, and $Ar_{101}$ to $Ar_{104}$ are independently a substituted or unsubstituted aryl group having 6 to 30 ring carbon atoms or a substituted or unsubstituted heterocyclic group having 5 to 30 ring atoms, provided that at least one of $Ar_{101}$ to $Ar_{104}$ is a heterocyclic group represented by the following formula (A2):

(A2)

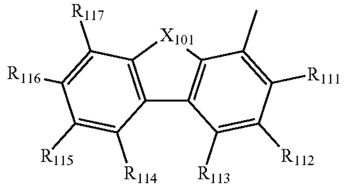

wherein $R_{111}$ to $R_{117}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted alkylsilyl group having 3 to 30 carbon atoms, a substituted or unsubstituted arylsilyl group having 8 to 30 ring carbon atoms, a cyano group, a substituted or unsubstituted aryl group having 6 to 20 ring carbon atoms or a substituted or unsubstituted heterocyclic group having 5 to 20 ring atoms, adjacent substituents of $R_{11}$ to $R_{117}$ may be bonded to each other to form a saturated or unsaturated ring, and $X_{101}$ is an oxygen atom or a sulfur atom; and an anthracene derivative represented by the following formula (5):

(5)

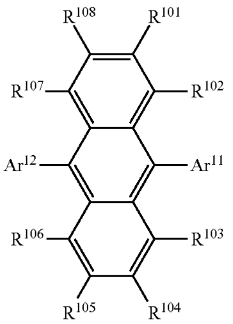

wherein $Ar^{11}$ and $Ar^{12}$ are independently a substituted or unsubstituted monocyclic group having 5 to 50 ring atoms, a substituted or unsubstituted fused ring group having 8 to 50 ring atoms, or a group formed by combination of the monocyclic group and the fused ring group, provided that at least one of $Ar^{11}$ and $Ar^{12}$ is a substituted or unsubstituted dibenzofuranyl group, and $R^{101}$ to $R^{108}$ are independently a hydrogen atom, a halogen atom, or a group selected from the group consisting of a substituted or unsubstituted monocyclic group having 5 to 50 ring atoms, a substituted or unsubstituted fused ring group having 8 to 50 ring atoms, a group formed by combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group and a cyano group.

2. The organic electroluminescence device according to claim 1, wherein the aromatic amine derivative is represented by the following formula (A3):

wherein $R_{101}$ to $R_{108}$, $Ar_{102}$ and $Ar_{104}$ are the same as those in formula (A1), $R_{121}$ to $R_{127}$ and $R_{131}$ to $R_{137}$ are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted alkylsilyl group having 3 to 30 carbon atoms, a substituted or unsubstituted arylsilyl group having 8 to 30 ring carbon atoms, a cyano group, a substituted or unsubstituted aryl group having 6 to 20 ring carbon atoms or a substituted or unsubstituted heterocyclic group having 5 to 20 ring atoms, adjacent substituents of $R_{121}$ to $R_{127}$ and $R_{131}$ to $R_{137}$ may be bonded to each other to form a saturated or unsaturated ring, and $X_{102}$ and $X_{103}$ are independently an oxygen atom or a sulfur atom.

3. The organic electroluminescence device according to claim 2 wherein in the formula (A3), $Ar_{102}$ and $Ar_{104}$ are a heterocyclic group represented by the following formula (A4):

(A4)

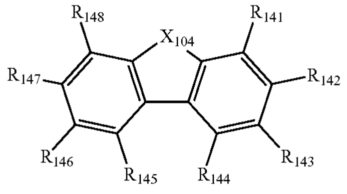

wherein one of $R_{141}$ to $R_{148}$ is used for connection to the nitrogen atom, and the others are independently a hydrogen atom, a halogen atom, a substituted or unsubstituted alkyl group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted alkylsilyl group having 3 to 30 carbon atoms, a substituted or unsubstituted arylsilyl group having 8 to 30 ring carbon atoms, a cyano group, a substituted or unsubstituted aryl group having 6 to 20 ring carbon atoms, or a substituted or unsubstituted heterocyclic group having 5 to 20 ring atoms, adjacent substituents of $R_{141}$ to $R_{148}$ may be bonded to each other to form a saturated or unsaturated ring, and $X_{104}$ is an oxygen atom or a sulfur atom.

(A3)

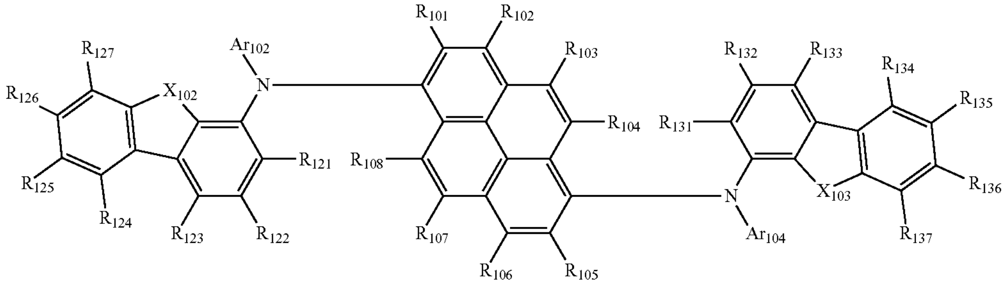

4. The organic electroluminescence device according to claim 1 wherein in the formula (A1), $R_{101}$ to $R_{108}$ are a hydrogen atom.

5. The organic electroluminescence device according to claim 4 wherein in the formula (A1), $R_{102}$ is a substituted or unsubstituted alkyl group having 1 to 20 carbon atoms, a substituted or unsubstituted cycloalkyl group having 3 to 10 carbon atoms or a substituted or unsubstituted alkylsilyl group having 3 to 30 carbon atoms, and $R_{101}$ and $R_{103}$ to $R_{108}$ are a hydrogen atom.

6. The organic electroluminescence device according to claim 1 wherein in the formula (A1), $R_{102}$ and $R_{106}$ are a substituted or unsubstituted alkyl group having 1 to 20 carbon atoms, a substituted or unsubstituted cycloalkyl group having 3 to 10 carbon atoms, or a substituted or unsubstituted alkylsilyl group having 3 to 30 carbon atoms, and $R_{101}$, $R_{103}$, $R_{104}$, $R_{105}$, $R_{107}$ and $R_{108}$ are a hydrogen atom.

7. The organic electroluminescence device according to claim 1 wherein in the formula (A2), $X_{101}$ is an oxygen atom.

8. The organic electroluminescence device according to claim 2 wherein in the formula (A3), $X_{102}$ and $X_{103}$ are an oxygen atom.

9. The organic electroluminescence device according to claim 3 wherein in the formula (A4), $X_{104}$ is an oxygen atom.

10. The organic electroluminescence device according to claim 1, wherein in the formula (A1), in $R_{101}$ to $R_{108}$, the halogen atom is selected from the group consisting of fluorine, chlorine, bromine and iodine, the alkyl group for the substituted or unsubstituted alkyl group is selected from the group consisting of methyl, ethyl, propyl, isopropyl, n-butyl, s-butyl, isobutyl, t-butyl, n-pentyl, n-hexyl, n-heptyl and n-octyl, the cycloalkyl group for the substituted or unsubstituted cycloalkyl group is selected from the group consisting of cyclopropyl, cyclobutyl, cyclopentyl, cyclohexyl, adamantyl and norbornyl, and the substituted or unsubstituted alkylsilyl group is selected from the group consisting of trimethylsilyl, triethylsilyl, t-butyldimethylsilyl, vinyldimethylsilyl, propyldimethylsilyl and triisopropylsilyl, in $Ar_{101}$ to $Ar_{104}$, the aryl group for the substituted or unsubstituted aryl group is selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, naphthacenyl, pyrenyl, chrysenyl, benzo[c]phenanthryl, benzo[g]chrysenyl, triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, terphenyl and fluoranthenyl, and the heterocyclic group for the substituted or unsubstituted heterocyclic group is selected from the group consisting of pyrrolyl, pyrazinyl, pyridinyl, indolyl, isoindolyl, imidazolyl, furyl, benzofuranyl, isobenzofuranyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, quinolyl, isoquinolyl, quinoxalinyl, 1-carbazolyl, 2-carbazolyl, 3-carbazolyl, 4-carbazolyl, 9-carbazolyl, phenantridinyl, acridinyl, phenanthrolinyl, phenazinyl, phenothiazinyl, phenoxazinyl, oxazolyl, oxadiazolyl, furazanyl, thienyl and benzothiophenyl, and in $R_{111}$ to $R_{117}$, the halogen atom is selected from the group consisting of fluorine, chlorine, bromine and iodine, the alkyl group for the substituted or unsubstituted alkyl group is selected from the group consisting of methyl, ethyl, propyl, isopropyl, n-butyl, s-butyl, isobutyl, t-butyl, n-pentyl, n-hexyl, n-heptyl and n-octyl, the substituted or unsubstituted alkylsilyl group is selected from the group consisting of trimethylsilyl, triethylsilyl, t-butyldimethylsilyl, vinyldimethylsilyl, propyldimethylsilyl and triisopropylsilyl, the aryl group for the substituted or unsubstituted aryl group is selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, naphthacenyl, pyrenyl, chrysenyl, benzo[c]phenanthryl, benzo[g] chrysenyl, triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, terphenyl and fluoranthenyl, and the heterocyclic group for the substituted or unsubstituted heterocyclic group is selected from the group consisting of pyrrolyl, pyrazinyl, pyridinyl, indolyl, isoindolyl, imidazolyl, furyl, benzofuranyl, isobenzofuranyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, quinolyl, isoquinolyl, quinoxalinyl, 1-carbazolyl, 2-carbazolyl, 3-carbazolyl, 4-carbazolyl, 9-carbazolyl, phenantridinyl, acridinyl, phenanthrolinyl, phenazinyl, phenothiazinyl, phenoxazinyl, oxazolyl, oxadiazolyl, furazanyl, thienyl and benzothiophenyl.

11. The organic electroluminescence device according to claim 10, wherein in the formula (A1), in $R_{101}$ to $R_{108}$, the halogen atom is fluorine, the alkyl group for the substituted or unsubstituted alkyl group is selected from the group consisting of methyl, ethyl, propyl, isopropyl, n-butyl, s-butyl, isobutyl, t-butyl, n-pentyl and n-hexyl, the cycloalkyl group for the substituted or unsubstituted cycloalkyl group is selected from the group consisting of cyclopropyl, cyclobutyl, cyclopentyl, cyclohexyl and 4-methylcyclohexyl, and the arylsilyl group for the substituted or unsubstituted arylsilyl group is triphenylsilyl, in $Ar_{101}$ to $Ar_{104}$, the heterocyclic group for the substituted or unsubstituted heterocyclic group is selected from the group consisting of 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-carbazolyl, 2-carbazolyl, 3-carbazolyl, 4-carbazolyl and 9-carbazolyl, and in $R_{111}$ to $R_{117}$, the halogen atom is fluorine, the alkyl group for the substituted or unsubstituted alkyl group is selected from the group consisting of methyl, ethyl, propyl, isopropyl, n-butyl, s-butyl, isobutyl, t-butyl, n-pentyl and n-hexyl, the alkenyl group for the substituted or unsubstituted alkenyl group is vinyl, the alkynyl group for the substituted or unsubstituted alkynyl group is ethynyl, and the heterocyclic group for the substituted or unsubstituted heterocyclic group is selected from the group consisting of 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-carbazolyl, 2-carbazolyl, 3-carbazolyl, 4-carbazolyl and 9-carbazolyl.

12. The organic electroluminescence device according to claim 1, wherein in the formula (A1), $R_{101}$ to $R_{108}$ are independently a hydrogen atom, or a group selected from the group consisting of methyl, ethyl, propyl, isopropyl, n-butyl, n-hexyl, cyclopropyl, cyclobutyl, cyclopentyl and cyclohexyl, $Ar_{101}$ to $Ar_{104}$ are independently a substituted or unsubstituted phenyl group, a substituted or unsubstituted naphthyl group, a substituted or unsubstituted biphenylyl group, a substituted or unsubstituted terphenyl group, 2-fluorenyl, 2-dibenzofuranyl, 3-dibenzofuranyl, 4-dibenzofuranyl, 2-dibenzothiophenyl, pyridinyl or quinolyl, and $R_{111}$ to $R_{117}$ are independently a hydrogen atom, or a group selected from the group consisting of methyl, t-butyl, trimethylsilyl and phenyl.

13. The organic electroluminescence device according to claim 1, wherein the substituents for any substituted groups in the formula (A1) are independently selected from the group consisting of an alkyl group, a substituted or unsubstituted silyl group, an alkoxy group, an aryl group, an aryloxy group, an aralkyl group, a cycloalkyl group, a heterocyclic group, a halogen atom, an alkyl halide group, a hydroxyl group, a nitro group, a cyano group and a carboxy group.

14. The organic electroluminescence device according to claim 13, wherein the substituents for any substituted groups in the formula (A1) are independently selected from the group consisting of methyl, ethyl, propyl, isopropyl, n-butyl, s-butyl, isobutyl, t-butyl, n-pentyl, n-hexyl, trimethylsilyl, triethylsilyl, t-butyldimethylsilyl, vinyldimethylsilyl, propyldimethylsilyl, triisopropylsilyl, triphenylsilyl, methoxy, ethoxy, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, naphthacenyl, pyrenyl, chrysenyl, benzo[c]phenanthryl, benzo[g]chrysenyl, triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, terphenyl, fluoranthenyl, phenoxy, benzyl, phenylethyl, 2-phenylpropane-2-yl, cyclopropyl, cyclobutyl, cyclopentyl, cyclohexyl, 4-methylcyclohexyl, adamantyl, norbornyl, pyrrolyl, pyrazinyl, pyridinyl, indolyl, isoindolyl, imidazolyl, furyl, benzofuranyl, isobenzofuranyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, quinolyl, isoquinolyl, quinoxalinyl, 1-carbazolyl, 2-carbazolyl, 3-carbazolyl, 4-carbazolyl, 9-carbazolyl, phenanthridinyl, acridinyl, phenanthrolinyl, phenazinyl, phenothiazinyl, phenoxazinyl, oxazolyl, oxadiazolyl, furazanyl, thienyl, benzothiophenyl, fluorine, chlorine, bromine, iodine, fluoromethyl, difluoromethyl, trifluoromethyl, fluoroethyl, trifluoromethyl, hydroxyl, nitro, cyano and carboxy.

15. The organic electroluminescence device according to claim 1, wherein the substituents for any substituted groups in the formula (A1) are independently selected from the group consisting of methyl, ethyl, isopropyl, 2,2-dimethylpropyl, t-butyl, trimethylsilyl, methoxy, phenyl, 2-phenylpropane-2-yl, cyclopentyl, cyclohexyl, fluorine, trifluoromethyl and cyano.

16. The organic electroluminescence device according to claim 1, wherein in the formula (5), $Ar^{11}$ is a substituted or unsubstituted dibenzofuranyl group, and $Ar^{12}$ is a substituted or unsubstituted monocyclic group having 5 to 50 ring atoms, a substituted or unsubstituted fused ring group having 8 to 50 ring atoms, or a group formed by combination of the monocyclic group and the fused ring group, other than a substituted or unsubstituted dibenzofuranyl group.

17. The organic electroluminescence device according to claim 16, wherein in the formula (5), $Ar^{11}$ is a substituted or unsubstituted 2-dibenzofuranyl group or a substituted or unsubstituted 4-dibenzofuranyl group.

18. The organic electroluminescence device according to claim 17, wherein in the formula (5), $Ar^{11}$ is a substituted or unsubstituted 2-dibenzofuranyl group.

19. The organic electroluminescence device according to claim 16, wherein in the formula (5), in $Ar^{12}$, the monocyclic group for the substituted or unsubstituted monocyclic group is an aromatic group or a heterocyclic group, the aromatic group is selected from the group consisting of a phenyl group, biphenyl group, terphenyl group and quaterphenyl group, and the heterocyclic group is selected from the group consisting of a pyridyl group, pyradyl group, pyrimidyl group, triadinyl group, furyl group and thienyl group; and the fused ring group for the substituted or unsubstituted fused ring group is selected from the group consisting of a fused aromatic ring group and a fused heterocyclic group, the fused aromatic ring group is selected from the group consisting of a naphthyl group, phenanthryl group, anthryl group, chrysenyl group, benzanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group and benzofluoranthenyl group, and the fused heterocyclic group is selected from the group consisting of a benzofuranyl group, benzothiophenyl group, indolyl group, dibenzofuranyl group, dibenzothiophenyl group, carbazolyl group, quinolyl group and phenanthrolinyl group.

20. The organic electroluminescence device according to claim 19, wherein in $Ar^{12}$, the monocyclic group for the substituted or unsubstituted monocyclic group is selected from the group consisting of a phenyl group, biphenyl group or terphenyl group, and the fused ring group for the substituted or unsubstituted fused ring group is selected from the group consisting of a naphthyl group, phenanthryl group, anthryl group, 9,9-dimethylfluorenyl group, fluoranthenyl group, benzanthryl group, dibenzothiophenyl group, dibenzofuranyl group and carbazolyl group.

21. The organic electroluminescence device according to claim 19, wherein $Ar^{12}$ is a substituted or unsubstituted aromatic group having 6 to 50 ring atoms.

22. The organic electroluminescence device according to claim 21, wherein $Ar^{12}$ is a substituted or unsubstituted phenyl group.

23. The organic electroluminescence device according to claim 1, wherein the substituents for any substituted groups in the formula (5) are independently selected from the group consisting of a monocyclic group having 5 to 50 ring atoms, a fused ring group having 8 to 50 ring atoms, an alkyl group having 1 to 50 carbon atoms, a cycloalkyl group having 3 to 50 ring carbon atoms, a substituted or unsubstituted silyl group, an alkoxy group having 1 to 50 carbon atoms, a cyano group and a halogen atom.

24. The organic electroluminescence device according to claim 23, wherein the substituents for any substituted groups in the formula (5) are independently selected from the group consisting of a monocyclic group having 5 to 50 ring atoms and a fused ring group having 8 to 50 ring atoms.

25. The organic electroluminescence device according to claim 24, wherein the substituents for any substituted groups in the formula (5) are independently selected from the group consisting of a phenyl group, a biphenyl group, a terphenyl group, a quaterphenyl group, a pyridyl group, a pyradyl group, a pyrimidyl group, a triadinyl group, a furyl group and a thienyl group.

26. The organic electroluminescence device according to claim 19, wherein, $Ar^{12}$ is a naphthyl group, a phenanthryl group or a benzanthryl group.

27. The organic electroluminescence device according to claim 1, wherein in formula (5), $R^{101}$ to $R^{108}$ are independently a hydrogen atom.

28. The organic electroluminescence device according to claim 4, wherein in formula (5), $R^{101}$ to $R^{108}$ are independently a hydrogen atom.

29. The organic electroluminescence device according to claim 1, which comprises the aromatic amine derivative represented by the formula (A1) as a dopant material, and the anthracene derivative represented by the formula (5) as a host material.

30. An electronic equipment comprising the organic electroluminescence device according to claim 1.

* * * * *

UNITED STATES PATENT AND TRADEMARK OFFICE

CERTIFICATE OF CORRECTION

PATENT NO. : 10,263,191 B2
APPLICATION NO. : 15/648188
DATED : April 16, 2019
INVENTOR(S) : Yumiko Mizuki, Masakazu Funahashi and Masahiro Kawamura It is certified that error appears in the above-identified patent and that said Letters Patent is hereby corrected as shown below:

In the Claims

Claim 1, Column 157, Lines 4-5:
Please delete “adjacent substituents of $R_{11}$ to $R_{117}$ may be bonded to each other to form a saturated or unsaturated ring, and”
Please insert -- adjacent substituents of $R_{111}$ to $R_{117}$ may be bonded to each other to form a saturated or unsaturated ring, and --

Claim 5, Column 159, Lines 4-5:
Please delete “The organic electroluminescence device according to claim 4 wherein in the formula (A1),”
Please insert -- The organic electroluminescence device according to claim 1 wherein in the formula (A1), --

Signed and Sealed this
Twenty-fourth Day of September, 2019

Andrei Iancu
*Director of the United States Patent and Trademark Office*